US012655131B2

(12) United States Patent
Fieni et al.

(10) Patent No.: US 12,655,131 B2
(45) Date of Patent: Jun. 16, 2026

(54) PYRAZINECARBOXAMIDE ANALOG COMPOUNDS FOR USE IN TREATING CANCER

(71) Applicant: NOVAPANO, LLC, Philadelphia, PA (US)

(72) Inventors: Francesca Fieni, San Francisco, CA (US); Son Minh Pham, San Francisco, CA (US); Sarvajit Chakravarty, Edmond, OK (US)

( * ) Notice: Subject to any disclaimer, the term of this patent is extended or adjusted under 35 U.S.C. 154(b) by 1036 days.

(21) Appl. No.: 17/761,905

(22) PCT Filed: Sep. 17, 2020

(86) PCT No.: PCT/US2020/051323

§ 371 (c)(1),
(2) Date: Mar. 18, 2022

(87) PCT Pub. No.: WO2021/055637

PCT Pub. Date: Mar. 25, 2021

(65) Prior Publication Data

US 2023/0002356 A1 Jan. 5, 2023

Related U.S. Application Data

(60) Provisional application No. 62/902,290, filed on Sep. 18, 2019.

(51) Int. Cl.

| | |
|---|---|
| ***C07D 241/28*** | (2006.01) |
| ***C07D 241/32*** | (2006.01) |
| ***C07D 401/12*** | (2006.01) |
| ***C07D 401/14*** | (2006.01) |
| ***C07D 403/12*** | (2006.01) |
| ***C07D 403/14*** | (2006.01) |
| ***C07D 405/12*** | (2006.01) |
| ***C07D 409/12*** | (2006.01) |
| ***C07D 413/12*** | (2006.01) |
| ***C07D 413/14*** | (2006.01) |
| ***C07D 417/12*** | (2006.01) |
| ***C07D 417/14*** | (2006.01) |
| ***C07D 487/04*** | (2006.01) |

(52) U.S. Cl.

CPC ......... *C07D 403/12* (2013.01); *C07D 241/28* (2013.01); *C07D 241/32* (2013.01); *C07D 401/12* (2013.01); *C07D 401/14* (2013.01); *C07D 403/14* (2013.01); *C07D 405/12* (2013.01); *C07D 409/12* (2013.01); *C07D 413/12* (2013.01); *C07D 413/14* (2013.01); *C07D 417/12* (2013.01); *C07D 417/14* (2013.01); *C07D 487/04* (2013.01)

(58) Field of Classification Search

CPC .. C07D 403/12; C07D 241/28; C07D 241/12; C07D 241/14; C07D 401/14; C07D 403/14; C07D 405/12; C07D 409/12; C07D 413/12; C07D 413/14; C07D 417/12; C07D 417/14; C07D 487/04; A61P 35/00

See application file for complete search history.

(56) References Cited

U.S. PATENT DOCUMENTS 11,260,054 B2 * 3/2022 Fieni .................... A61K 9/0019

FOREIGN PATENT DOCUMENTS

| | | | | |
|---|---|---|---|---|
| EP | 0451130 A2 | 10/1991 | | |
| WO | 2019232496 A1 | 12/2019 | | |
| WO | WO-2019232156 A1 * | 12/2019 | ......... | A61K 31/4965 |

OTHER PUBLICATIONS

"Identification of the Binding Position of Amilorides in the Quinone Binding Pocket of Mitochondrial Complex I" Ito, Takeshi; Murai, Masatoshi; Morisaka, Hironobu; Miyoshi, Hideto Biochemistry (2015), 54(23), 3677-3686; ISSN: 0006-2960 (Year: 2015).*

"Identification of the Binding Position of Amilorides in the Quinone Binding Pocket of Mitochondrial Complex I" T Ito, M Murai, H Morisaka, H Miyoshi Biochemistry 54(23), p. 3677-3686 (Year: 2015).*

"Production of new amilorides as potent inhibitors of mitochondrial respiratory complex I" M Murai, S Habu, S Murakami, T Ito, and H Miyoshi Bioscience, Biotechnology, and Biochemistry, 79(7), p. 1061-1066. (Year: 2015).*

"Bioisosterism: A Rational Approach in Drug Design" GA Patani , EJ LaVoie Chem Rev, 96(8), p. 3147-3176 (Year: 1996).*

American Cancer Society "Cancer Facts & Figures 2016,", 72 pages.

Duffy, M.J. (Apr. 2001). "Carcinoembryonic Antigen as a Marker For Colorectal Cancer: Is It Clinically Useful?" Clinical Chem. 47(4):624-630.

Höeckel, M. et al. (Oct. 1, 1996). "Association Between Tumor Hypoxia and Malignant Progression In Advanced Cancer Of The Uterine Cervix," Cancer Res 56(19):4509-4515.

International Preliminary Report on Patentability, issued Mar. 15, 2022, for PCT Application No. PCT/US2020/51323, filed Sep. 17, 2022, 6 pages.

International Search Report and Written Opinion, dated Dec. 18, 2022, for PCT Application No. PCT/US2020/51323, filed Sep. 17, 2022, 9 pages.

Massink, A. (Dec. 8, 2016). "Allosteric Modulation by Sodium Inons and Amilorides of G Protein-Coupled Receptors," Dissertation, 2 pages.

Mckeown, S.R. (Mar. 2014). "Defining Normoxia, Physoxia and Hypoxia In Tumours-Implications For Treatment Response," Br J Radiol. 87(1035):20130676, 12 pages.

Muz, B. et al. (Dec. 11, 2015). "The role Of Hypoxia In Cancer Progression, Angiogenesis, Metastasis, and Resistance To Therapy," Hypoxia 3:83-92.

PUBCHEM (Jan. 15, 2019). 135600314 - "5-(N-4-Chlorobenzyl)-N-(2',4'-dimethyl)benzamil," 15 pages.

(Continued)

*Primary Examiner* — Kara R. Mcmillian
*Assistant Examiner* — Sophia P Hirakis

(57) ABSTRACT

Provided herein are compounds, such as compounds for use in treating cancer. Also provided are methods of treating cancer, including treatment resistant cancer or cancer associated with a hypoxic tumor.

3 Claims, No Drawings

(56) References Cited

OTHER PUBLICATIONS

Remington'S Pharmaceutical Sciences, Mack Publishing Company, Philadelphia, PA, 21th ed. (2000) TOC, 4 Pages.
Secondo, A. et al. (2009). "Molecular Pharmacology of the Amiloride Analog 3-Amino-6-chloro-5-[(4-chloro-benzyl) amino]-N-[[2,4-dimethylbenzyl)-amino]iminomethyl]-pyrazinecarboxaminde (CB-DMB) as a Pan Inhibitor of the Na+-CA2+ Exchanger Isoforms NCX1, NCX2, and NCX3 in Stably Transfected Cells," The Journal of Pharmacology and Experimental Therapeutics 331(1):212-221.
SEER Cancer Statistics Review, (1975-2011), 5 pgs.

* cited by examiner

PYRAZINECARBOXAMIDE ANALOG COMPOUNDS FOR USE IN TREATING CANCER

CROSS-REFERENCE TO RELATED APPLICATIONS

This application is a national stage application under 35 U.S.C. § 371 of

International Application No. PCT/US2020/051323, filed internationally on Sep. 17, 2020. which claims the priority benefit of U.S. Provisional Application Ser. No. 62/902,290, filed Sep. 18, 2019, the content of each of which is incorporated herein by reference in its entirety.

FIELD

The present disclosure relates to compounds, such as compounds for use in treating cancer, and methods of treating cancer.

BACKGROUND

Despite numerous advances in the treatment of cancer, this disease continues to be a common and deadly condition. In the United States, a baby born in 2014-2016 has a 39.30% chance of being diagnosed with cancer, and a 19.71% chance of dying from cancer (SEER Cancer Statistics Review 1975-2016).

Certain cancers are known to be particularly difficult to treat, such as pancreatic cancer. According to the American Cancer Society, for all stages of pancreatic cancer combined, the 1- and 5-year relative survival rates are 29% and 7%, respectively. Even for the small percentage of people diagnosed with local disease (9%), the 5-year survival is only 27%. More than half (53%) of patients are diagnosed at a distant stage, for which 1- and 5-year survival is 15% and 2%, respectively (American Cancer Society. Cancer Facts & Figures 2016. Atlanta: American Cancer Society; 2016).

Additional factors can also contribute in making cancers difficult to treat, such as hypoxia or resistance to a previous treatment. Hypoxia, or a decreased level of oxygen, is an independent, adverse prognostic factor for tumor progression (Hoeckel et al. Cancer Res 1996, 56:4509-15). For most cells, including most cancer cells, hypoxia leads to anti-proliferative effects such as apoptosis and necrosis, but for a minority of cancer cells, hypoxia leads to an adaptive response with aggressive phenotypes, increased tumor progression, and increased treatment resistance. In fact, the role of hypoxia in the phenomenon of therapy resistance has been acknowledged for at least 60 years (Muz, Hypoxia, 2015, 3:83-92).

Given the common, but deadly nature of cancer and the particularly difficult to treat nature of certain cancers, there is a need for improved treatments.

BRIEF SUMMARY

In one aspect, provided is a compound of Formula (I):

(I)

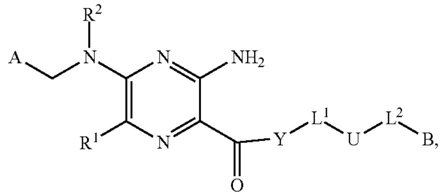

or a pharmaceutically acceptable salt thereof, wherein A, B, Y, U, $L^1$, $L^2$, $R^1$, and $R^2$ are as detailed herein.

In another aspect, provided is a method of treating cancer comprising administering to an individual in need thereof a compound detailed herein, or a pharmaceutically acceptable salt thereof, or a pharmaceutical composition detailed herein. In some embodiments, the cancer is leukemia, brain cancer, breast cancer, cervical cancer, renal cancer, liver cancer, lung cancer, pancreatic cancer, colorectal cancer, head and neck cancer, prostate cancer, vulvar cancer, skin cancer, or sarcoma. In some embodiments, the cancer is associated with a hypoxic tumor. In some embodiments, the individual has had a prior cancer treatment. In some embodiments, the cancer is resistant or refractory to the prior treatment. In some embodiments, the cancer is resistant to treatment with gemcitabine, docetaxel, paclitaxel, paclitaxel protein-bound particles, cisplatin, or radiation. In some embodiments, the method further comprises administering radiation. In some embodiments, the method further comprises administering a second anticancer agent. In some embodiments, the second anticancer agent is a taxane, a platinum-based agent, a nucleoside analog, an immune-check point inhibitor, a Cox-2 inhibitor, an anthracycline, a pyrimidine analog, a topoisomerase inhibitor, an mTOR inhibitor, a proteasome inhibitor, an angiogenesis inhibitor, a B-Raf inhibitor, or a tyrosine kinase inhibitor.

In another aspect, provided is a pharmaceutical composition comprising a compound detailed herein or a pharmaceutically acceptable salt thereof and a pharmaceutically acceptable carrier or excipient. Kits comprising a compound detailed herein or a pharmaceutically acceptable salt thereof are also provided. A compound as detailed herein or a pharmaceutically acceptable salt thereof is also provided for the manufacture of a medicament for the treatment of cancer.

DETAILED DESCRIPTION

Definitions

"Alkyl" refers to and includes saturated linear and branched univalent hydrocarbon structures and combination thereof, having the number of carbon atoms designated (i.e., $C_1$-$C_{10}$ or $C_{1-10}$ means one to ten carbons). Particular alkyl groups are those having 1 to 20 carbon atoms (a "$C_1$-$C_{20}$ alkyl" or "$C_{1-20}$ alkyl"). More particular alkyl groups are those having 1 to 8 carbon atoms (a "$C_1$-$C_8$ alkyl" or "$C_{1-8}$ alkyl"), 3 to 8 carbon atoms (a "$C_3$-$C_8$ alkyl" or "$C_{3-8}$ alkyl"), 1 to 6 carbon atoms (a "$C_1$-$C_6$ alkyl" or "$C_{1-6}$ alkyl"), 1 to 5 carbon atoms (a "$C_1$-$C_5$ alkyl" or "$C_{1-5}$ alkyl"), or 1 to 4 carbon atoms (a "$C_1$-$C_4$ alkyl" or "$C_{1-4}$ alkyl"), Examples of alkyl include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear or branched univalent hydrocarbon chain or combination thereof, having at least one site of olefinic unsaturation (i.e., having at least one moiety of the formula C═C) and having the number of carbon atoms designated (i.e., $C_2$-$C_{10}$ or $C_{2-10}$ means two to ten carbon atoms). The alkenyl group may be in "cis" or "trans" configurations, or alternatively in "E" or "Z" configurations. Particular alkenyl groups are those having 2 to 20 carbon atoms (a "$C_2$-$C_{20}$ alkenyl" or "$C_{2-20}$ alkenyl"), having 2 to 8 carbon atoms (a "$C_2$-$C_8$ alkenyl" or "$C_{2-8}$ alkenyl"), having 2 to 6 carbon atoms (a "$C_2$-$C_6$ alkenyl" or "$C_{2-6}$ alkenyl"), or having 2 to 4 carbon atoms (a "$C_2$-$C_1$ alkenyl" or "$C_{2-4}$ alkenyl"). Examples of alkenyl include, but are not limited to, groups such as ethenyl (or vinyl), prop-1-enyl, prop-2-enyl (or allyl), 2-methylprop-1-enyl, but-1-enyl, but-2-enyl, but-3-enyl, beta-1,3-dienyl, 2-methylbuta-1,3-dienyl, homologs and isomers thereof, and the like.

"Alkylene" as used herein refers to the same residues as alkyl, but having bivalency. Particular alkylene groups are those having 1 to 6 carbon atoms (a "$C_1$-$C_6$ alkylene" or "$C_{1-6}$ alkylene"), 1 to 5 carbon atoms (a "$C_1$-$C_5$ alkylene" or "$C_{1-5}$ alkylene"), 1 to 4 carbon atoms (a "$C_1$-$C_4$ alkylene" or "$C_{1-4}$ alkylene") or 1 to 3 carbon atoms (a "$C_1$-$C_3$ alkylene" or "$C_{1-3}$ alkylene"), Examples of alkylene include, but are not limited to, groups such as methylene ($—CH_2—$), ethylene ($—CH_2CH_2—$), propylene ($—CH_2CH_2CH_2—$), butylene ($—CH_2CH_2CH_2CH_2—$), and the like.

"Alkynyl" as used herein refers to an unsaturated linear or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ or $C_{2-10}$ means two to ten carbon atoms). Particular alkynyl groups are those having 2 to 20 carbon atoms (a "$C_2$-$C_{20}$ alkynyl" or "$C_{2-20}$ alkynyl"), having 2 to 8 carbon atoms (a "$C_2$-$C_8$ alkynyl" or "$C_{2-5}$ alkynyl"), having 2 to 6 carbon atoms (a "$C_2$-$C_6$ alkynyl" or "$C_{2-6}$ alkynyl"), or having 2 to 4 carbon atoms (a "$C_2$-$C_4$ alkynyl" or "$C_{2-4}$ alkynyl"). Examples of alkynyl include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Aryl" refers to and includes polyunsaturated aromatic hydrocarbon groups. Aryl may contain additional fused rings (e.g., from 1 to 3 rings). In one variation, the aryl group contains from 6 to 14 annular carbon atoms (a "$C_6$-$C_{14}$ aryl" or "$C_{6-14}$ aryl"). Examples of aryl groups include, but are not limited to, phenyl, naphthyl, biphenyl, and the like.

"Carbonyl" refers to the group C═O.

"Cycloalkyl" refers to and includes cyclic univalent hydrocarbon structures, which may be fully saturated, mono- or polyunsaturated, but which are non-aromatic, having the number of carbon atoms designated (e.g., $C_1$-$C_{10}$ or $C_{1-10}$ means one to ten carbons). Cycloalkyl can consist of one ring, such as cyclohexyl, or multiple rings, such as adamantyl, but excludes aryl groups. A cycloalkyl comprising more than one ring may be fused, spiro or bridged, or combinations thereof. A preferred cycloalkyl is a cyclic hydrocarbon having from 3 to 13 annular carbon atoms. A more preferred cycloalkyl is a cyclic hydrocarbon having from 3 to 8 annular carbon atoms (a "$C_3$-$C_8$ cycloalkyl" or "$C_{3-5}$ cycloalkyl"). Examples of cycloalkyl include, but are not limited to, cyclopropyl, cyclobutyl, cyclopentyl, cyclohexyl, 1-cyclohexenyl, 3-cyclohexenyl, cycloheptyl, norbomyl, and the like.

"Halo" or "halogen" refers to elements of the Group 17 series having atomic number 9 to 85. Preferred halo groups include fluoro, chloro, bromo and iodo. Where a residue is substituted with more than one halogen, it may be referred to by using a prefix corresponding to the number of halogen moieties attached, e.g., dihaloarvl, dihaloalkyl, trihaloaryl etc. refer to aryl and alkyl substituted with two ("di") or three ("tri") halo groups, which may be but are not necessarily the same halo; thus 4-chloro-3-fluorophenyl is within the scope of dihaloaryl. An alkyl group in which each hydrogen is replaced with a halo group is referred to as a "perhaloalkyl." A preferred perhalloalkyl group is trifluoroalkyl ($—CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy ($—OCF_3$).

"Heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. A heteroaryl group can be attached to the remainder of the molecule at an annular carbon or at an annular heteroatom. Heteroaryi may contain additional fused rings (e.g., from 1 to 3 rings), including additionally fused aryl, heteroaryl, cycloalkyl, and/or heterocyclyl rings. Examples of heteroaryl groups include, but are not limited to, pyridyl, pyrimidyl, thiophenyl, furanyl, thiazolyl, and the like.

"Heterocycle" or "heterocyclyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. Examples of heterocyclyl groups include, but are not limited to, tetrahydropyranyl, dihydropyranyl, piperidirryl piperazinyl, pyrrolidinyl, thiazolinyl, thiazolidinyl, tetrahydrofuranyl, tetrahydrothiophenyl, 2,3-dihydrobenzo[b]thiophen-2-yl, 4-amino-2-oxopyrimidin-1(2H)-yl, and the like.

"Oxo" refers to the moiety ═O.

"Optionally substituted" unless otherwise specified means that a group may be unsubstituted or substituted with one or more (e.g., 1, 2, 3, 4 or 5) of substituents which may be same or different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 2 to 5, 3 to 5, 2 to 3, 2 to 4, 3 to 4, 1 to 3, 1 to 4 or 1 to 5 substituents. Examples of substituents include, but are not limited to, $C_{1-6}$ alkyl, $C_{2-6}$ alkenyl, $C_{2-6}$ alkynyl, halogen, —CN, $—OR^{aa}$, $—SR^{aa}$, $—NR^{aa}R^{bb}$, $—NO_2$, $—C═NH(OR^{aa})$, $—C(O)R^{aa}$, $—OC(O)R^{aa}$, $—C(O)OR^{aa}$, $—C(O)NR^{aa}R^{bb}$, $—OC(O)NR^{aa}R^{bb}$, $—NR^{aa}C(O)R^{bb}$, $—NR^{aa}C(O)OR^{bb}$, $—S(O)_2R^{aa}$, $—NR^{aa}S(O)R^{bb}$, $—C(O)NR^{aa}S(O)R^{bb}$, $—NR^{aa}S(O)_2R^{bb}$, $—C(O)NR^{aa}S(O)_2R^{bb}$, $—S(O)NR^{aa}R^{bb}$, $—S(O)_2NR^{aa}R^{bb}$, $—P(O)(OR^{aa})(OR^{bb})$, $C_{3-12}$ cycloalkyl, 3- to 12-membered heterocyclyl, 5- to 10-membered heteroaryl, or $C_6$-$C_{14}$ aryl, wherein the $C_{1-6}$ alkyl, $C_{2-6}$ alkenyl, $C_{2-6}$ alkynyl, $C_{3-12}$ cycloalkyl, 3- to 12-membered heterocyclyl, 5- to 10-membered heteroaryl, and $C_{6-14}$ aryl are optionally substituted with $R^{cc}$, wherein:

$R^{aa}$ and $R^{bb}$ are each independently H, $C_{1-6}$ alkyl, $C_{2-6}$ alkenyl, $C_{2-6}$ alkynyl, $C_{3-12}$ cycloalkyl, 3- to 12-membered heterocyclyl, 5- to 10-membered heteroaryl, or $C_6$-$C_{14}$ aryl, wherein the $C_{1-6}$ alkyl, $C_{2-6}$ alkenyl, $C_{2-6}$ alkynyl, $C_{3-12}$ cycloalkyl, 3- to 12-membered heterocyclyl, 5- to 10-membered heteroaryl, and $C_6$-$C_{14}$ ary of $R^{aa}$ and $R^{bb}$ are each independently optionally substituted with $R^{cc}$, or $R^{aa}$ and $R^{bb}$ are taken together with the nitrogen atom to which they attach to form a 3- to 12-membered heterocyclyl, which is optionally substituted with $C_{1-6}$ alkyl, $C_{2-6}$ alkenyl, $C_{2-6}$ alkynyl, halogen, hydroxyl, $C_{1-6}$ alkoxy, or —CN, and wherein each $R^{cc}$ is independently $C_{1-6}$ alkyl, $C_{2-6}$ alkenyl, $C_{2-6}$ alkynyl, halogen, $C_{3-12}$ cycloalkyl, 3- to 12-membered heterocyclyl, 5- to 10-membered heteroaryl, $C_{6-14}$ aryl, —CN, or —$NO_2$.

A group optionally substituted by a list of substituents means a group which may be unsubstituted or substituted with one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 2 to 5, 3 to 5, 2 to 3, 2 to 4, 3 to 4, 1 to 3, 1 to 4 or 1 to 5 substituents.

A "pharmaceutically acceptable carrier" refers to an ingredient in a pharmaceutical formulation, other than an active ingredient. A pharmaceutically acceptable carrier includes, but is not limited to, a buffer, excipient, stabilizer, or preservative.

The term "effective amount" used herein refers to an amount of a compound or composition sufficient to treat a specified disorder, condition or disease, such as ameliorate, palliate, lessen, and/or delay one or more of its symptoms. In reference to a cancer, an effective amount comprises an amount sufficient to cause the number of cancer cells present in a subject to decrease in number and/or size and/or to slow the growth rate of the cancer cells. In some embodiments, an effective amount is an amount sufficient to prevent or delay recurrence of the disease. In the case of cancer, the effective amount of the compound or composition may: (i) reduce the number of cancer cells; (ii) inhibit, retard, slow to some extent and preferably stop cancer cell proliferation; (iii) prevent or delay occurrence and/or recurrence of the cancer; and/or (iv) relieve to some extent one or more of the symptoms associated with the cancer.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

The term "subject" or "individual" refers to a mammal and includes, but is not limited to, human, bovine, horse, feline, canine, rodent, or primate. In one embodiment, the subject or individual is a human.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. In reference to a cancer, the number of cancer cells present in a subject may decrease in number and/or size and/or the growth rate of the cancer cells may slow. In some embodiments, treatment may prevent or delay recurrence of the disease. In the case of cancer, the treatment may: (i) reduce the number of cancer cells; (ii) inhibit, retard, slow to some extent and preferably stop cancer cell proliferation; (iii) prevent or delay occurrence and/or recurrence of the cancer; and/or (iv) relieve to some extent one or more of the symptoms associated with the cancer. The methods of the invention contemplate any one or more of these aspects of treatment.

The term "simultaneous administration," as used herein, means that a first therapy and second therapy in a combination therapy are administered with a time separation of no more than about 15 minutes, such as no more than about any of 10, 5, or 1 minutes.

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first.

As used herein, the term "concurrent administration" means that the administration of the first therapy and that of a second therapy in a combination therapy overlap with each other.

As used herein, the term "hypoxic" or "hypoxia" refers to a condition wherein the oxygen concentration is lower than a normal, physiological level. As used herein, the term "normoxic" or "normoxia" refers to a condition used in cell culture wherein the oxygen concentration is approximately the same as atmospheric oxygen. A normoxic condition has a higher oxygen concentration than a normal, physiological level. As used herein, the term "hypoxic tumor" means a tumor comprising a plurality of cells that have been deprived of oxygen or where the oxygen concentration is significantly lower than in a normal, healthy tissue.

As used herein, the singular form "a," "an," and "the" includes plural references unless indicated otherwise.

Reference to "about" a value or parameter herein refers to the usual error range for the respective value readily known to the skilled person in this technical field. Reference to "about" a value or parameter herein includes (and describes) aspects that are directed to that value or parameter per se. For example, description referring to "about X" includes description of "X."

It is understood that embodiments, aspects and variations described herein also include "consisting" and/or "consisting essentially of" embodiments, aspects and variations.

Unless defined otherwise, all terms of art, notations and other technical and scientific terms or terminology used herein are intended to have the same meaning as is commonly understood by one of ordinary skill in the art to which the claimed subject matter pertains.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

Compounds

In one aspect, provided is a compound of Formula (I):

(I)

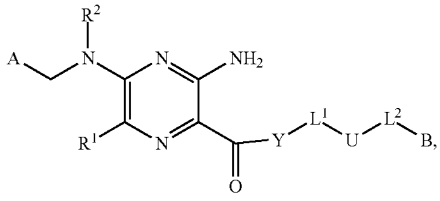

or a pharmaceutically acceptable salt thereof, wherein:

Y is —N($R^3$)— or

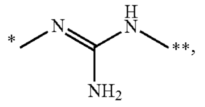

wherein:

* of Y indicates the point of attachment to the carbonyl of the parent structure and ** of Y indicates the point of attachment to -$L^1$-U-$L^2$-B;

$R^1$ is H or halo;

$R^2$ is H or $C_1$-$C_6$ alkyl;

$R^3$ is H or $C_1$-$C_6$ alkyl;

A is a phenyl substituted with 1-5 halo, which may be the same or different, or an optionally substituted 5- to 12-membered heteroaryl;

B is an optionally substituted 6- to 10-membered aryl or a 5- to 12-membered heteroaryl; U is —O—, —NH—, —N($R^4$)—, —$CF_2$—, a 5- to 12-membered heteroaryl, or an optionally substituted 4- to 8-membered heterocyclyl, wherein:

$R^4$ is $C_1$-$C_6$ alkyl;

$L^1$ is optionally substituted $C_1$-$C_5$ alkylene or *-$L^{3A}$-O-$L^{3B}$-**, wherein:

* of $L^1$) indicates the point of attachment to the Y moiety and ** of $L^1$) indicates the point of attachment to -U-$L^2$-B;

$L^{3A}$ and $L^{3B}$ are each independently optionally substituted $C_1$-$C_3$ alkylene or absent; $L^2$is *-$L^{4A}$-O-$L^{4B}$-**, *-$L^{4C}$-N($R^5$)-$L^{4D}$-**, optionally substituted $C_1$-$C_3$ alkylene, or absent, wherein:

* of $L^2$ indicates the point of attachment to the U moiety and ** of $L^2$ indicates the point of attachment to the B moiety;

$L^{4A}L^{4B}$, $L^{4C}$ and $L^{4D}$ are each independently optionally substituted $C_1$-$C_3$alkylene or absent; and $R^5$ is H or $C_1$-$C_6$ alkyl.

In some embodiments of a compound of Formula (I), or a variation thereof, Y is —N($R^3$)—. In some embodiments, Y is

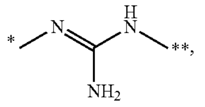

wherein * of Y indicates the point of attachment to the carbonyl of the parent structure and ** of Y indicates the point of attachment to -$L^1$-U-$L^2$-B.

In some embodiments, a compound of Formula (I) is of Formula (II):

(II)

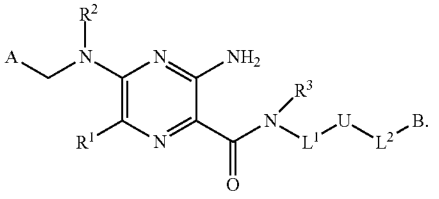

In some embodiments, a compound of Formula (I) is of Formula (III):

(III)

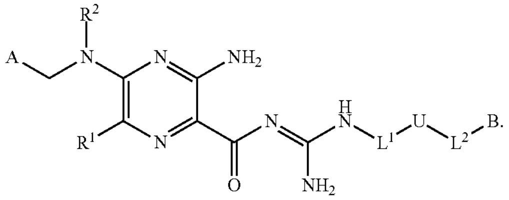

In some embodiments of a compound of Formula (I), or a variation thereof (such as Formula (II) or Formula (III)), $R^1$ is H. In some embodiments, $R^1$ is halo. In some embodiments, $R^1$ is fluoro, chloro, bromo, or iodo. In some embodiments, $R^1$ is fluoro. In some embodiments, $R^1$ is chloro. In some embodiments, $R^1$ is bromo. In some embodiments, $R^1$ is iodo. In some embodiments, $R^1$ is bromo.

In some embodiments of a compound of Formula (I), or a variation thereof (such as Formula (II) or Formula (III)), $R^2$ is H. In some embodiments, $R^2$ is $C_1$-$C_6$ alkyl, such as methyl, ethyl, n-propyl, isopropyl, n-butyl, t-butyl, isobutyl, or sec-hutyl. In some embodiments, $R^2$ is methyl.

In some embodiments of a compound of Formula (I), or a variation thereof (such as Formula (II) or Formula (III)), $R^1$ is H and $R^2$ is H. In some embodiments, $R^1$ is H and $R^2$ is $C_1$-$C_6$ alkyl. In some embodiments, $R^1$ is halo and $R^2$ is H. In some embodiments, $R^1$ is halo and $R^2$ is $C_1$-$C_6$ alkyl. In some embodiments, $R^1$ is chloro and R is H.

In some embodiments of a compound of Formula (I), or a variation thereof (such as Formula (II)), $R^3$ is H. In some embodiments, $R^3$ is $C_1$-$C_6$ alkyl, such as methyl, ethyl, n-propyl, isopropyl, n-butyl, t-butyl, isobutyl, or sec-butyl. In some embodiments, $R^3$ is methyl.

In some embodiments of a compound of Formula (I), or a variation thereof (such as Formula (II)), $R^1$ is H and $R^3$ is H. In some embodiments, $R^1$ is H and $R^3$ is $C_1$-$C_6$ alkyl. In some embodiments, $R^1$ is halo and $R^3$ is H. In some embodiments, $R^1$ is halo and $R^3$ is $C_1$-$C_6$ alkyl. In some embodiments, $R^1$ is chloro and $R^3$ is H. In some embodiments, $R^2$ is H and $R^3$ is H. In some embodiments, $R^2$ is H and $R^3$ is $C_1$-$C_6$ alkyl. In some embodiments, $R^2$ is $C_1$-$C_6$ alkyl and $R^3$ is H. In some embodiments, $R^2$ is $C_1$-$C_6$ alkyl and $R^3$ is $C_1$-$C_6$ alkyl. In some embodiments, $R^1$ is H; $R^2$ is H; and $R^3$ is H. In some embodiments, $R^1$ is H; $R^2$ is H; and $R^3$ is $C_1$-$C_6$ alkyl, In some embodiments, $R^1$ is H; $R^2$ is $C_1$-$C_6$ alkyl; and $R^3$ is H. In some embodiments, $R^1$ is H; $R^2$ is $C_1$-$C_6$ alkyl; and $R^3$ is $C_1$-$C_6$ alkyl. In some embodiments, $R^1$ is halo; $R^2$ is H; and $R^3$ is H. In some embodiments, $R^1$ is halo; $R^2$ is H; and $R^3$ is $C_1$-$C_6$ alkyl. In some embodiments, $R^1$ is halo; $R^2$ is $C_1$-$C_6$ alkyl; and $R^3$ is H. In some embodiments, $R^1$ is halo; $R^2$ is $C_1$-$C_6$ alkyl; and $R^3$ is $C_1$-$C_6$ alkyl. In some embodiments, $R^1$ is chloro; $R^2$ is H; and $R^3$ is H.

In some embodiments of a compound of Formula (I), or a variation thereof (such as Formula (II) or Formula (III)), A is a phenyl substituted with 1-5 halo. In some embodiments, A is a phenyl substituted with 1 halo. In some embodiments, A is a phenyl substituted with 2 halo. In some embodiments, A is a phenyl substituted with 3 halo. In some embodiments, A is a phenyl substituted with 4 halo. In some embodiments, A is a phenyl substituted with 5 halo. In some embodiments, A is a phenyl substituted with 1-2 halo. In some embodiments, A is a phenyl substituted with 1-3 halo. Where more than one halo is present, the halo groups may be the same or different. In some embodiments, A is a phenyl substituted with at least one chloro. In some embodiments, A is a phenyl substituted with at least one iodo. In some embodiments, A is a phenyl substituted with at least one fluoro. In some embodiments, A is a phenyl substituted with at least one bromo. In some embodiments, A is

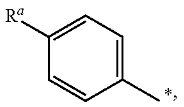

wherein * indicates the point of attachment to the remainder of the molecule and $R^a$ is H or halo. In some embodiments, $R^a$ is H. In some embodiments, $R^a$ is halo. In some embodiments, $R^a$ is fluoro, chloro, bromo, or iodo. In some embodiments, $R_a$ is fluoro, chloro, or iodo. In some embodiments, $R^a$ is fluoro. In some embodiments, $R^a$ is chloro. In some embodiments, $R^a$ is bromo. In some embodiments, $R^a$ is iodo.

In some embodiments, a compound of Formula (I) is of any one of Formula (I-1), (II-1), and (III-1) or a pharmaceutically acceptable salt thereof, wherein $R^1$, $R^2$, Y, $L^1$, U, $L^2$, and B are as detailed herein for Formula (I) and $R^a$ is H or halo. In some embodiments, a compound of Formula (I) is of Formula (I-1). In some embodiments, a compound of Formula (I) is of Formula (II-1). In some embodiments, a compound of Formula (I) is of Formula (III-1).

(I-1)

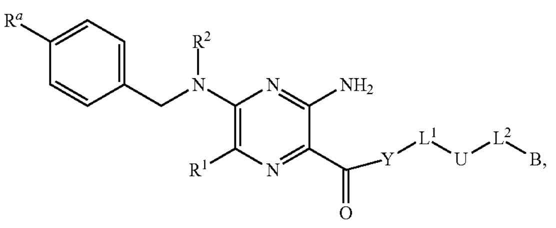

-continued (II-1)

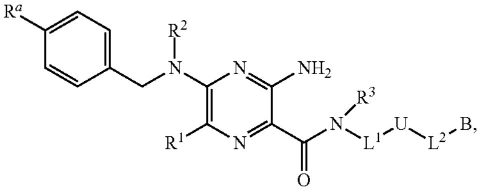

and (III-1)

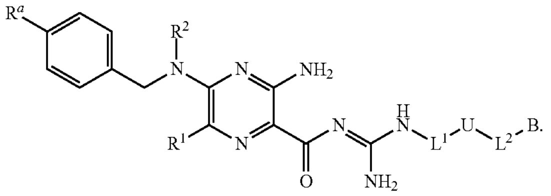

In some embodiments of a compound of Formula (I), or a variation thereof, A is an optionally substituted 5- to 12-membered heteroaryl. In some embodiments, A is a 5- to 12-membered heteroaryl, which is unsubstituted. In some embodiments, A is an optionally substituted 5- to 12-membered heteroaryl comprising at least one annular nitrogen atom. In some embodiments, A is a 5- to 12-membered heteroaryl comprising at least one annular nitrogen atom, which is unsubstituted. In some embodiments, A is an optionally substituted 5- to 6-membered heteroaryl. In some embodiments, A is a 5- to 6-membered heteroaryl, which is unsubstituted. In some embodiments, A is an optionally substituted 5- to 6-membered heteroaryl comprising at least one annular nitrogen atom. In some embodiments, A is a substituted 5- to 6-membered heteroaryl comprising at least one annular nitrogen atom, which is unsubstituted. In some embodiments, A is an optionally substituted 5-membered heteroaryl. In some embodiments, A is a 5-membered heteroaryl, which is unsubstituted. In some embodiments, A is an optionally substituted 5-membered heteroaryl comprising at least one annular nitrogen atom. In some embodiments, A is a 5-membered heteroaryl comprising at least one annular nitrogen atom, which is unsubsituted. In some embodiments, A is an optionally substituted 6-membered heteroaryl. In some embodiments, A is a 6-membered heteroaryl, which is unsubstituted. In some embodiments, A is an optionally substituted 6-membered heteroaryl comprising at least one annular nitrogen atom. In some embodiments, A is an optionally substituted 6-membered heteroaryl comprising at least one annular nitrogen atom, which is unsubstituted. In some embodiments, A is optionally substituted oxazolyl, optionally substituted thiazolyl, optionally substituted imidazolyl, or optionally substituted pyridinyl. In some embodiments, A is optionally substituted oxazolyl, In some embodiments, A is optionally substituted thiazolyl. In some embodiments, A is optionally substituted imidazolyl. In some embodiments, A is oxazolyl, thiazolyl, imidazolyl, or pyridinyl. In some embodiments, A is oxazolyl. In some embodiments, A is thiazolyl. In some embodiments, A is imidazolyl. In some embodiments, A is pyridinyl.

In some embodiments of a compound of Formula (I), or a variation thereof, A is a 5- to 12-membered heteroaryl optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, A is a 5- to 12-membered heteroaryl comprising at least one annular nitrogen atom, which is optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl in some embodiments, A is a 5- to 6-membered heteroaryl optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl In some embodiments, A is a 5- to 6- membered heteroaryl comprising at least one annular nitrogen atom, which is optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, A is a 5-membered heteroaryl optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In sonic embodiments, A is a 5-membered heteroaryl comprising at least one annular nitrogen atom, which is optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, A is a 6-membered heteroaryl optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, A is a 6-membered heteroaryl comprising at least one annular nitrogen atom, which is optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, A is oxazolyl, thiazolyl, imidazolyl, or pyridinyl, each of which is optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl.

In some embodiments of a compound of Formula (I), or a variation thereof, A is

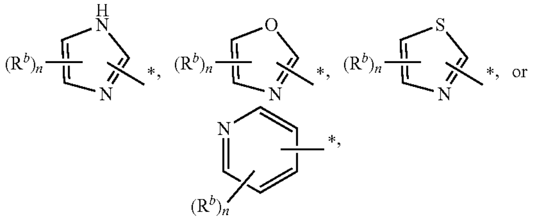

wherein each n is independently 0,1, or 2; each $R^b$ is independently $C_{1-6}$ alkyl, $C_{2-6}$ alkenyl, $C_{2-6}$ alkynyl, halo, —CN, —$NH_2$, $C_{3-12}$ cycloalkyl, 3- to 12-membered heterocyclyl, 5- to 10-membered heteroaryl, or $C_6$-$C_{14}$ aryl; and * of A indicates the point of attachment to the remainder of the molecule. In some embodiments, n is 0. In some embodiments, n is 0 or 1. In some embodiments, n is 1. In some embodiments, n is 2. In some embodiments, A is

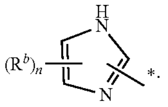

In some embodiments, A is

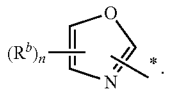

In some embodiments, A is

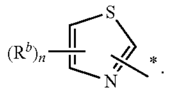

In some embodiments, A is

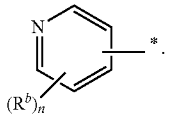

In some embodiments, A is

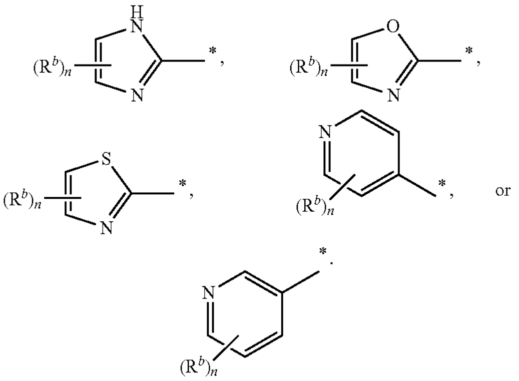

In some embodiments, A is

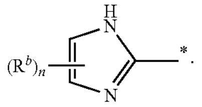

In some embodiments, A is

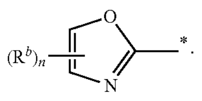

In some embodiments, A is

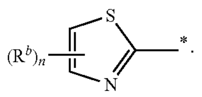

In some embodiments, A is

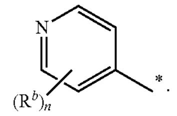

In some embodiments, A is

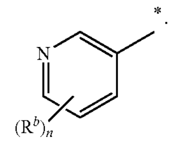

n some embodiments, A is

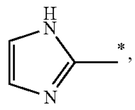,

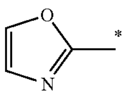,

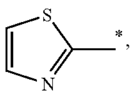,

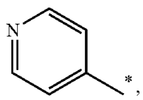, or

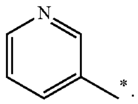.

In some embodiments, A is

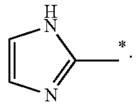.

In some embodiments, A is

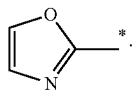.

In some embodiments, A is

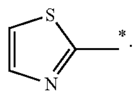.

In some embodiments, A is

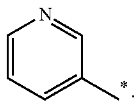.

In some embodiments, A is

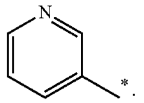.

In some embodiments, a compound of Formula (I) is of any one of Formula (I-2)-(I-6), (II-2)-(II-6), and (III-2)-(III-6), wherein $R^1$, $R^2$, Y, $L^1$, U, $L^2$, and B are as detailed herein for Formula (I); each n is independently 0, 1, or 2; and each $R^b$ is independently $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, a compound of Formula (I) is of Formula (I-2). In some embodiments, a compound of Formula (I) is of Formula (I-3). In some embodiments, a compound of Formula (I) is of Formula (I-4). In some embodiments, a compound of Formula (I) is of Formula (I-5), in some embodiments, a compound of Formula (I) is of Formula (I-6). In some embodiments, a compound of Formula (I) is of Formula (II-2). In some embodiments, a compound of Formula (I) is of Formula (II-3). In some embodiments, a compound of Formula (I) is of Formula (II-4). In some embodiments, a compound of Formula (I) is of Formula (II-5). In some embodiments, a compound of Formula (I) is of Formula (II-6). In some embodiments, a compound of Formula (I) is of Formula (III-2). In some embodiments, a compound of Formula (I) is of Formula (III-3). In some embodiments, a compound of Formula (I) is of Formula (III-4). In some embodiments, a compound of Formula (I) is of Formula (III-5). In some embodiments, a compound of Formula (I) is of Formula (III-6). Such formulae are of the following structures:

(I-2)

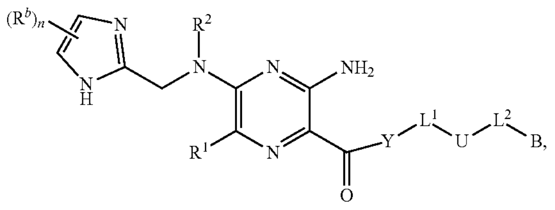

(II-2)

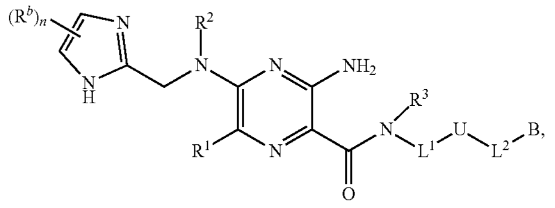

(III-2)

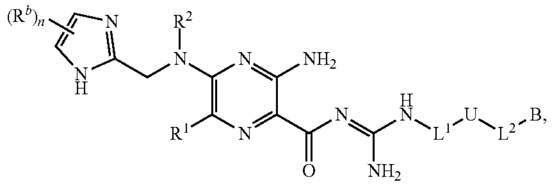

-continued (I-3)

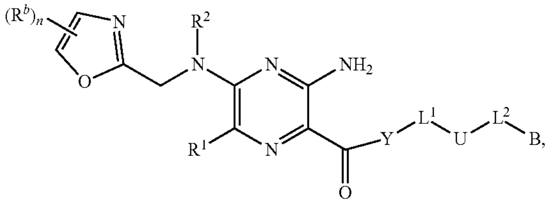

(II-3)

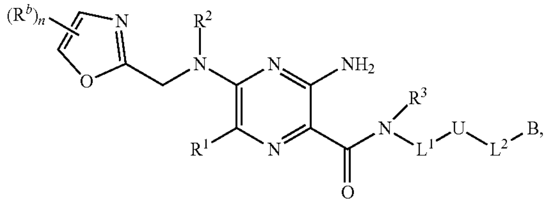

(III-3)

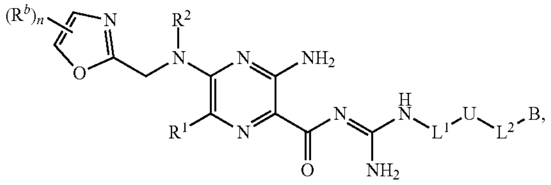

(I-4)

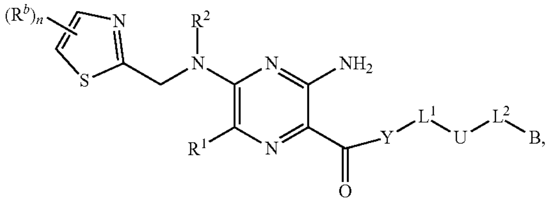

(II-4)

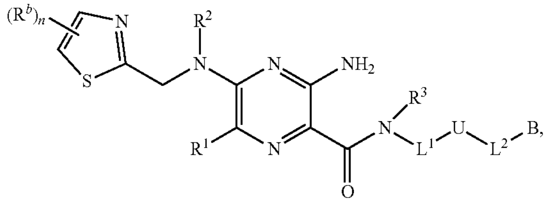

(III-4)

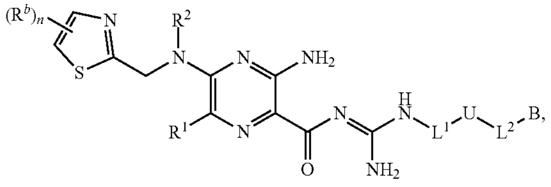

(I-5)

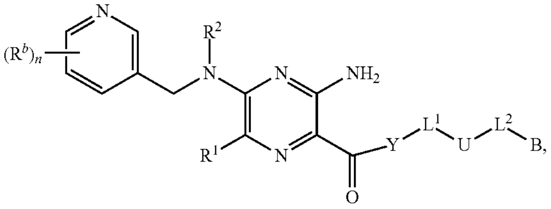

-continued (II-5)

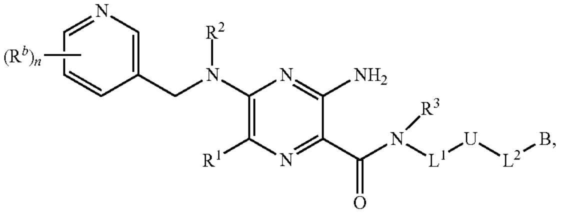

(III-5)

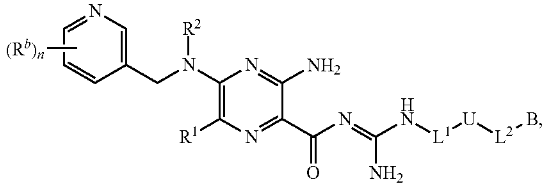

(I-6)

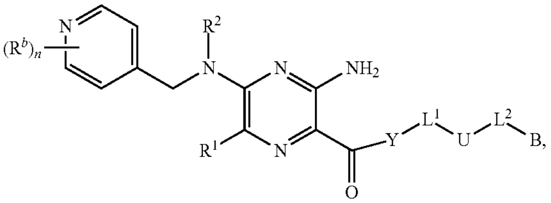

(II-6)

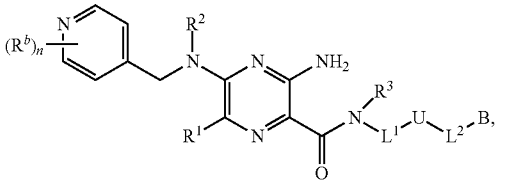

and (III-6)

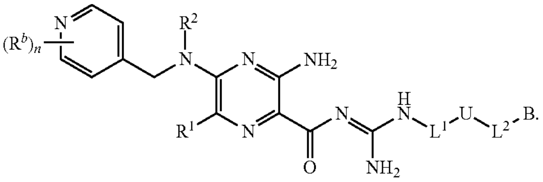

In some embodiments of a compound of Formula (I), or a variation thereof, B is an optionally substituted 6- to 10-membered aryl. In some embodiments, B is a 6- to 10-membered aryl, which is unsubstituted. In some embodiments, B is an optionally substituted phenyl or an optionally substituted naphthalenyl. In some embodiments, B is an optionally substituted phenyl. In some embodiments, B is a phenyl, which is unsubstituted. In some embodiments, B is an optionally substituted naphthalenyl. In some embodiments, B is a naphthalenyl, which is unsubstituted. In some embodiments, B is a 6- to 10-membered aryl optionally substituted with $C_{1-6}$ alkyl, $C_{2-6}$ alkenyl, $C_{2-6}$ alkynyl, halo, —CN, —OH, —$NH_2$, $C_{3-12}$ cycoalkyl, 3- to 12-membered heterocyclyl, 5- to 10-membered heteroaryl, or $C_6$-$C_{14}$ aryl. In some embodiments, B is a phenyl or naphthalenyl, each of which is optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, B is a phenyl optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, B is a naphthalenyl optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl.

In some embodiments of a compound of Formula (I), or a variation thereof, B is a phenyl substituted with 1-5 halo, In some embodiments, B is a phenyl optionally substituted with 1-5 halo. In some embodiments, B is a phenyl substituted with 1 halo. In some embodiments, B is a phenyl substituted with 2 halo. In some embodiments, B is a phenyl substituted with 3 halo. In some embodiments, B is a phenyl substituted with 4 halo. In some embodiments, B is a phenyl substituted with 5 halo. In some embodiments, B is a phenyl substituted with 1-2 halo. In some embodiments, B is a phenyl substituted with 1-3 halo. Where more than one halo is preset, the halo groups may be the same or different. In some embodiments, A is a phenyl substituted with at least one chloro. In some embodiments, B is a phenyl substituted with at least one bromo. In some embodiments, B is a phenyl substituted with at least one iodo. In some embodiments, B is a phenyl substituted with at least one fluoro.

In some embodiments of a compound of Formula , or a variation thereof, B is an optionally substituted 5- to 12-membered heteroaryl. In some embodiments, B is a 5- to 12-membered heteroaryl, which is unsubstituted. In some embodiments, B is an optionally substituted bicyclic 5- to 12-membered heteroaryl. In some embodiments, B is a bicyclic 5- to 12-membered heteroaryl, which is unsubstituted. In some embodiments, B is an optionally substituted 5- to 6-membered heteroaryl. In some embodiments, B is a 5- to 6-membered heteroaryl, which is unsubstituted. In some embodiments, B is an optionally substituted 5-membered heteroaryl. In some embodiments, B is a 5-membered heteroaryl, which is unsubstituted. In some embodiments, B is an optionally substituted 6-membered heteroaryl. In some embodiments, B is a 6-membered heteroaryl, which is unsubstituted. In some embodiments, B is optionally substituted oxazolyl, optionally substituted thiazolyl, optionally substituted imidazolyl, optionally substituted benzofuranyl, optionally substituted furanyl, optionally substituted thiophenyl, optionally substituted benzofuranyl, optionally substituted benzothiophenyl, or optionally substituted indolyl. In some embodiments, B is optionally substituted oxazolyl. In some embodiments, B is optionally substituted thiazolyl. In some embodiments, B is optionally substituted imidazolyl. In some embodiments, B is optionally substituted pyridinyl. In some embodiments, B is optionally substituted furanyl. In some embodiments, B is optionally substituted thiophenyl. In some embodiments, B is optionally substituted thiophenyl, optionally substituted benzofuranyl. In some embodiments, B is optionally substituted benzothiophenyl. In some embodiments, B is optionally substituted benzothiophenyl.

In some embodiments of a compound of Formula (I), or a variation thereof, B is a 5- to 12-membered heteroaryl, which is optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, B is a bicyclic 5- to 12-membered heteroaryl, which is optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, B is a 5- to 6-membered heteroaryl, which is optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, B is a 5-membered heteroaryl, which is optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, B is a 6-membered heteroaryl, which is optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, B is oxazolyl, thiazolyl, imidazolyl, pyridinyl, furanyl, thiophenyl, benzofuranyl, benzothiophenyl, or indolyl, each of which is optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl.

In some embodiments of a compound of Formula (I), or a variation thereof, B is

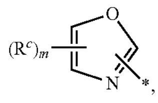,
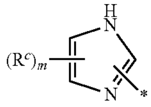,
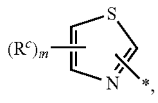,
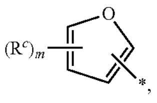,
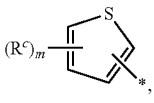,
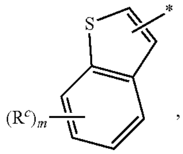,
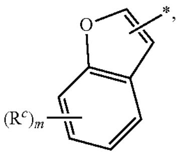,
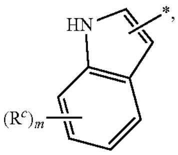,
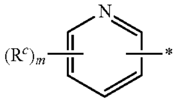,
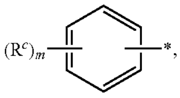, or
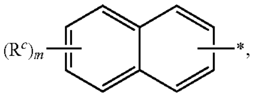, wherein each m is independently 0, 1, or 2; each $R^c$ is independently $C_{1-6}$ alkyl, $C_{2-6}$ alkenyl, $C_{2-6}$ alkynyl, halo, —CN, —$NH_2$, $C_{3-12}$ cycloalkyl, 3- to 12-membered heterocyclyl, 5- to 10-membered heteroaryl, or $C_6$-$C_{14}$ aryl; and * of B indicates the point of attachment to the remainder of the molecule. In some embodiments, m is 0. In some embodiments, m is 1. In some embodiments, m is 2. In some embodiments, $R^c$ is halo. In some embodiments, m is 0 or 1; and $R^c$ is halo. In some embodiments, B is

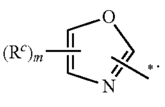.

In some embodiments, B is

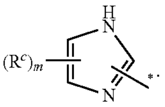.

In some embodiments, B is

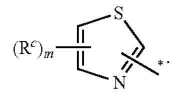

In some embodiments, B is

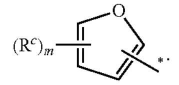

In some embodiments, B is

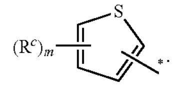

In some embodiments, B is

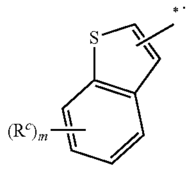

In some embodiments, B is

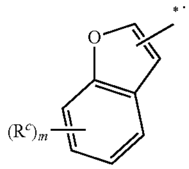

In some embodiments, B is

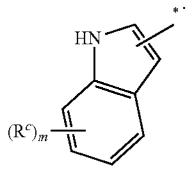

In some embodiments, B is

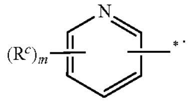

In some embodiments, B is

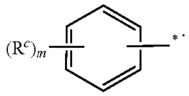

In some embodiments, B is

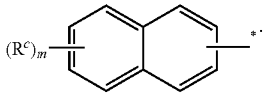

It is understood that * indicates the point of attachment to $L^2$. B may be attached to $L^2$ via any annular atom, where valence allows.

In some embodiments of a compound of Formula (I), or a variation thereof, B is

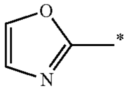, 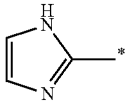, 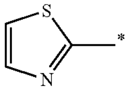,

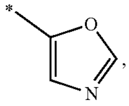, 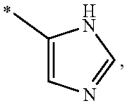, 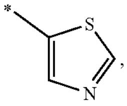, 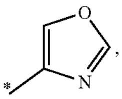,

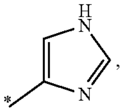, 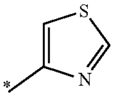, 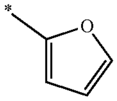, 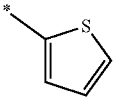,

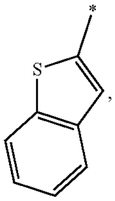, 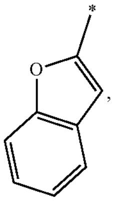, 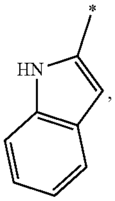, 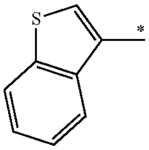,

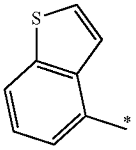,

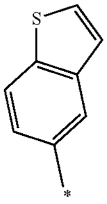, 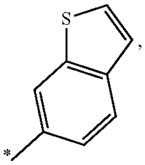, 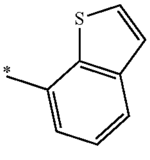,

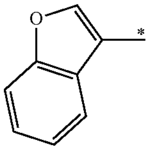, 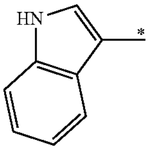, 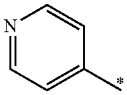,

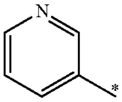, 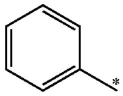, 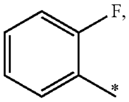,

-continued

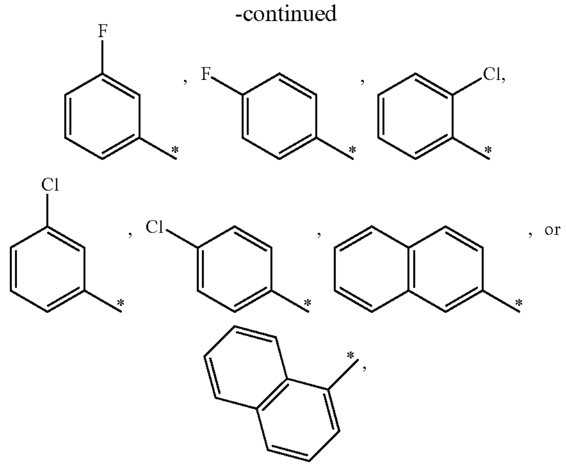

wherein * of B indicates the point of attachment to the remainder of the molecule. In some embodiments, B is

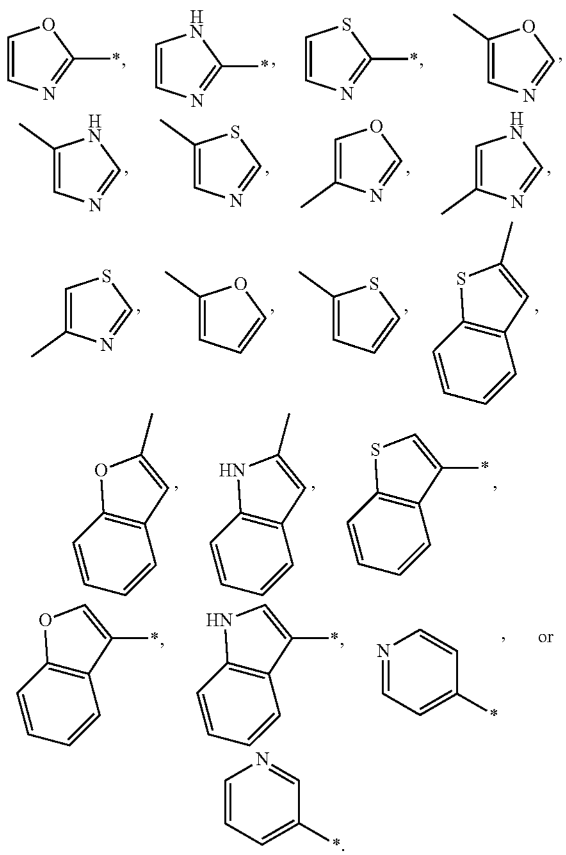

In some embodiments, B is

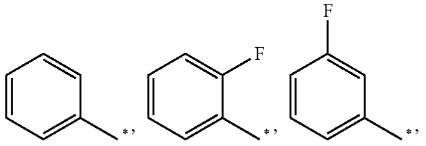

-continued

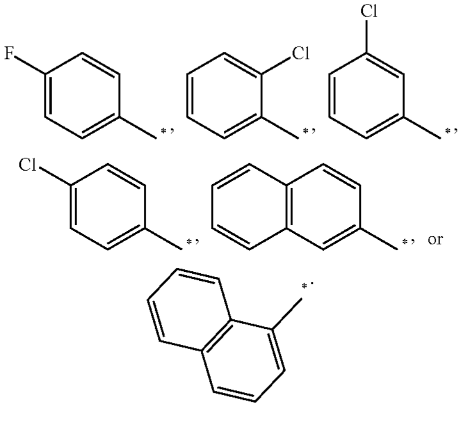

In some embodiments of a compound of Formula (I), or a variation thereof, A is a phenyl substituted with 1-5 halo; and B is an optionally substituted 6- to 10-membered aryl. In some embodiments, A is a phenyl substituted with 1-5 halo; and B is an optionally substituted 5- to 12-membered heteroaryl. In some embodiments, A is an optionally substituted 5- to 12-membered heteroaryl; and B is an optionally substituted 6- to 10-membered aryl. In some embodiments, A is an optionally substituted 5- to 12-membered heteroaryl; and B is an optionally substituted 5- to 12-membered heteroaryl. In some embodiments, A is a phenyl substituted with 1-5 halo; and. B is a 6- to 10-membered aryl optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, A is a phenyl substituted with 1-5 halo; and B is a 6- to 10-membered aryl optionally substituted with halo. In some embodiments, A is a phenyl substituted with 1-5 halo; and B is a 5- to 12-membered heteroaryl optionally substituted with $C_{1-6}$ alkyl, $C_{2-6}$ alkenyl, $C_{2-6}$ alkynyl, halo, —CN, —$NH_2$, $C_{3-12}$ cycloalkyl, 3- to 12-membered heterocyclyl, 5- to 10-membered heteroaryl, or $C_6$-$C_{14}$ aryl. In some embodiments, A is a 5- to 12-membered heteroaryl optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl; and B is a 6- to 10-membered aryl optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, A is a 5- to 12-membered heteroaryl optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl; and B is a 5- to 12-membered heteroaryl optionally substituted with $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl.

In some embodiments of a compound of Formula (I), or a variation thereof, U is —O—. In some embodiments, U is —NH—. In some embodiments. U is —N($R^4$)—. In some embodiments, U is —$CF_2$—. In some embodiments, U is a 5- to 12-membered heteroaryl. In some embodiments, U is 5- to 6-membered heteroaryl. In some embodiments, U is a 5-membered heteroaryl. In some embodiments, U is a 6-membered heteroaryl. In some embodiments, U is imidazolyl. In some embodiments, U is

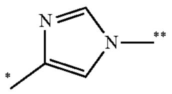 or 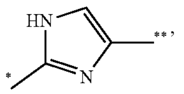

wherein * of U indicates the point of attachment to the $L^1$ moiety and ** of U indicates the point of attachment to $-L^2$-B. In some embodiments, U is

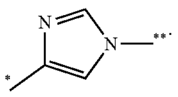

In some embodiments, U is

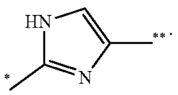

In some embodiments, U is an optionally substituted 4- to 8-membered heterocyclyl. In some embodiments, U is an optionally substituted 4- to 8-membered heterocyclyl comprising at least one annular nitrogen atom. In some embodiments, U is a 4- to 8-membered heterocyclyl optionally substituted with oxo, $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, U is a 4- to 8-membered heterocyclyl comprising at least one annular nitrogen atom, which is optionally substituted with oxo, $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, U is

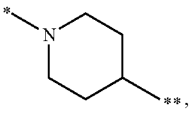 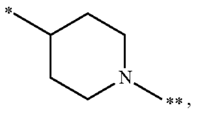

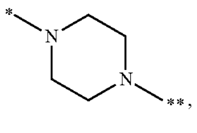 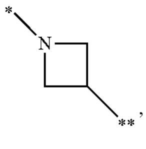 or

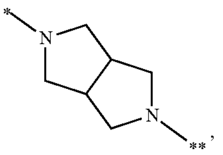

wherein * of U indicates the point of attachment the $L^1$ moiety and ** of U indicates the point of attachment to $-L^2$-B. In some embodiments, U is

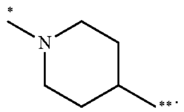

In some embodiments, U is

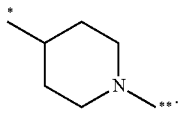

In some embodiments, U is

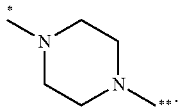

In some embodiments, U is

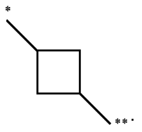

In some embodiments, U is

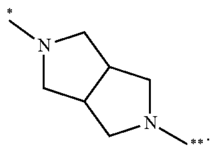

In some embodiments, U is a 4- to 8-membered heterocyclyl optionally substituted with oxo. In some embodiments, U is a 4- to 8-membered heterocyclyl substituted with oxo. In some embodiments, U is

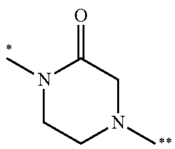 or 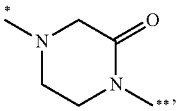

wherein: * of U indicates the point of attachment to the $L^1$ moiety and ** of U indicates the point of attachment to $-L^2$-B. In some embodiments, U is

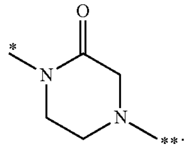

In some embodiments, U is

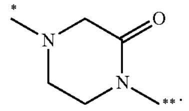

In some embodiments, U is an optionally substituted 4- to 8-membered heterocyclyl or —O—. In some embodiments, U is a 4- to 8-membered heterocyclyl or —O—.

In some embodiments of a compound of Formula (I), or a variation thereof, $L^1$ is an optionally substituted $C_1$-$C_5$ alkylene. In some embodiments, $L^1$ is a $C_1$-$C_5$ alkylene optionally substituted with oxo, $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, I) is a $C_1$-$C_5$ alkylene optionally substituted with oxo. In some embodiments, $L^1$ is a $C_1$-$C_5$ alkylene which is unsubstituted. In some embodiments, $L^1$ is a $C_1$-$C_5$ alkylene which is substituted with oxo. In some embodiments, $L^1$ is

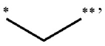 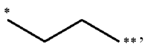 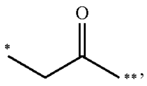

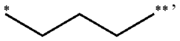 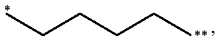 or

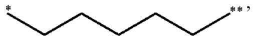

wherein * of $L^1$ indicates the point of attachment to the Y moiety and ** of $L^1$ indicates the point of attachment to -U-$L^2$-B.

In some embodiments of a compound of Formula (I), or a variation thereof, $L^1$ is *-$L^{3A}$-O-$L^{3B}$-**, wherein $L^{3A}$ and $L^{3B}$ are each independently optionally substituted $C_1$-$C_3$ alkylene or absent. In some embodiments, $L^1$ is *-$L^{3A}$-O-$L^{3B}$-**, wherein $L^{3A}$ and $L^{3B}$ are each independently $C_1$-$C_3$ alkylene or absent, wherein the $C_1$-$C_3$ alkylene of $L^{3A}$ and $L^{3B}$ are each independently optionally substituted with oxo, $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, $L^1$ is *-$L^{3A}$-O-$L^{4B}$-**, wherein $L^{3A}$ and $L^{3B}$ are each independently $C_1$-$C_3$alkylene or absent, wherein the $C_1$-$C_3$alkylene of $L^{3A}$ and $L^{3B}$ are each independently optionally substituted with oxo. In some embodiments, $L^1$ is *-$L^{3A}$-O-$L^{3B}$-**, wherein $L^{3A}$ and $L^{3B}$ are each independently $C_1$-$C_3$ alkylene or absent. In some embodiments, $L^1$ is *-$L^{3A}$-O-$L^{3B}$-**, wherein $L^{3A}$ is $C_1$-$C_3$alkylene and $L^{3B}$ is absent. In some embodiments, $L^1$ is *-$L^{3A}$-O-$L^{3B}$-**, wherein $L^{3A}$ is $C_1$-$C_3$ alkylene and $L^{3B}$ is $C_1$-$C_3$ alkylene. In some embodiments, $L^1$ is *-$L^{3A}$-O-$L^{3B}$-**, wherein $L^{3A}$ is absent and $L^{38}$ is $C_1$-$C_3$ alkylene. In some embodiments, $L^1$ is

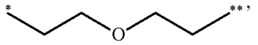

wherein * of indicates the point of attachment to the Y moiety and ** of $L^1$ indicates the point of attachment to -U-$L^2$-B.

In some embodiments of a compound of Formula (I), or a variation thereof, $L^1$ is

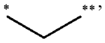 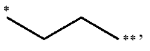 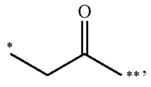

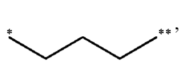 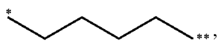

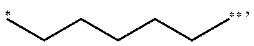 or

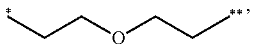

wherein * of $L^1$ indicates the point of attachment to the Y moiety and ** of $L^1$ indicates the point of attachment to -U-$L^2$-B. In some embodiments, $L^1$ is

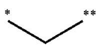

. In some embodiments, $L^1$ is

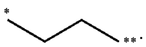

In some embodiments, $L^1$ is

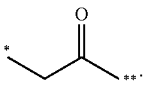

In some embodiments, $L^1$ is

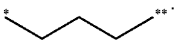

In some embodiments, $L^1$ is

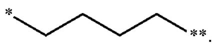

In some embodiments, $L^1$ is

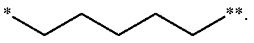.

In some embodiments, $L^1$ is

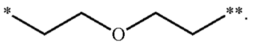.

In some embodiments of a compound of Formula (I), or a variation thereof, $L^2$ is *-$L^{4A}$-O-$L^{4B}$-**, wherein $L^{4A}$ and $L^{4B}$ are each independently optionally substituted $C_1$-$C_3$ alkylene or absent and * of $L^2$ indicates the point of attachment to the U moiety and ** of $L^2$ indicates the point of attachment to the B moiety. In some embodiments, $L^2$ is *-$L^{4A}$-O-$L^{4B}$-**, wherein $L^{4A}$ and $L^{4B}$ are each independently $C_1$-$C_3$ alkylene or absent, wherein the $C_1$-$C_3$ alkylene of $L^{4A}$ and $L^{48}$ are each independently optionally substituted with oxo, $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, $L^2$ is *-$L^{4A}$-O-$L^{4B}$-**, wherein $L^{4A}$ is an optionally substituted $C_1$-$C_3$alkylene and $L^{4B}$ is an optionally substituted $C_1$-$C_3$ alkylene. In some embodiments, $L^2$ is *-$L^{4A}$-O-$L^{4B}$-** wherein $L^{4A}$ is an optionally substituted $C_1$-$C_3$ alkylene and $L^{4B}$ is absent. In some embodiments, $L^2$ is *-$L^{4A}$-O-$L^{4B}$-**, wherein $L^{4A}$ is absent and $L^{4B}$ is an optionally substituted $C_1$-$C_3$ alkylene.

In some embodiments of a compound of Formula (I), or a variation thereof, $L^2$ is *-$L^{4A}$-O-$L^{4B}$-**, wherein $L^{4A}$ is a $C_1$-$C_3$alkylene and $L^{4B}$ is a $C_1$-$C_3$ alkylene, each of which is independently optionally substituted with oxo, $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, $L^2$ is *-$L^{4A}$-O-$L^{4B}$-***, wherein $L^{4A}$ is a $C_1$-$C_3$ alkylene and $L^{4B}$ is a $C_1$-$C_3$ alkylene, each of which is independently optionally substituted with oxo. In some embodiments, $L^2$ is *-$L^{4A}$-O-$L^{4B}$-**, wherein $L^{4A}$ is a $C_1$-$C_3$ alkylene optionally substituted with oxo, $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl and $L^{4B}$ is absent. In some embodiments, $L^2$ is *-$L^{4A}$-O-$L^{4B}$-**, wherein $L^{4A}$ is a $C_1$-$C_3$ alkylene optionally substituted with oxo and $L^{4B}$ is absent. In some embodiments, $L^2$ is *-$L^{4A}$-O-$L^{4B}$-**, wherein $L^{4A}$ is absent and $L^{4B}$ is a $C_1$-$C_3$ alkylene optionally substituted with oxo, $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, $L^2$ is *-$L^{4A}$-O-$L^{4B}$-**, wherein $L^{4A}$ is absent and $^{L4B}$ is a $C_1$-$C_3$ alkylene optionally substituted with oxo. In some embodiments, $L^2$ is *-$L^{4A}$-O-$L^{4B}$-**, wherein $L^{4A}$ is absent and $L^{4B}$ is a $C_1$-$C_3$ alkylene substituted with oxo. In some embodiments, $L^2$ is

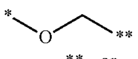, 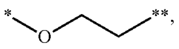,

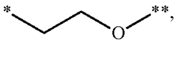, or 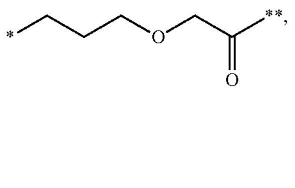, wherein * of $L^1$ indicates the point of attachment to the Y moiety and ** of $L^1$ indicates the point of attachment to -U-$L^2$-B.

In some embodiments of a compound of Formula (I), or a variation thereof, $L^2$ is *-$L^{4C}$-N($R^5$)-$L^{4D}$-**, wherein $L^{4C}$ and $L^{4D}$ are each independently optionally substituted $C_1$-$C_3$ alkylene or absent, and $R^5$ is H or $C_1$-$C_6$ alkyl. In some embodiments, $R^5$ is H. In some embodiments, $R^5$ is $C_1$-$C_6$ alkyl. In some embodiments, $L^2$ is *-$L^{4C}$-N($R^5$)-$L^{4D}$-**, wherein $L^{4C}$ and $L^{4D}$ are each independently optionally $C_1$-$C_3$ alkylene or absent, wherein the $C_1$-$C_3$ alkylene of $L^{4C}$ and $L^{4D}$ are each independently optionally substituted with oxo, $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, $L^3$ is *-$L^{4C}$-N($R^5$)-$L^{4D}$-**, wherein $L^{4C}$ and $L^{4D}$ are each independently $C_1$-$C_3$ alkylene or absent. In some embodiments, $L^2$ is *-$L^{4C}$-N($R^5$)-$L^{4D}$-**, wherein $L^{4C}$ is $C_1$-$C_3$ alkylene and $L^{4D}$ is absent. In some embodiments, $L^2$ is *-$L^{4C}$-N($R^5$)-$L^{4D}$-**, wherein $L^{4C}$ is absent and $L^{4D}$ is $C_1$-$C_3$ alkylene. In some embodiments $L^2$ is *-$L^{4C}$-N($R^5$)-$L^{4D}$-**, wherein $L^{4C}$ is $C_1$-$C_3$ alkylene and $L^{4D}$ is $C_1$-$C_3$ alkylene. In some embodiments, $L^2$ is *-$L^{4C}$-N($R^5$)-$L^{4D}$-**, wherein $L^{4C}$ is $C_1$-$C_3$ alkylene; $L^{4D}$ is absent; and $R^5$ is H. In some embodiments, $L^2$ is *-$L^{4C}$-N($R^5$)-$L^{4D}$-**, wherein $L^{4C}$ is absent; $L^{4D}$ is $C_1$-$C_3$ alkylene; and $R^5$ is H. In some embodiments, $L^2$ is *-$L^{4C}$-N($R^5$)-$L^{4D}$-**, wherein $L^{4C}$ is $C_1$-$C_3$ alkylene; $L^{4D}$ is $C_1$-$C_3$ alkylene; and $R^5$ is H. In some embodiments, $L^2$ is

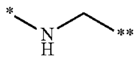 or 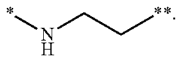.

In some embodiments of a compound of Formula (t), or a variation thereof, $L^2$ is an optionally substituted $C_1$-$C_3$ alkylene. In some embodiments, $L^2$ is a $C_1$-$C_3$ alkylene optionally substituted with oxo, $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, $L^2$ is a $C_1$-$C_3$ alkylene optionally substituted with oxo. In some embodiments, $L^2$ is a $C_1$-$C_3$ alkylene. In some embodiments, $L^2$ is a $C_1$-$C_3$ alkylene substituted with oxo. In some embodiments, $L^2$ is

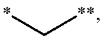, 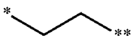, 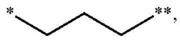, 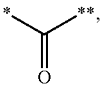, or

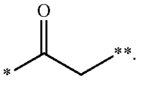.

In some embodiments of a compound of Formula (I), or a variation thereof, $L^2$ is

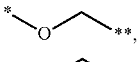, 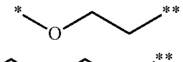, 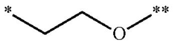,

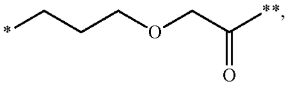, 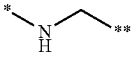,

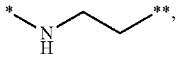, 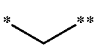, 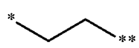,

-continued

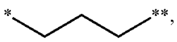, 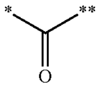, 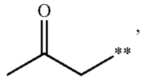, or absent. In some embodiments, $L^2$ is

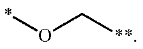

In some embodiments, $L^2$ is

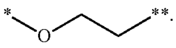

In some embodiments, $L^2$ is

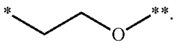

In some embodiments, $L^2$ is

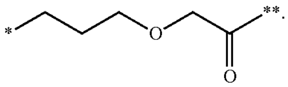

In some embodiments, $L^2$ is

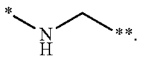

In some embodiments, $L^2$ is

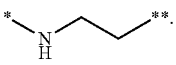

In some embodiments, $L^2$ is

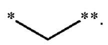

In some embodiments, $L^2$ is

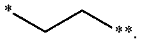

In some embodiments, $L^2$ is

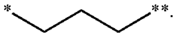

In some embodiments, $L^2$ is

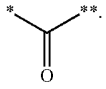

In some embodiments, $L^2$ is

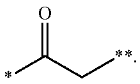

In some embodiments, $L^2$ is absent.

In some embodiments of a compound of Formula (I), or a variation thereof, $L^1$ is an optionally substituted $C_1$-$C_5$ alkylene; U is an optionally substituted 4-8 membered heterocyclyl; and. $L^2$ is an optionally substituted $C_3$-$C_3$ alkylene. In some embodiments, $L^1$ is a $C_1$-$C_5$ alkylene, U is a 4- to 8-membered heterocyclyl, and $L^2$ is a $C_1$-$C_3$ alkylene, wherein the $C_1$-$C_5$ alkylene of $L^1$, the 4- to 8-membered heterocyclyl of U, and the $C_1$-$C_3$ alkylene of $L^2$ are each optionally substituted with oxo, $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, $L^1$ is a $C_1$-$C_5$ alkylene, U is a 4- to 8-membered heterocyclyl, and $L^2$ is a $C_1$-$C_3$ alkylene, wherein the $C_1$-$C_5$ alkylene of $L^1$, the 4- to 8-membered heterocyclyl of U, and the $C_1$-$C_3$ alkylene of Care each optionally substituted with oxo. In some embodiments, $L^1$ is a $C_1$-$C_5$ alkylene, U is

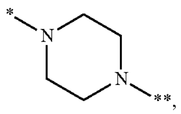

and $L^2$ is a $C_1$-$C_3$ alkylene. In some embodiments, $L^1$ is a $C_1$-$C_5$ alkylene, U is

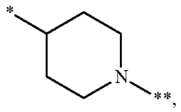

and $L^2$ is a $C_1$-$C_3$ alkylene.

In some embodiments of a compound of Formula (I), or a variation thereof, $L^1$ is an optionally substituted $C_1$-$C_5$ alkylene; U is —N($R^4$)—; and $L^2$ is *-$L^{4A}$-O-$L^{4B}$-**, wherein $L^{4A}$ and $L^{4B}$ are each independently optionally substituted $C_1$-$C_3$ alkylene or absent. In some embodiments, $L^1$ is a $C_1$-$C_5$ alkylene; U is —N($R^4$)—, and $L^2$ is *-$L^{4A}$-O-$L^{4B}$-**, wherein $L^{4A}$ and $L^{4B}$ are each independently $C_1$-$C_3$ alkylene or absent, wherein the $C_1$-$C_5$ alkylene of $L^1$ and the $C_1$-$C_3$ alkylene of $L^{4A}$ and $L^{4B}$ are each independently substituted with oxo, $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, $L^1$ is a $C_1$-$C_5$ alkylene, U is —N($R^4$)—, and $L^2$ is *-$L^{4A}$-O-$L^{4B}$-**, wherein $L^{4A}$ and $L^{4B}$ are each independently $C_1$-$C_3$ alkylene or absent, wherein the $C_1$-$C_5$ alkylene of $L^1$ and the $C_1$-$C_3$ alkylene of $L^{4A}$ and $L^{4B}$ are each independently optionally substituted with oxo. In some embodiments, $L^1$ is a $C_1$-$C_5$ alkylene, U is —N($R^4$)—, and $L^2$ is *-$L^{4A}$-O-$L^{4B}$-**, wherein $L^{4A}$ is a $C_1$-$C_3$ alkylene and $L^{4B}$ is a $C_1$-$C_3$ alkylene substituted with oxo.

In some embodiments, $L^1$ is an optionally substituted $C_1$-$C_5$ alkylene, U is —NH—, and $L^2$ is an optionally substituted $C_1$-$C_2$ alkylene. In some embodiments, $L^1$ is $C_1$-$C_5$ alkylene, U is —NH—, and $L^2$ is a $C_1$-$C_3$ alkylene, wherein the $C_1$-$C_5$ alkylene of $L^1$ and the $C_1$-$C_3$ alkylene of $L^2$ are each optionally substituted with oxo, $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, $L^1$ is a $C_1$-$C_5$ alkylene, U is —NH—, and $L^2$ is a $C_1$-$C_3$ alkylene, wherein the $C_1$-$C_5$ alkylene of $L^1$ and the $C_1$-$C_3$ alkylene of $L^2$ are each optionally substituted with oxo. In some embodiments, $L^1$ is a $C_1$-$C_5$ alkylene, U is —NH—, and $L^2$ is a $C_1$-$C_3$ alkylene, wherein the $C_1$-$C_5$ alkylene of $L^1$ and the $C_1$-$C_3$ alkylene of $L^2$ are each optionally substituted with oxo.

In some embodiments, $L^1$ is an optionally substituted $C_1$-$C_5$ alkylene, U is —O—, and $L^2$ is an optionally substituted $C_1$-$C_3$ alkylene. In some embodiments, $L^1$ is a $C_1$-$C_5$ alkylene, U is —O—,and is a $C_1$-$C_3$ alkylene, wherein the $C_1$-$C_5$ alkylene of $L^1$ and the $C_1$-$C_3$ alkylene of $L^2$ are each optionally substituted with oxo, $C_{1-6}$ alkyl, $C_{2-6}$ alkenyl, $C_{2-6}$ alkynyl, halo, —CN, —OH, —$NH_2$, $C_{3-12}$ cycloalkyl, 3- to 12-membered heterocyclyl, 5- to 10-membered heteroaryl, or $C_6$-$C_{14}$ aryl. In some embodiments, $L^1$ is a $C_1$-$C_5$ alkylene, U is —O—, and $L^2$ is a $C_1$-$C_3$ alkylene, wherein the $C_1$-$C_5$ alkylene al) and the $C_1$-$C_3$ alkylene of $L^2$ are each optionally substituted with oxo. In some embodiments, $L^1$ is a $C_1$-$C_5$ alkylene, U is —O—, and $L^2$ is a $C_1$-$C_3$ alkylene, wherein the $C_1$-$C_5$ alkylene of $L^1$ and the $C_1$-$C_3$ alkylene of $L^2$ are each optionally substituted with oxo. In some embodiments, $L^1$ is a $C_1$-$C_5$ alkylene, U is —O—, and $L^2$ is absent.

In some embodiments, a compound of Formula (I) is a compound of any one of Formula (I-7)-(I-10), (II-7)-(II-10), and (III-7)-(III-10) or a pharmaceutically acceptable salt thereof. In some embodiments, a compound of Formula (I) is a compound of Formula (I-7). In some embodiments, a compound of Formula (I) is a compound of Formula (I-8). In some embodiments, a compound of Formula (I) is a compound of Formula (I-9). In some embodiments, a compound of Formula (I) is a compound of Formula (I-10). In some embodiments, a compound of Formula (I) is a compound of Formula (II-7). In some embodiments, a compound of Formula (I) is a compound of Formula (II-8). In some embodiments, a compound of Formula (I) is a compound of Formula (II-9). In some embodiments, a compound of Formula (I) is a compound of Formula (II-10). In some embodiments, a compound of Formula (I) is a compound of Formula (III-7). In some embodiments, a compound of Formula (I) is a compound of Formula (III-8). In some embodiments, a compound of Formula (I) is a compound of Formula (III-9). In some embodiments, a compound of Formula (I) is a compound of Formula (III-10). Such formulae are of the following structures:

(I-7)

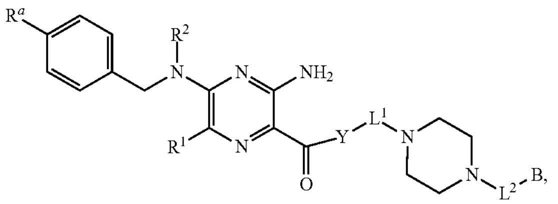

(II-7)

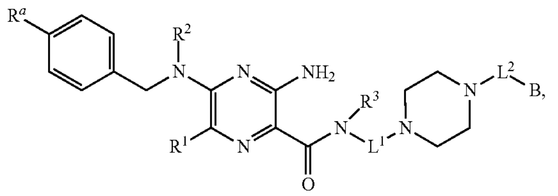

(III-7)

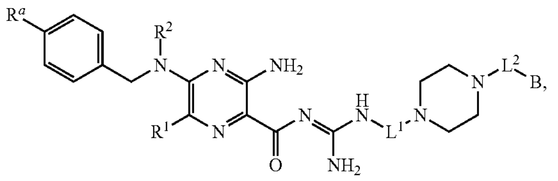

(I-8)

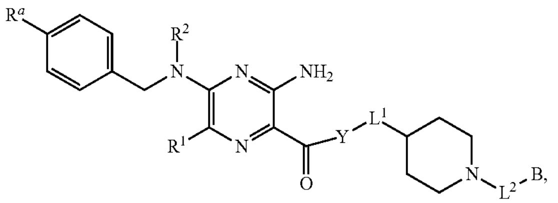

(II-8)

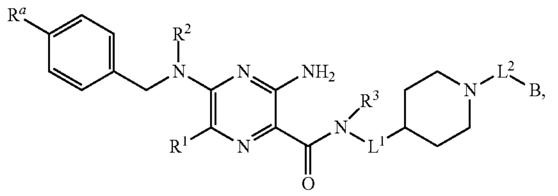

(III-8)

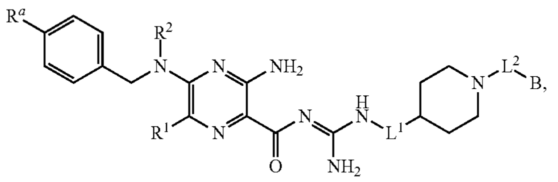

(I-9)

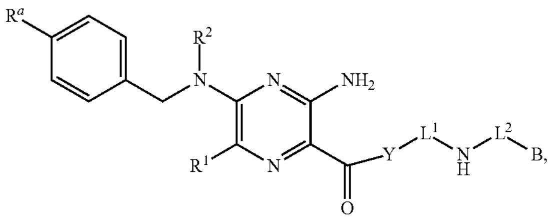

-continued (II-9)

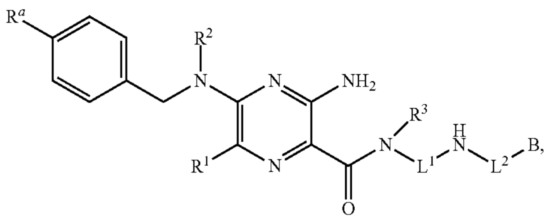

(III-9)

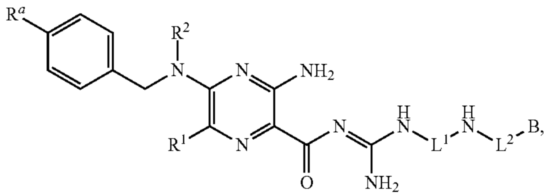

(I-10)

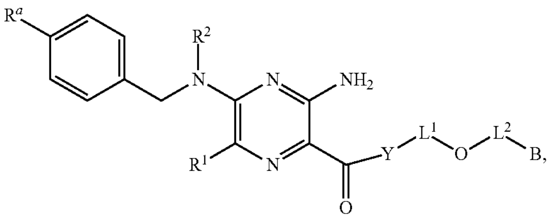

(II-10)

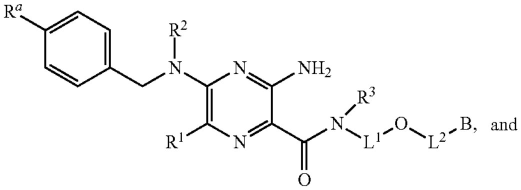

and (III-10)

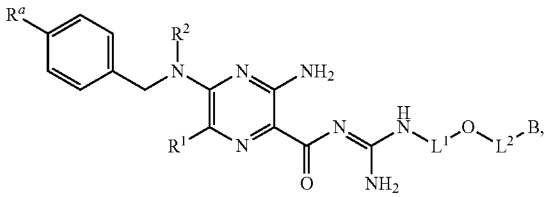

wherein $R^1$, $R^2$, $R^3$, Y, $L^1$, $L^2$, and B are as detailed herein for Formula (I) and $R^a$ is H or halo.

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to A of Formula (I) may be combined with every description, variation, embodiment or aspect of B, Y, U, $L^1$, $L^2$, $R^1$, and $R^2$ the same as if each and every combination were specifically and individually listed. It is also understood that all descriptions, variations, embodiments or aspects of Formula (I), where applicable, apply equally to other formulae detailed herein, and are equally described, the same as if each and every description, variation, embodiment or aspect were separately and individually listed for all formulae. For example, it is understood that, all descriptions, variations, embodiments or aspects of Formula (I), where applicable, apply equally to any of related formulae as detailed herein, such as Formulae (I-1)-(I-10), (II), (II-1)-(II-10), (III), and (III-1)-(III-10), and are equally described, the same as if each and every description, variation, embodiment or aspect were separately and individually listed for all formulae. For example, in some embodiments of a compound of Formula (I) or a variation thereof, $R^1$ is halo; $R^2$ is H; $R^3$ is H; A is a phenyl substituted with 1-5 halo which may be the same or different; U is 4- to 8-membered heterocyclyl or —O—; and B is a phenyl optionally substituted with 1-5 halo which may be the same or different. As another example, in some embodiments of a compound of Formula (I) or a variation thereof, $R^1$ is halo; $R^2$ is H; $R^3$ is H; A is a phenyl substituted with 1-5 halo which may be the same or different; U is 4- to 8-membered heterocyclyl; and B is a phenyl optionally substituted with 1-5 halo which may be the same or different.

Also provided are salts of compounds referred to herein, such as pharmaceutically acceptable salts. The invention also includes any or all of the stereochemical forms, including any enantiomeric or diastereomeric forms, and any tautomers or other forms of the compounds described. In some embodiments, an isomer of a compound detained herein is a stereoisomer.

A compound as detailed herein may in one aspect be in a purified form and compositions comprising a compound in purified forms are detailed herein. Compositions comprising a compound as detailed herein or a pharmaceutically acceptable salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, I% or 0.5% impurity.

Representative compounds are listed in Table 1.

TABLE 1
| Compound No. | Structure |
| --- | --- |
| 1 | 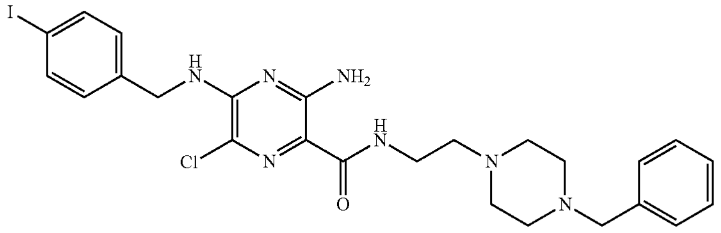 [SMILES: Nc1nc(NCc2ccc(I)cc2)c(Cl)nc1C(=O)NCCN1CCN(Cc2ccccc2)CC1] |
| 2 | 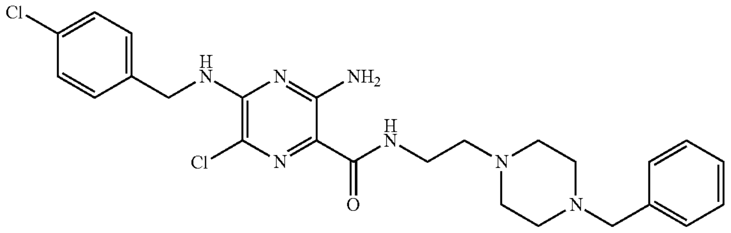 [SMILES: Nc1nc(NCc2ccc(Cl)cc2)c(Cl)nc1C(=O)NCCN1CCN(Cc2ccccc2)CC1] |
| 3 | 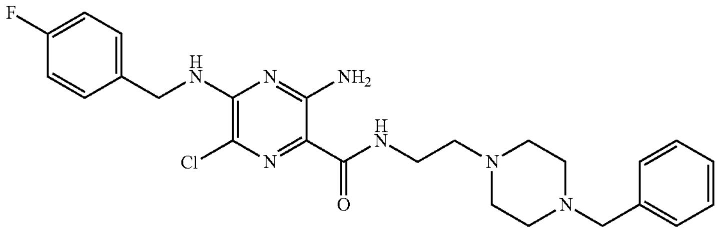 [SMILES: Nc1nc(NCc2ccc(F)cc2)c(Cl)nc1C(=O)NCCN1CCN(Cc2ccccc2)CC1] |
| 4 | 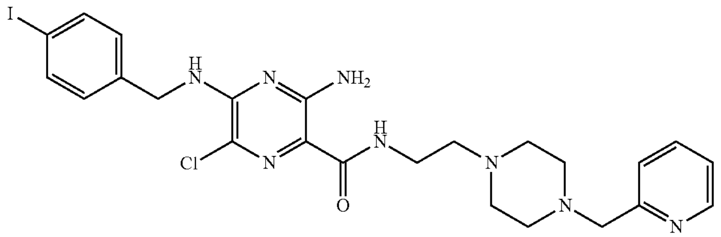 [SMILES: Nc1nc(NCc2ccc(I)cc2)c(Cl)nc1C(=O)NCCN1CCN(Cc2ccccn2)CC1] |
| 5 | 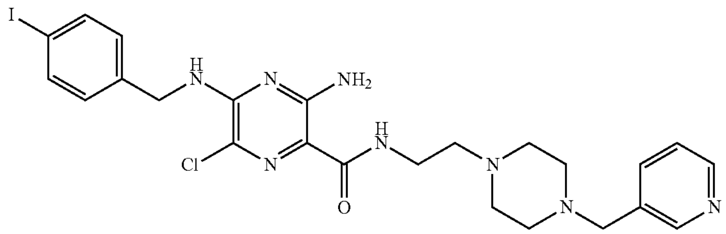 [SMILES: Nc1nc(NCc2ccc(I)cc2)c(Cl)nc1C(=O)NCCN1CCN(Cc2cccnc2)CC1] |
| 6 | 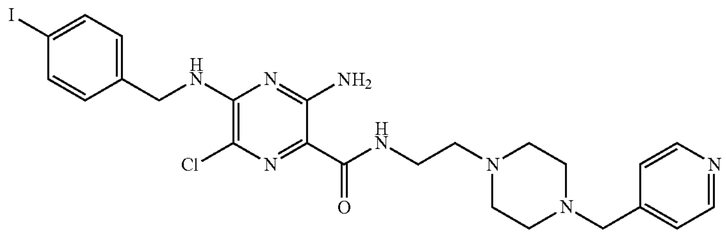 [SMILES: Nc1nc(NCc2ccc(I)cc2)c(Cl)nc1C(=O)NCCN1CCN(Cc2ccncc2)CC1] |

TABLE 1-continued
| Compound No. | Structure |
|---|---|
| 7 | 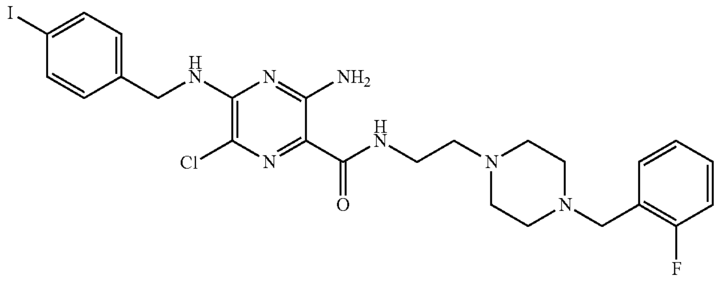 [SMILES: Nc1nc(NCc2ccc(I)cc2)c(Cl)nc1C(=O)NCCN1CCN(Cc2ccccc2F)CC1] |
| 8 | 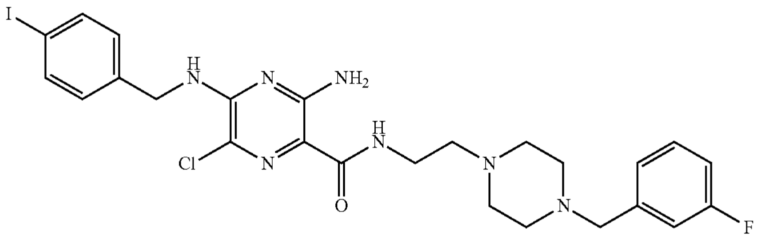 [SMILES: Nc1nc(NCc2ccc(I)cc2)c(Cl)nc1C(=O)NCCN1CCN(Cc2cccc(F)c2)CC1] |
| 9 | 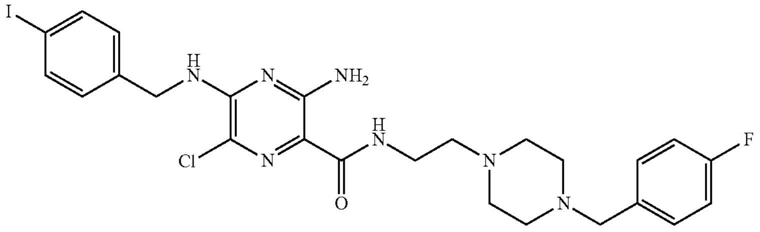 [SMILES: Nc1nc(NCc2ccc(I)cc2)c(Cl)nc1C(=O)NCCN1CCN(Cc2ccc(F)cc2)CC1] |
| 10 | 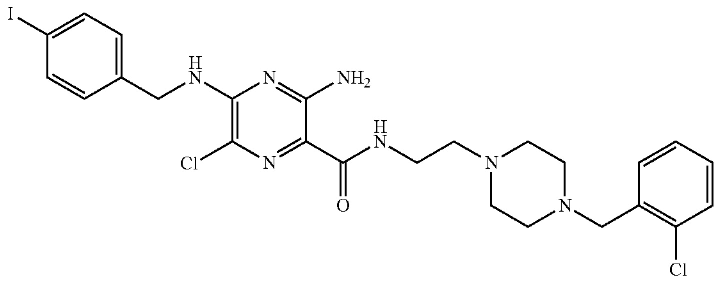 |
| 11 | 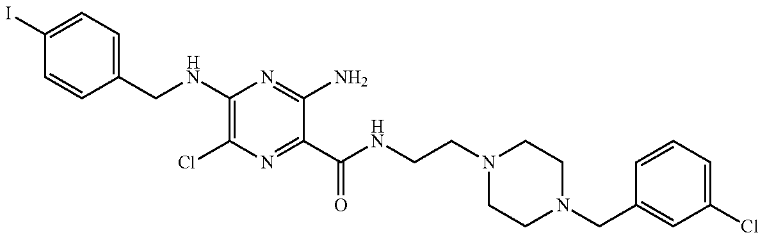 [SMILES: Nc1nc(NCc2ccc(I)cc2)c(Cl)nc1C(=O)NCCN1CCN(Cc2cccc(Cl)c2)CC1] |
| 12 | 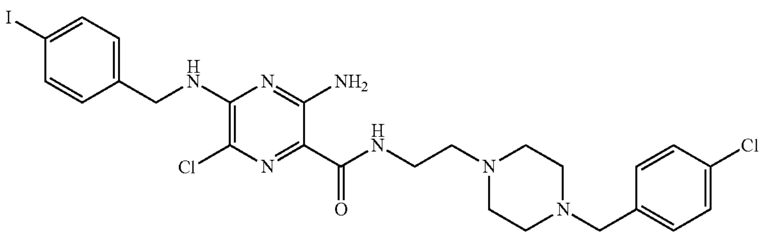 [SMILES: Nc1nc(NCc2ccc(I)cc2)c(Cl)nc1C(=O)NCCN1CCN(Cc2ccc(Cl)cc2)CC1] |

TABLE 1-continued
| Compound No. | Structure |
| --- | --- |
| 13 | 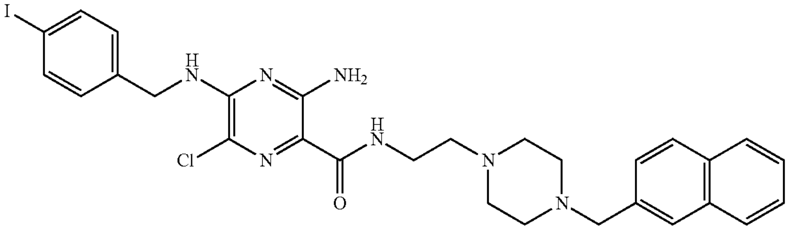 [SMILES: Nc1nc(NCc2ccc(I)cc2)c(Cl)nc1C(=O)NCCN1CCN(Cc2ccc3ccccc3c2)CC1] |
| 14 | 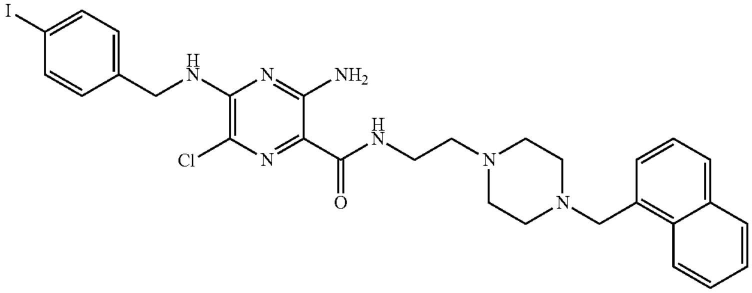 [SMILES: Nc1nc(NCc2ccc(I)cc2)c(Cl)nc1C(=O)NCCN1CCN(Cc2cccc3ccccc23)CC1] |
| 15 | 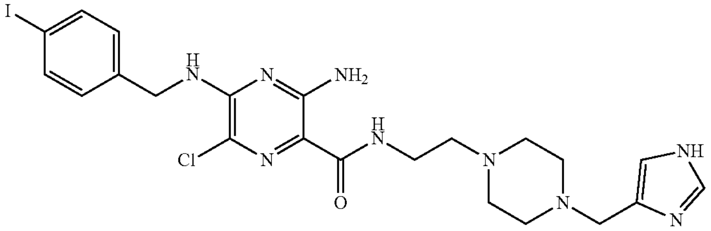 [SMILES: Nc1nc(NCc2ccc(I)cc2)c(Cl)nc1C(=O)NCCN1CCN(Cc2c[nH]cn2)CC1] |
| 16 | 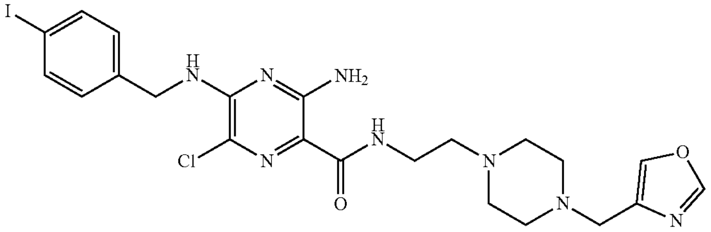 [SMILES: Nc1nc(NCc2ccc(I)cc2)c(Cl)nc1C(=O)NCCN1CCN(Cc2cocn2)CC1] |
| 17 | 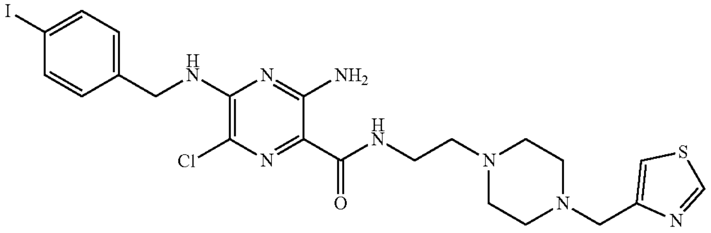 [SMILES: Nc1nc(NCc2ccc(I)cc2)c(Cl)nc1C(=O)NCCN1CCN(Cc2cscn2)CC1] |
| 18 | 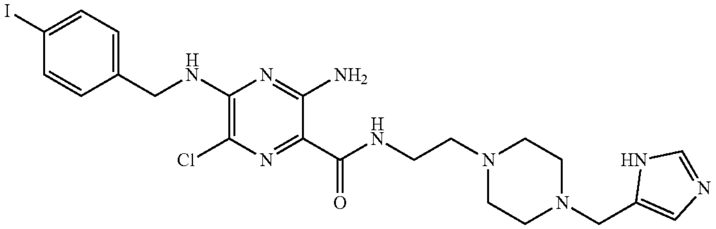 [SMILES: Nc1nc(NCc2ccc(I)cc2)c(Cl)nc1C(=O)NCCN1CCN(Cc2cnc[nH]2)CC1] |

TABLE 1-continued
| Compound No. | Structure |
| --- | --- |
| 19 | 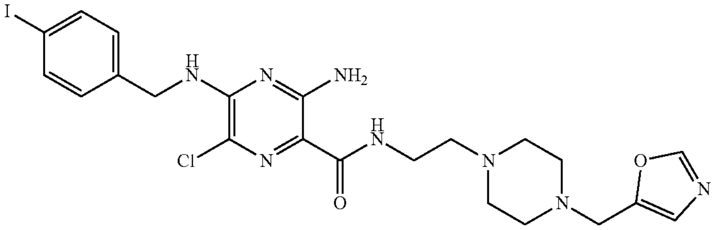 [SMILES: Nc1nc(NCc2ccc(I)cc2)c(Cl)nc1C(=O)NCCN1CCN(Cc2cnco2)CC1] |
| 20 | 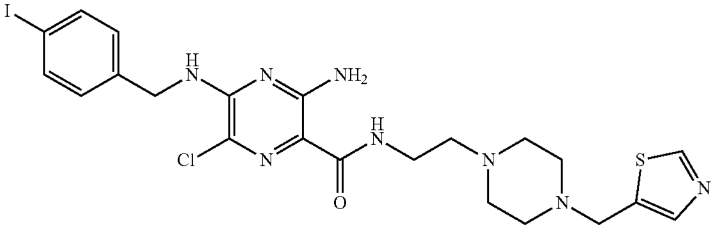 [SMILES: Nc1nc(NCc2ccc(I)cc2)c(Cl)nc1C(=O)NCCN1CCN(Cc2cncs2)CC1] |
| 21 | 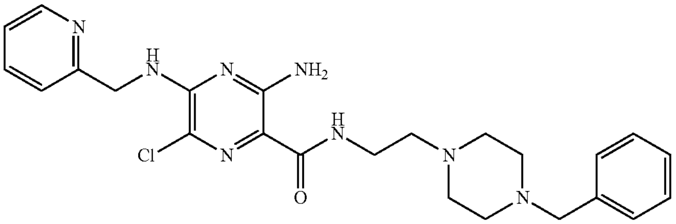 [SMILES: Nc1nc(NCc2ccccn2)c(Cl)nc1C(=O)NCCN1CCN(Cc2ccccc2)CC1] |
| 22 | 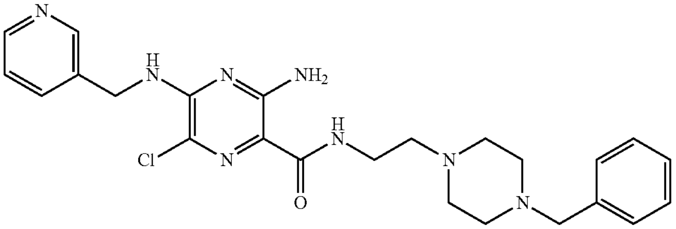 [SMILES: Nc1nc(NCc2cccnc2)c(Cl)nc1C(=O)NCCN1CCN(Cc2ccccc2)CC1] |
| 23 | 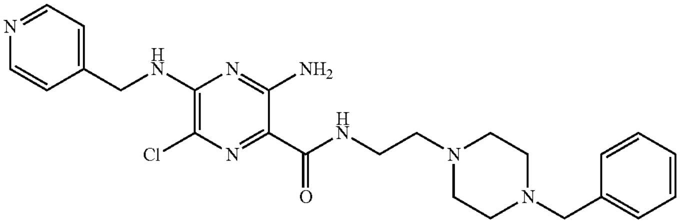 [SMILES: Nc1nc(NCc2ccncc2)c(Cl)nc1C(=O)NCCN1CCN(Cc2ccccc2)CC1] |
| 24 | 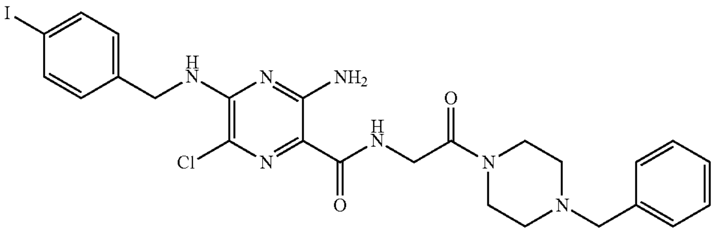 [SMILES: Nc1nc(NCc2ccc(I)cc2)c(Cl)nc1C(=O)NCC(=O)N1CCN(Cc2ccccc2)CC1] |

TABLE 1-continued
| Compound No. | Structure |
| --- | --- |
| 25 | 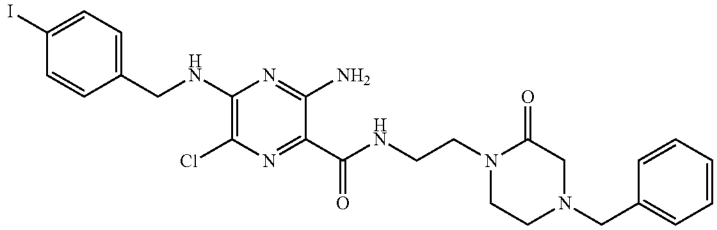 [SMILES: Nc1nc(NCc2ccc(I)cc2)c(Cl)nc1C(=O)NCCN1CCN(Cc2ccccc2)CC1=O] |
| 26 | 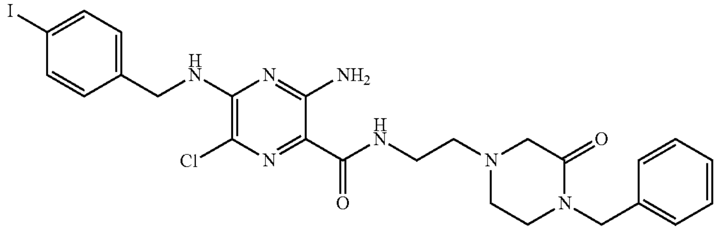 [SMILES: Nc1nc(NCc2ccc(I)cc2)c(Cl)nc1C(=O)NCCN1CCN(Cc2ccccc2)C(=O)C1] |
| 27 | 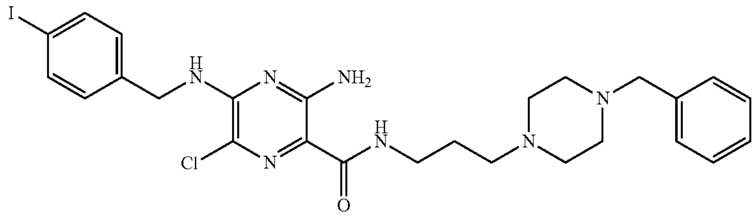 [SMILES: Nc1nc(NCc2ccc(I)cc2)c(Cl)nc1C(=O)NCCCN1CCN(Cc2ccccc2)CC1] |
| 28 | 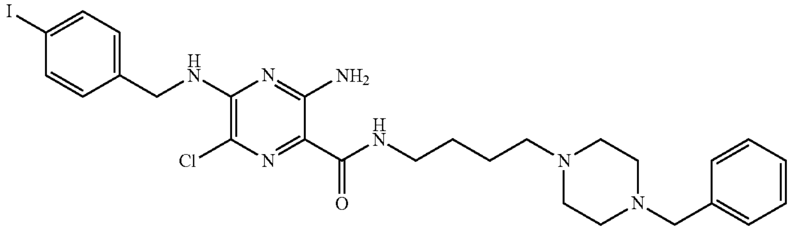 [SMILES: Nc1nc(NCc2ccc(I)cc2)c(Cl)nc1C(=O)NCCCCN1CCN(Cc2ccccc2)CC1] |
| 29 | 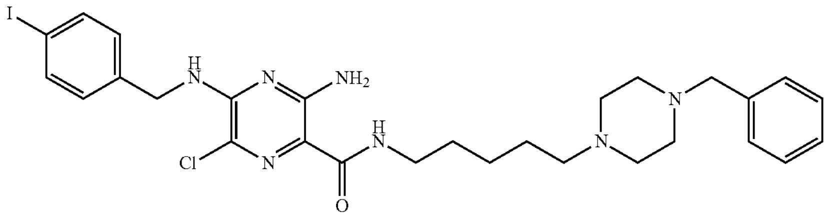 [SMILES: Nc1nc(NCc2ccc(I)cc2)c(Cl)nc1C(=O)NCCCCCN1CCN(Cc2ccccc2)CC1] |
| 30 | 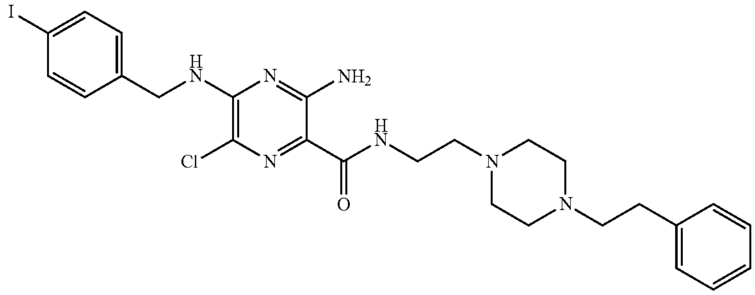 [SMILES: Nc1nc(NCc2ccc(I)cc2)c(Cl)nc1C(=O)NCCN1CCN(CCc2ccccc2)CC1] |

TABLE 1-continued
| Compound No. | Structure |
| --- | --- |
| 31 | 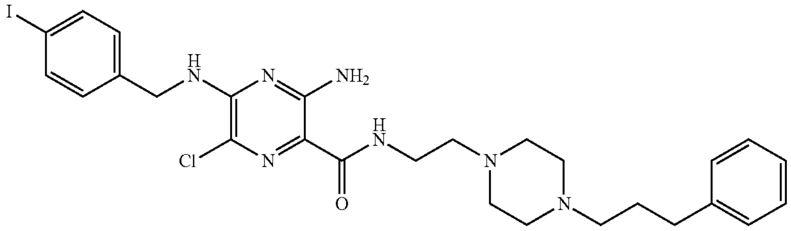 [SMILES: Nc1nc(NCc2ccc(I)cc2)c(Cl)nc1C(=O)NCCN1CCN(CCCc2ccccc2)CC1] |
| 32 | 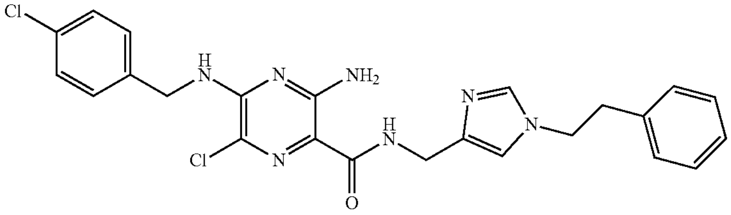 [SMILES: Nc1nc(NCc2ccc(Cl)cc2)c(Cl)nc1C(=O)NCc1cn(CCc2ccccc2)cn1] |
| 33 | 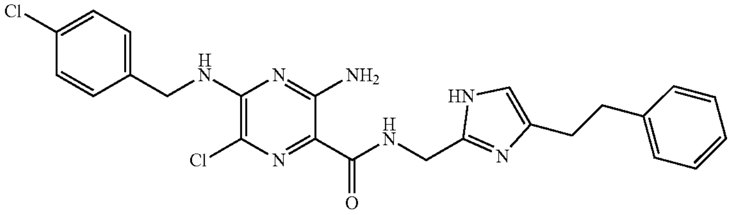 [SMILES: Nc1nc(NCc2ccc(Cl)cc2)c(Cl)nc1C(=O)NCc1nc(CCc2ccccc2)c[nH]1] |
| 34 | 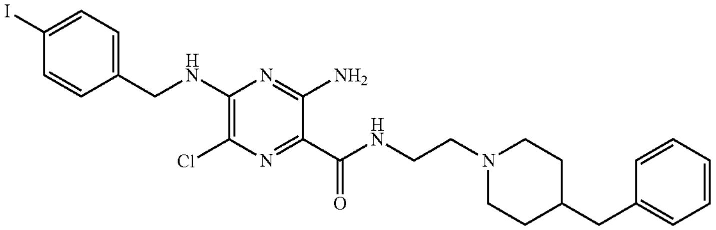 [SMILES: Nc1nc(NCc2ccc(I)cc2)c(Cl)nc1C(=O)NCCN1CCC(Cc2ccccc2)CC1] |
| 35 | 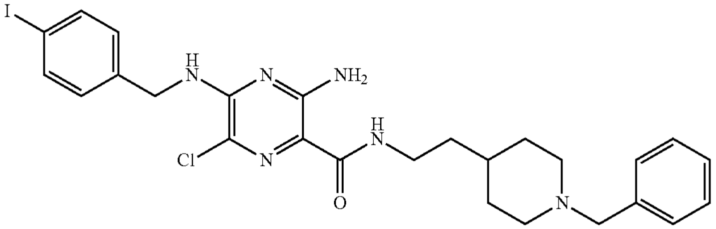 [SMILES: Nc1nc(NCc2ccc(I)cc2)c(Cl)nc1C(=O)NCCC1CCN(Cc2ccccc2)CC1] |
| 36 | 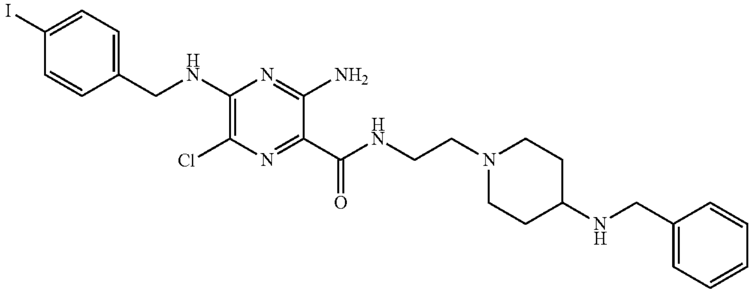 [SMILES: Nc1nc(NCc2ccc(I)cc2)c(Cl)nc1C(=O)NCCN1CCC(NCc2ccccc2)CC1] |

TABLE 1-continued
| Compound No. | Structure |
| --- | --- |
| 37 | 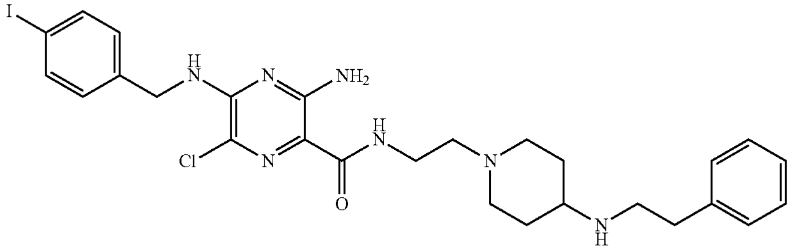 [SMILES: Nc1nc(NCc2ccc(I)cc2)c(Cl)nc1C(=O)NCCN1CCC(NCCc2ccccc2)CC1] |
| 38 | 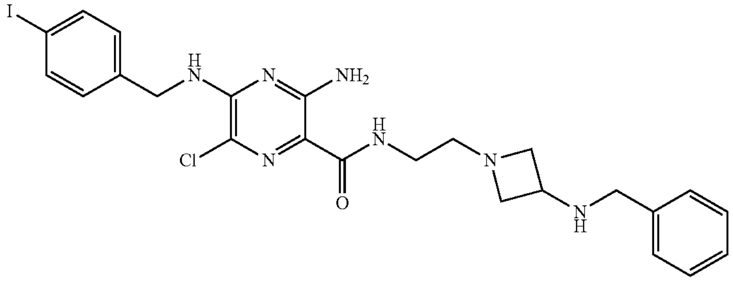 [SMILES: Nc1nc(NCc2ccc(I)cc2)c(Cl)nc1C(=O)NCCN1CC(NCc2ccccc2)C1] |
| 39 | 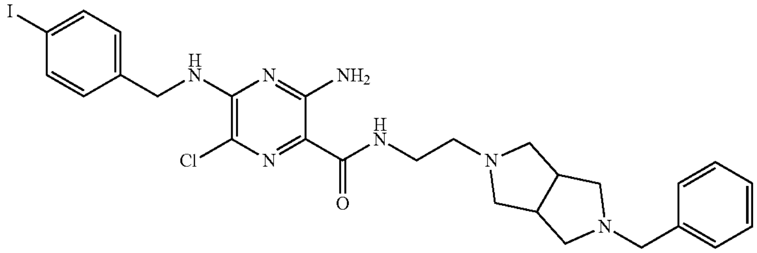 [SMILES: Nc1nc(NCc2ccc(I)cc2)c(Cl)nc1C(=O)NCCN1CC2CN(Cc3ccccc3)CC2C1] |
| 40 | 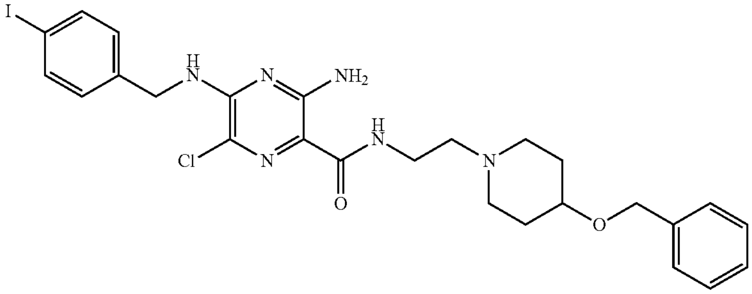 [SMILES: Nc1nc(NCc2ccc(I)cc2)c(Cl)nc1C(=O)NCCN1CCC(OCc2ccccc2)CC1] |
| 41 | 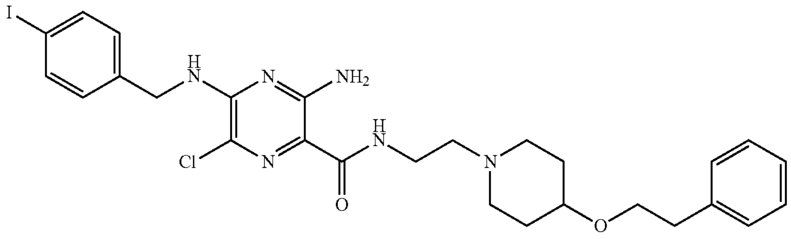 [SMILES: Nc1nc(NCc2ccc(I)cc2)c(Cl)nc1C(=O)NCCN1CCC(OCCc2ccccc2)CC1] |
| 42 | 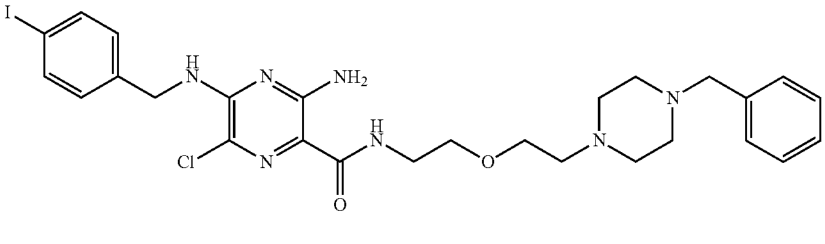 [SMILES: Nc1nc(NCc2ccc(I)cc2)c(Cl)nc1C(=O)NCCOCCN1CCN(Cc2ccccc2)CC1] |

TABLE 1-continued
| Compound No. | Structure |
|---|---|
| 43 | 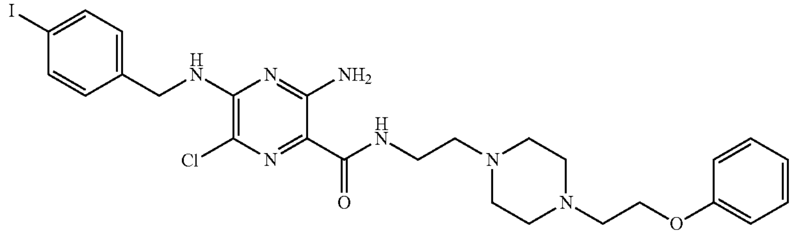 [SMILES: Nc1nc(NCc2ccc(I)cc2)c(Cl)nc1C(=O)NCCN1CCN(CCOc2ccccc2)CC1] |
| 44 | 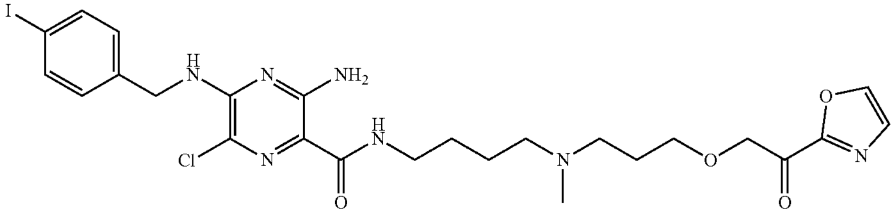 [SMILES: CN(CCCCNC(=O)c1nc(Cl)c(NCc2ccc(I)cc2)nc1N)CCCOCC(=O)c1ncco1] |
| 45 | 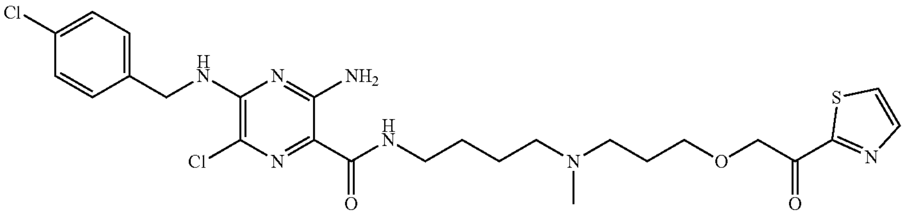 [SMILES: CN(CCCCNC(=O)c1nc(Cl)c(NCc2ccc(Cl)cc2)nc1N)CCCOCC(=O)c1nccs1] |
| 46 | 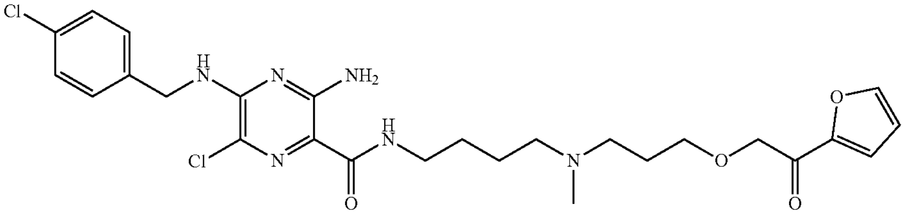 |
| 47 | 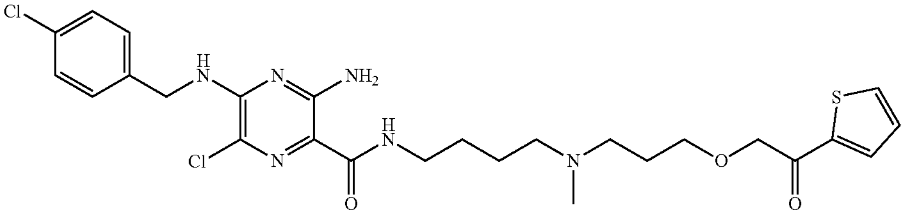 [SMILES: CN(CCCCNC(=O)c1nc(Cl)c(NCc2ccc(Cl)cc2)nc1N)CCCOCC(=O)c1ccco1] |
| 48 | 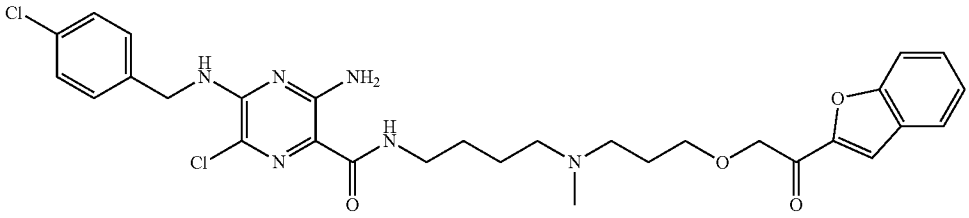 [SMILES: CN(CCCCNC(=O)c1nc(Cl)c(NCc2ccc(Cl)cc2)nc1N)CCCOCC(=O)c1cc2ccccc2o1] |
| 49 | 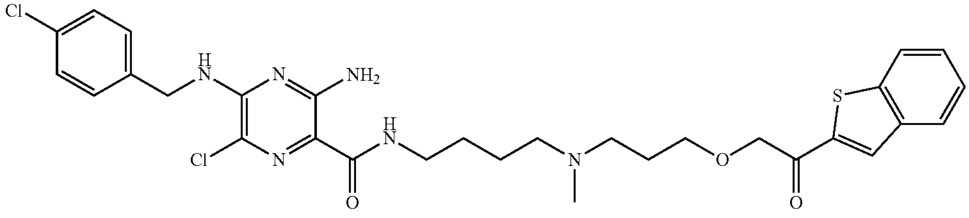 [SMILES: CN(CCCCNC(=O)c1nc(Cl)c(NCc2ccc(Cl)cc2)nc1N)CCCOCC(=O)c1cc2ccccc2s1] |

TABLE 1-continued
| Compound No. | Structure |
| --- | --- |
| 50 | 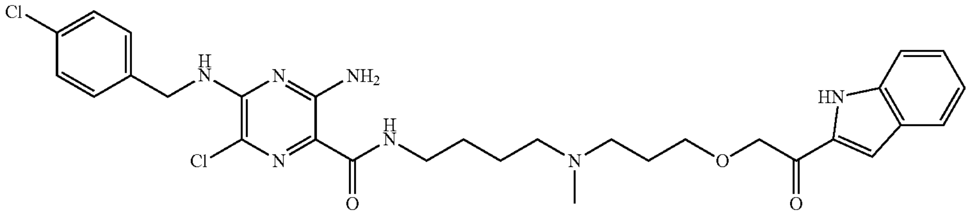 [SMILES: CN(CCCCNC(=O)c1nc(Cl)c(NCc2ccc(Cl)cc2)nc1N)CCCOCC(=O)c1cc2ccccc2[nH]1] |
| 51 | 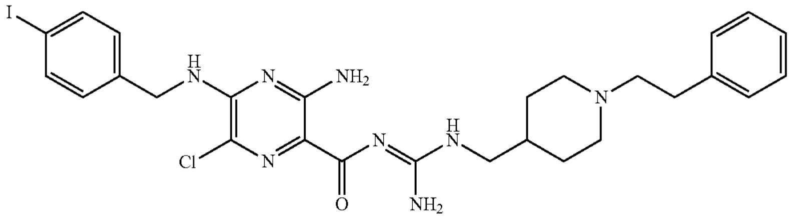 [SMILES: N/C(=N\C(=O)c1nc(Cl)c(NCc2ccc(I)cc2)nc1N)NCC1CCN(CCc2ccccc2)CC1] |
| 52 | 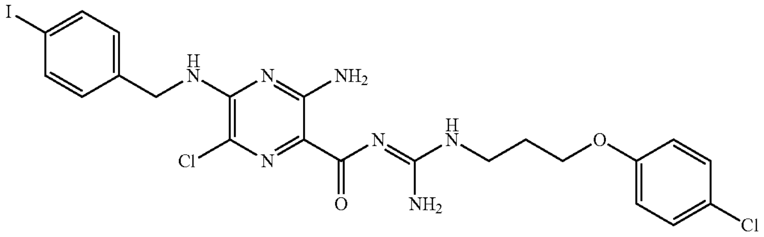 [SMILES: N/C(=N\C(=O)c1nc(Cl)c(NCc2ccc(I)cc2)nc1N)NCCCOc1ccc(Cl)cc1] |
| 53 | 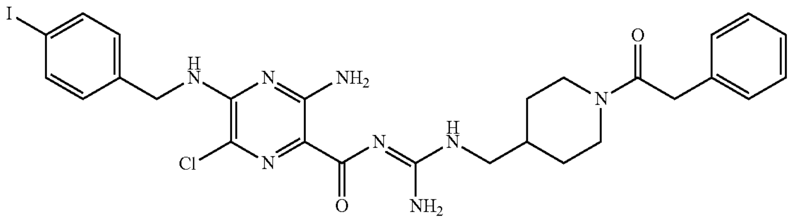 [SMILES: N/C(=N\C(=O)c1nc(Cl)c(NCc2ccc(I)cc2)nc1N)NCC1CCN(C(=O)Cc2ccccc2)CC1] |
| 54 | 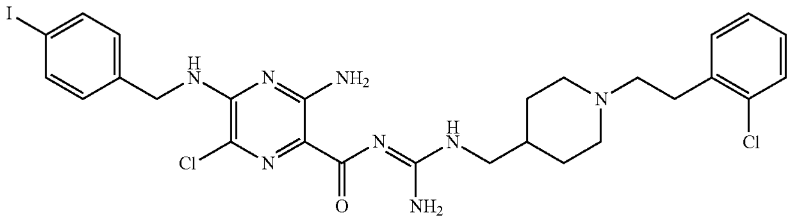 |
| 55 | 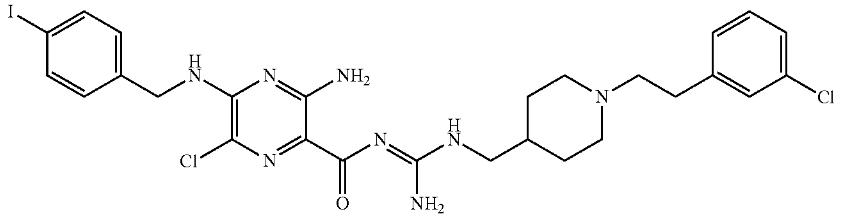 [SMILES: N/C(=N\C(=O)c1nc(Cl)c(NCc2ccc(I)cc2)nc1N)NCC1CCN(CCc2cccc(Cl)c2)CC1] |
| 56 | 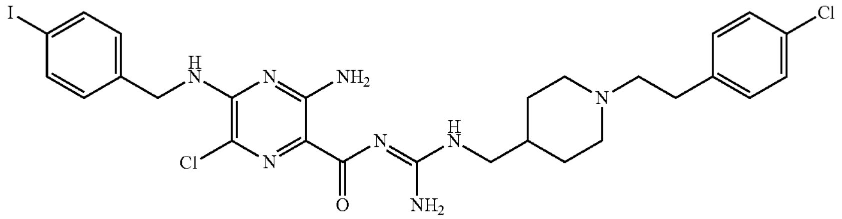 [SMILES: N/C(=N\C(=O)c1nc(Cl)c(NCc2ccc(I)cc2)nc1N)NCC1CCN(CCc2ccc(Cl)cc2)CC1] |

TABLE 1-continued
| Compound No. | Structure |
| --- | --- |
| 57 | 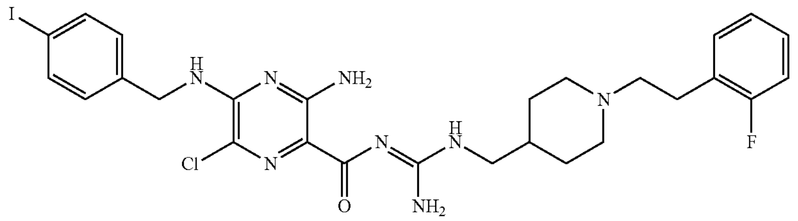 |
| 58 | 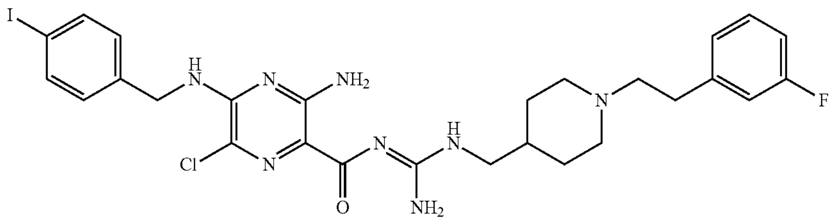 [SMILES: N/C(=N\C(=O)c1nc(Cl)c(NCc2ccc(I)cc2)nc1N)NCC1CCN(CCc2cccc(F)c2)CC1] |
| 59 | 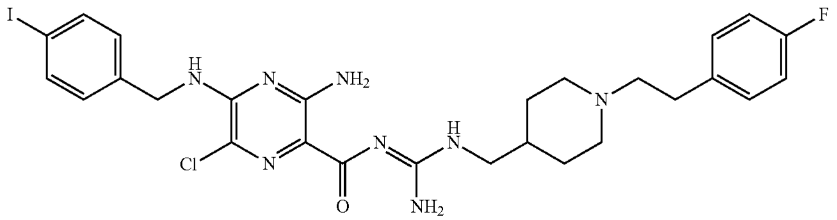 [SMILES: N/C(=N\C(=O)c1nc(Cl)c(NCc2ccc(I)cc2)nc1N)NCC1CCN(CCc2ccc(F)cc2)CC1] |
| 60 | 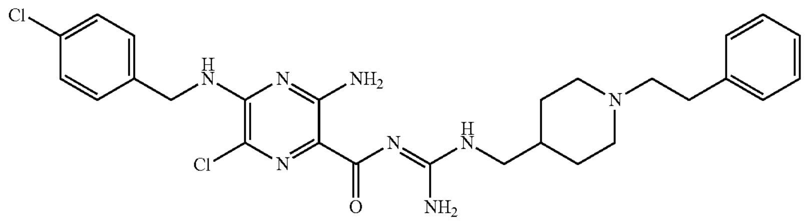 [SMILES: N/C(=N\C(=O)c1nc(Cl)c(NCc2ccc(Cl)cc2)nc1N)NCC1CCN(CCc2ccccc2)CC1] |
| 61 | 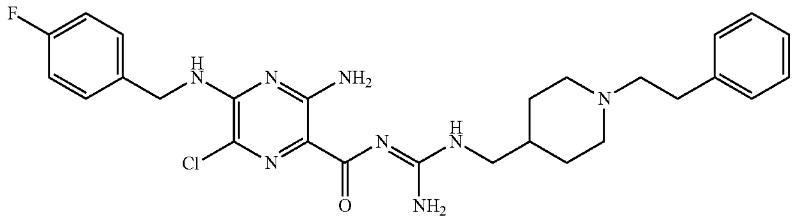 [SMILES: N/C(=N\C(=O)c1nc(Cl)c(NCc2ccc(F)cc2)nc1N)NCC1CCN(CCc2ccccc2)CC1] |
| 62 | 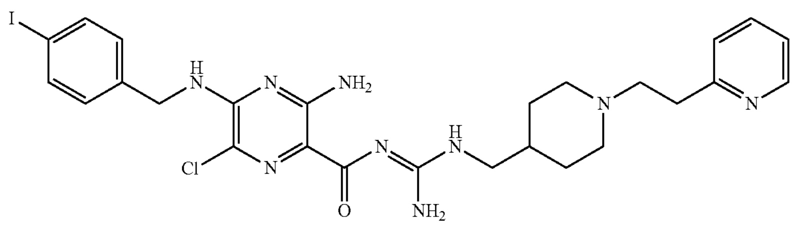 [SMILES: N/C(=N\C(=O)c1nc(Cl)c(NCc2ccc(I)cc2)nc1N)NCC1CCN(CCc2ccccn2)CC1] |

TABLE 1-continued
| Compound No. | Structure |
| --- | --- |
| 63 | 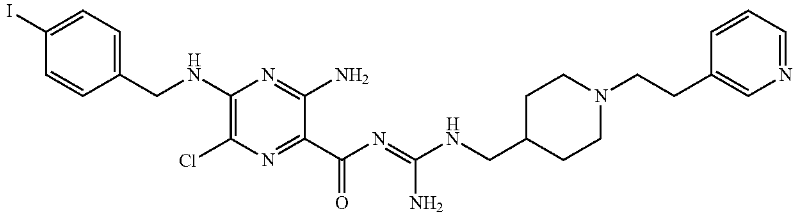 |
| 64 | 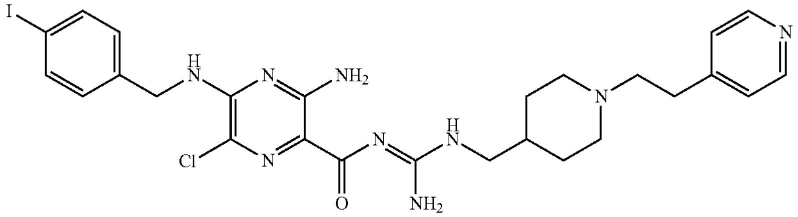 [SMILES: N/C(=N\C(=O)c1nc(Cl)c(NCc2ccc(I)cc2)nc1N)NCC1CCN(CCc2ccncc2)CC1] |
| 65 | 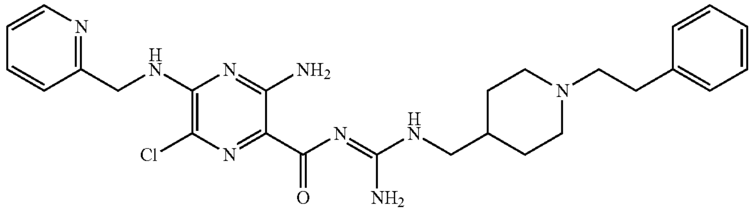 [SMILES: N/C(=N\C(=O)c1nc(Cl)c(NCc2ccccn2)nc1N)NCC1CCN(CCc2ccccc2)CC1] |
| 66 | 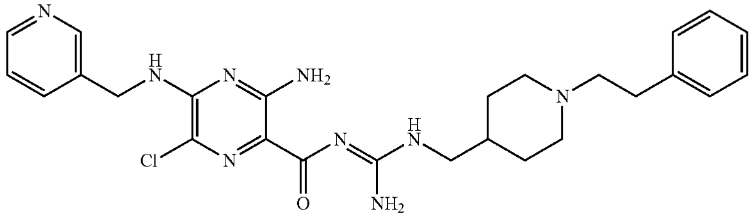 [SMILES: N/C(=N\C(=O)c1nc(Cl)c(NCc2cccnc2)nc1N)NCC1CCN(CCc2ccccc2)CC1] |
| 67 | 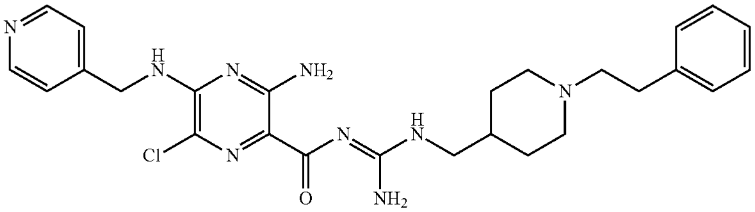 [SMILES: N/C(=N\C(=O)c1nc(Cl)c(NCc2ccncc2)nc1N)NCC1CCN(CCc2ccccc2)CC1] |
| 68 | 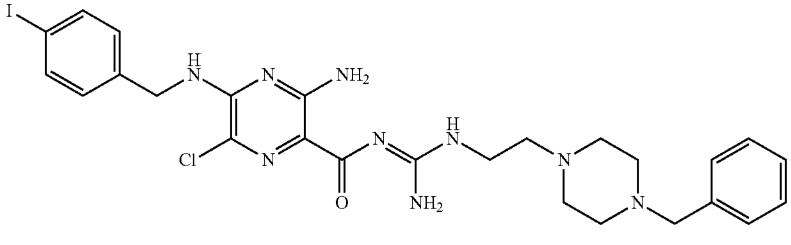 [SMILES: N/C(=N\C(=O)c1nc(Cl)c(NCc2ccc(I)cc2)nc1N)NCCN1CCN(Cc2ccccc2)CC1] |
| 69 | 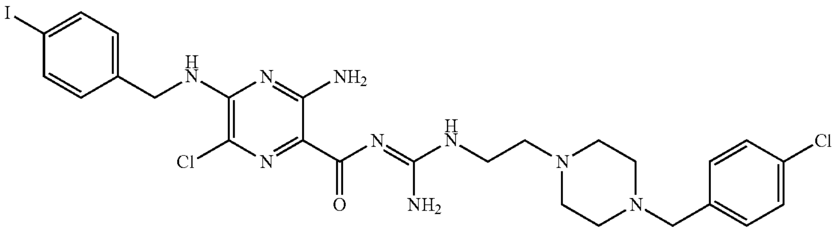 [SMILES: N/C(=N\C(=O)c1nc(Cl)c(NCc2ccc(I)cc2)nc1N)NCCN1CCN(Cc2ccc(Cl)cc2)CC1] |

TABLE 1-continued
| Compound No. | Structure |
| --- | --- |
| 70 | 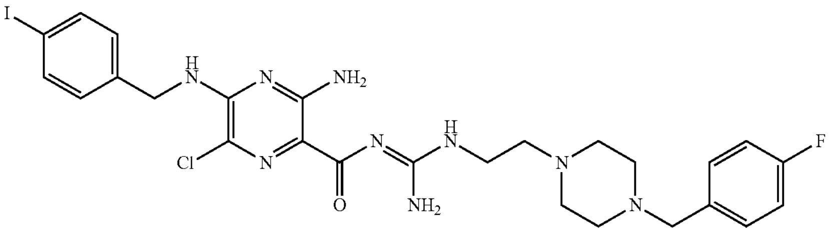 [SMILES: N/C(=N\C(=O)c1nc(Cl)c(NCc2ccc(I)cc2)nc1N)NCCN1CCN(Cc2ccc(F)cc2)CC1] |
| 71 | 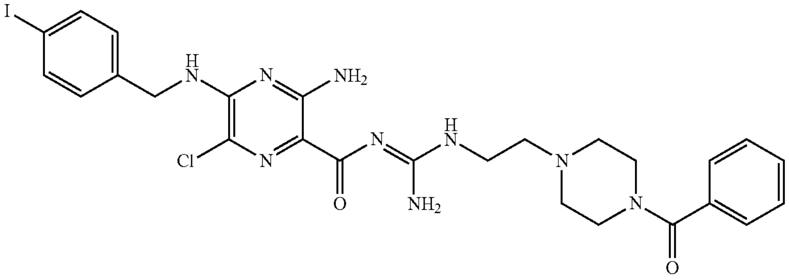 [SMILES: N/C(=N\C(=O)c1nc(Cl)c(NCc2ccc(I)cc2)nc1N)NCCN1CCN(C(=O)c2ccccc2)CC1] |
| 72 | 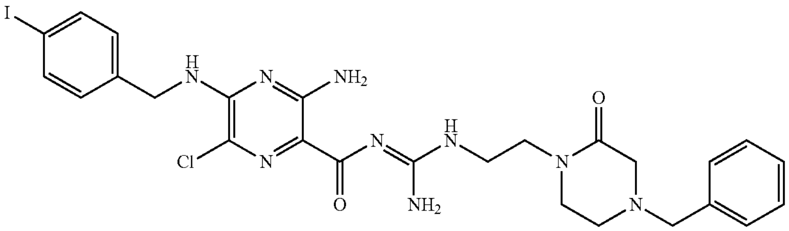 [SMILES: N/C(=N\C(=O)c1nc(Cl)c(NCc2ccc(I)cc2)nc1N)NCCN1CCN(Cc2ccccc2)CC1=O] |
| 73 | 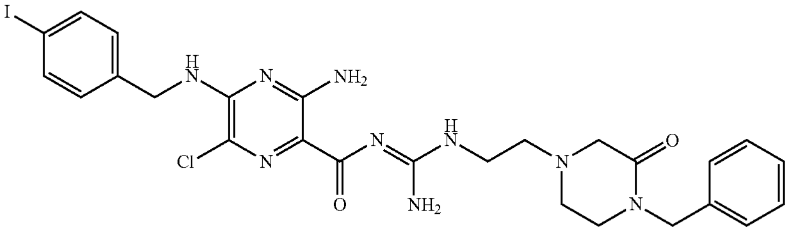 [SMILES: N/C(=N\C(=O)c1nc(Cl)c(NCc2ccc(I)cc2)nc1N)NCCN1CCN(Cc2ccccc2)C(=O)C1] |
| 74 | 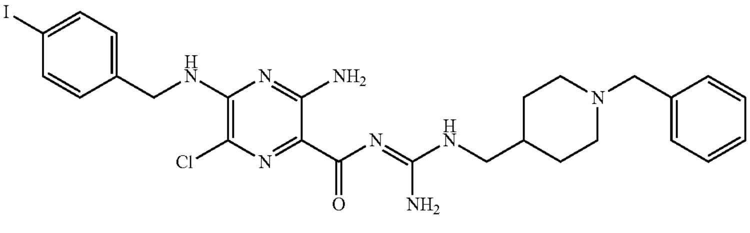 [SMILES: N/C(=N\C(=O)c1nc(Cl)c(NCc2ccc(I)cc2)nc1N)NCC1CCN(Cc2ccccc2)CC1] |
| 75 | 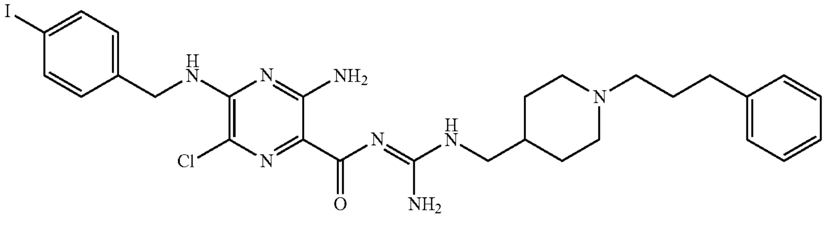 [SMILES: N/C(=N\C(=O)c1nc(Cl)c(NCc2ccc(I)cc2)nc1N)NCC1CCN(CCCc2ccccc2)CC1] |

TABLE 1-continued
| Compound No. | Structure |
| --- | --- |
| 76 | 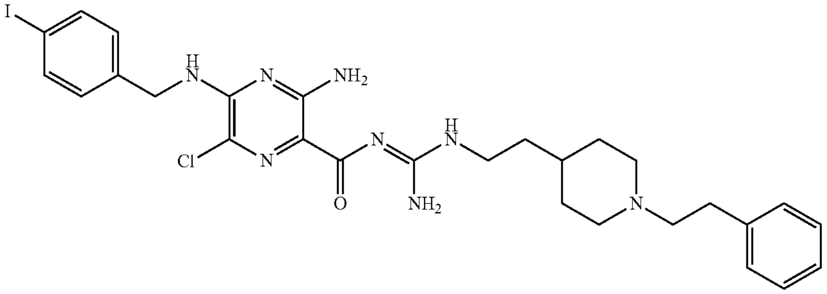 [SMILES: N/C(=N\C(=O)c1nc(Cl)c(NCc2ccc(I)cc2)nc1N)NCCC1CCN(CCc2ccccc2)CC1] |
| 77 | 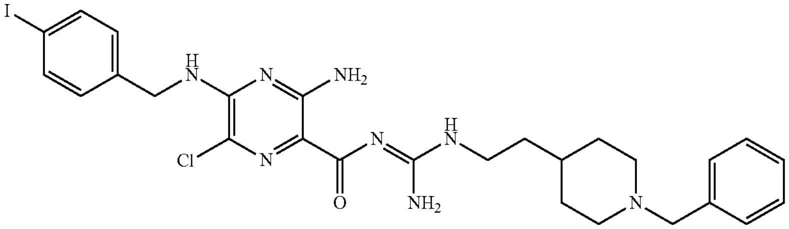 [SMILES: N/C(=N\C(=O)c1nc(Cl)c(NCc2ccc(I)cc2)nc1N)NCCC1CCN(Cc2ccccc2)CC1] |
| 78 | 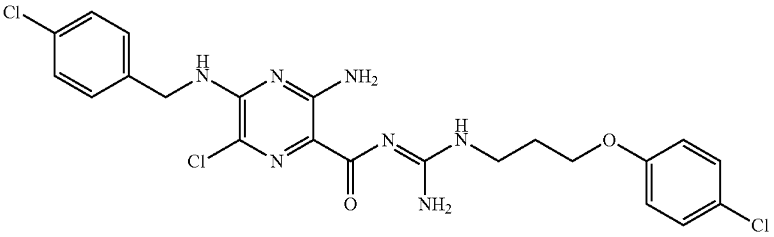 [SMILES: N/C(=N\C(=O)c1nc(Cl)c(NCc2ccc(Cl)cc2)nc1N)NCCCOc1ccc(Cl)cc1] |
| 79 | 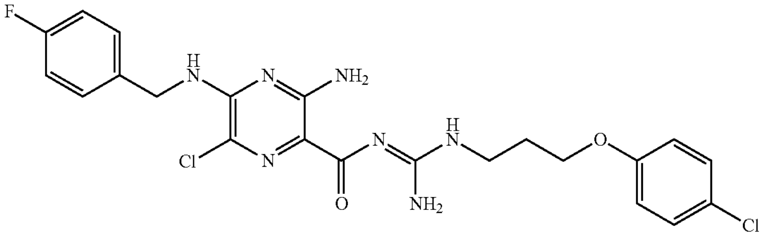 |
| 80 | 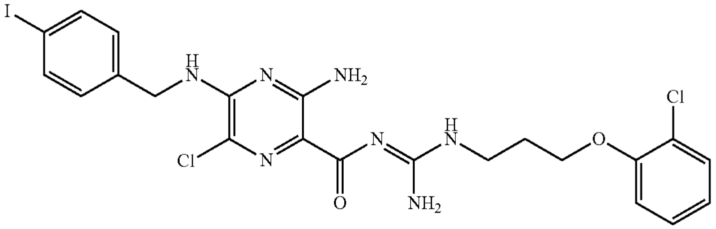 [SMILES: N/C(=N\C(=O)c1nc(Cl)c(NCc2ccc(I)cc2)nc1N)NCCCOc1ccccc1Cl] |
| 81 | 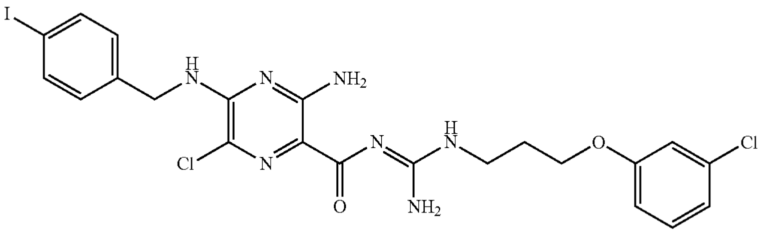 [SMILES: N/C(=N\C(=O)c1nc(Cl)c(NCc2ccc(I)cc2)nc1N)NCCCOc1cccc(Cl)c1] |

TABLE 1-continued
| Compound No. | Structure |
|---|---|
| 82 | 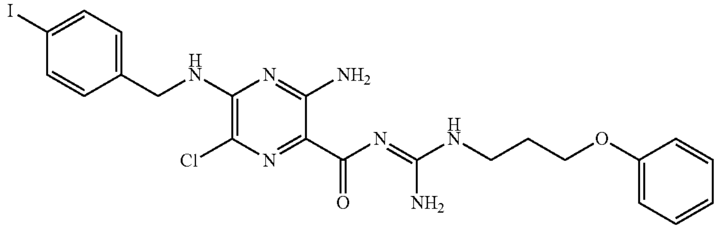 [SMILES: N/C(=N\C(=O)c1nc(Cl)c(NCc2ccc(I)cc2)nc1N)NCCCOc1ccccc1] |
| 83 | 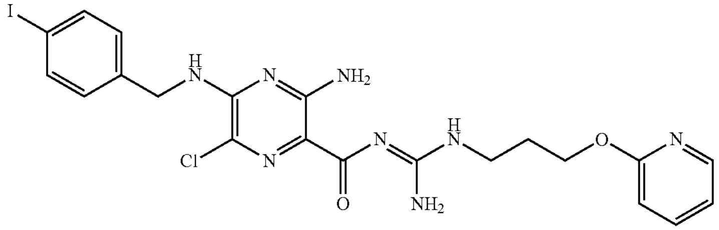 [SMILES: N/C(=N\C(=O)c1nc(Cl)c(NCc2ccc(I)cc2)nc1N)NCCCOc1ccccn1] |
| 84 | 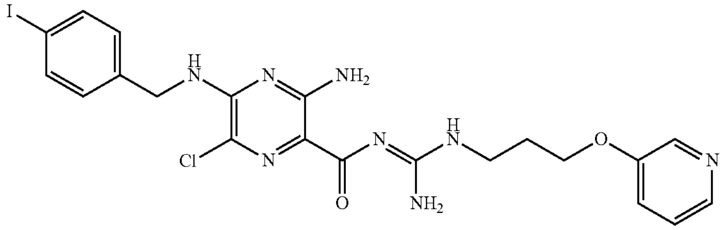 [SMILES: N/C(=N\C(=O)c1nc(Cl)c(NCc2ccc(I)cc2)nc1N)NCCCOc1cccnc1] |
| 85 | 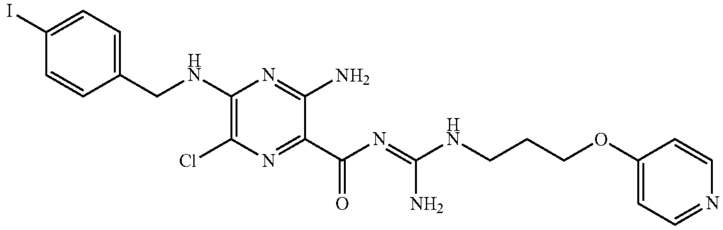 [SMILES: N/C(=N\C(=O)c1nc(Cl)c(NCc2ccc(I)cc2)nc1N)NCCCOc1ccncc1] |
| 86 | 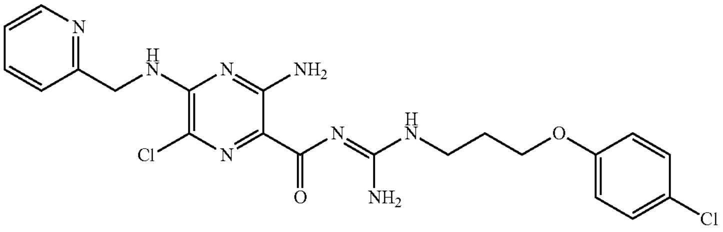 [SMILES: N/C(=N\C(=O)c1nc(Cl)c(NCc2ccccn2)nc1N)NCCCOc1ccc(Cl)cc1] |
| 87 | 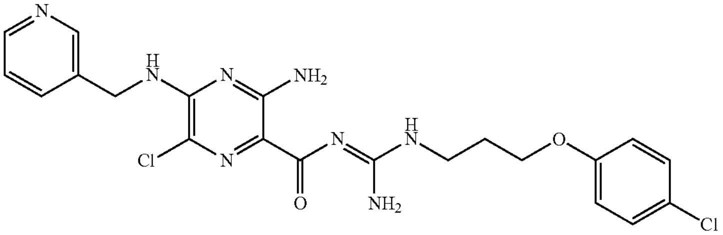 [SMILES: N/C(=N\C(=O)c1nc(Cl)c(NCc2cccnc2)nc1N)NCCCOc1ccc(Cl)cc1] |

TABLE 1-continued
| Compound No. | Structure |
| --- | --- |
| 88 | 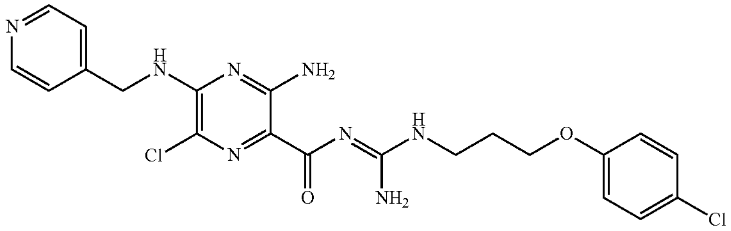 [SMILES: N/C(=N\C(=O)c1nc(Cl)c(NCc2ccncc2)nc1N)NCCCOc1ccc(Cl)cc1] |
| 89 | 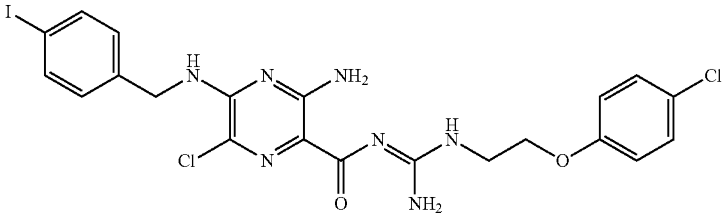 [SMILES: N/C(=N\C(=O)c1nc(Cl)c(NCc2ccc(I)cc2)nc1N)NCCOc1ccc(Cl)cc1] |
| 90 | 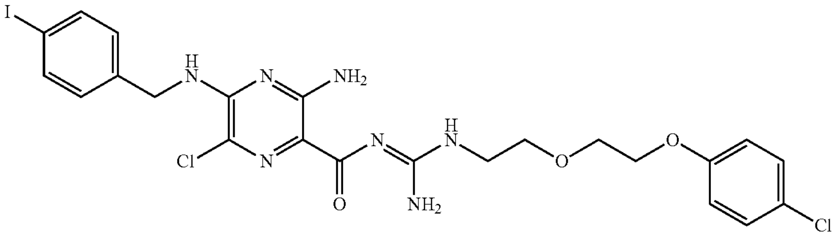 [SMILES: N/C(=N\C(=O)c1nc(Cl)c(NCc2ccc(I)cc2)nc1N)NCCOCCOc1ccc(Cl)cc1] |
| 91 | 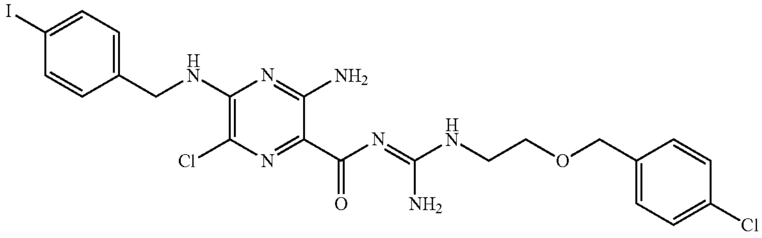 [SMILES: N/C(=N\C(=O)c1nc(Cl)c(NCc2ccc(I)cc2)nc1N)NCCOCc1ccc(Cl)cc1] |
| 92 | 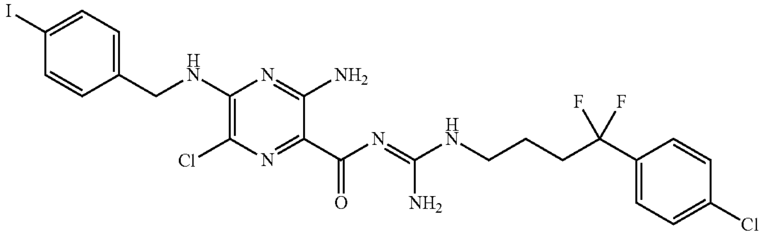 [SMILES: N/C(=N\C(=O)c1nc(Cl)c(NCc2ccc(I)cc2)nc1N)NCCCC(F)(F)c1ccc(Cl)cc1] |
| 93 | 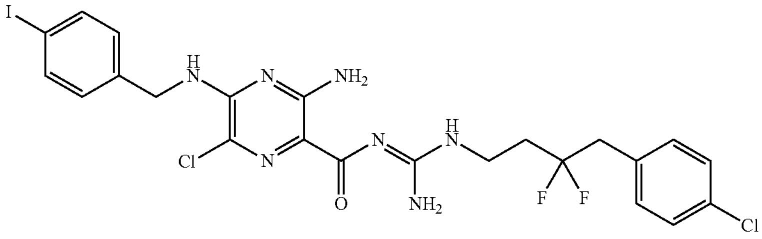 [SMILES: N/C(=N\C(=O)c1nc(Cl)c(NCc2ccc(I)cc2)nc1N)NCCC(F)(F)Cc1ccc(Cl)cc1] |

TABLE 1-continued
| Compound No. | Structure |
| --- | --- |
| 94 | 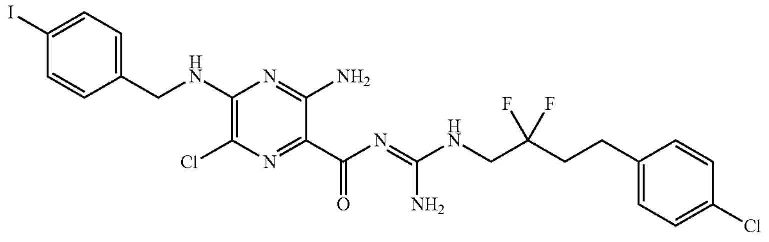 [SMILES: N/C(=N\C(=O)c1nc(Cl)c(NCc2ccc(I)cc2)nc1N)NCC(F)(F)CCc1ccc(Cl)cc1] |
| 95 | 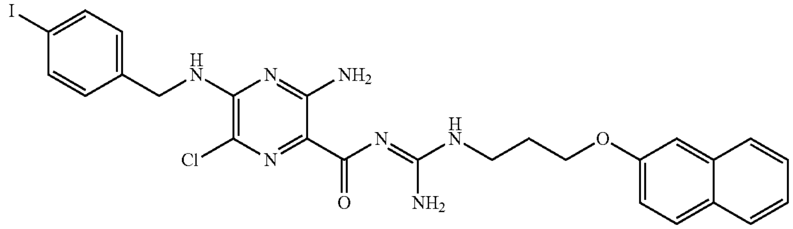 [SMILES: N/C(=N\C(=O)c1nc(Cl)c(NCc2ccc(I)cc2)nc1N)NCCCOc1ccc2ccccc2c1] |
| 96 | 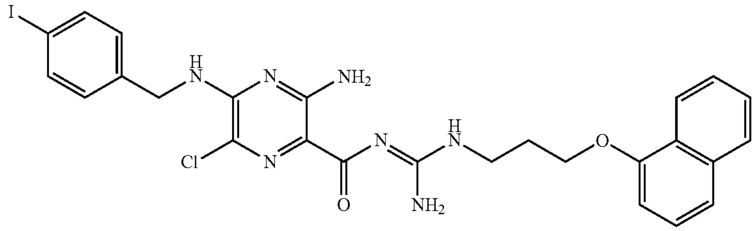 [SMILES: N/C(=N\C(=O)c1nc(Cl)c(NCc2ccc(I)cc2)nc1N)NCCCOc1cccc2ccccc12] |
| 97 | 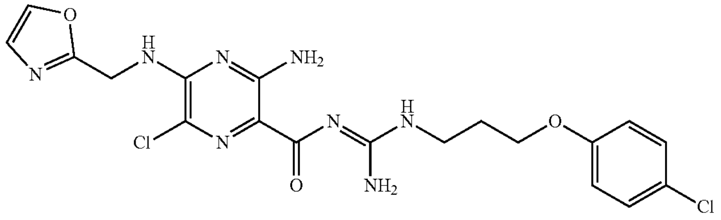 |
| 98 | 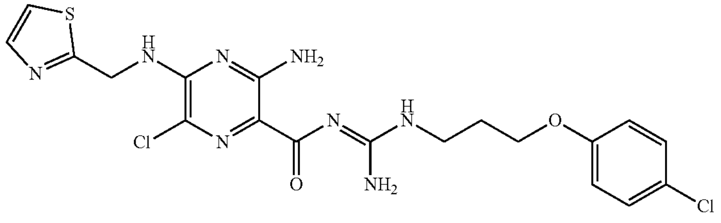 [SMILES: N/C(=N\C(=O)c1nc(Cl)c(NCc2nccs2)nc1N)NCCCOc1ccc(Cl)cc1] |
| 99 | 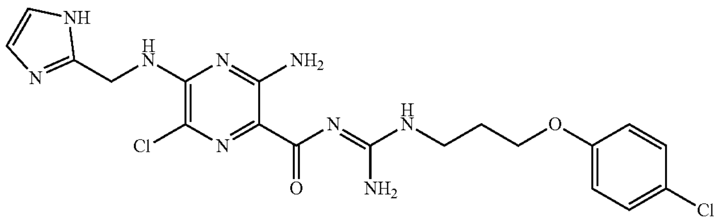 [SMILES: N/C(=N\C(=O)c1nc(Cl)c(NCc2ncc[nH]2)nc1N)NCCCOc1ccc(Cl)cc1] |

TABLE 1-continued
| Compound No. | Structure |
| --- | --- |
| 100 | 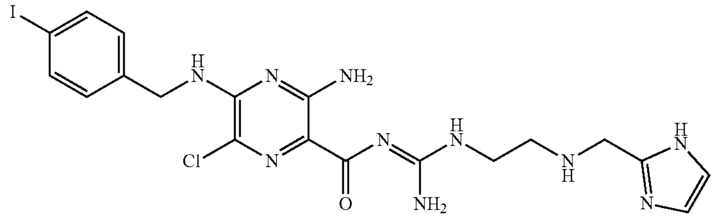 |
| 101 | 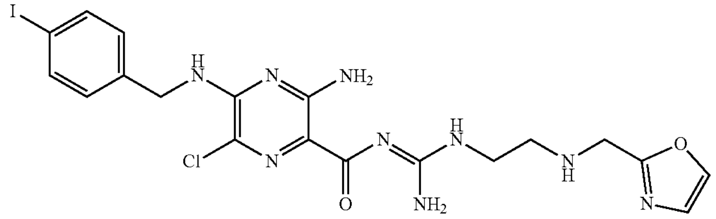 |
| 102 | 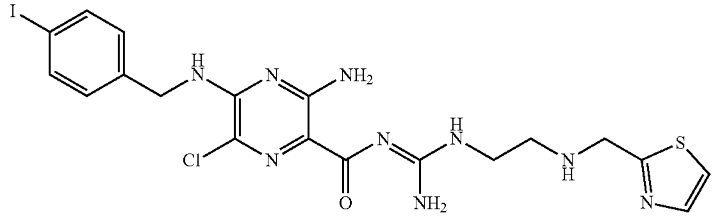 [SMILES: N/C(=N\C(=O)c1nc(Cl)c(NCc2ccc(I)cc2)nc1N)NCCNCc1ncco1] |
| 103 | 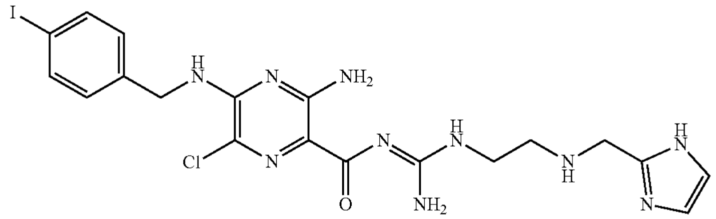 |
| 104 | 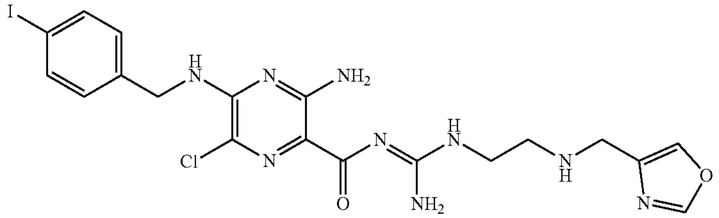 [SMILES: N/C(=N\C(=O)c1nc(Cl)c(NCc2ccc(I)cc2)nc1N)NCCNCc1cocn1] |
| 105 | 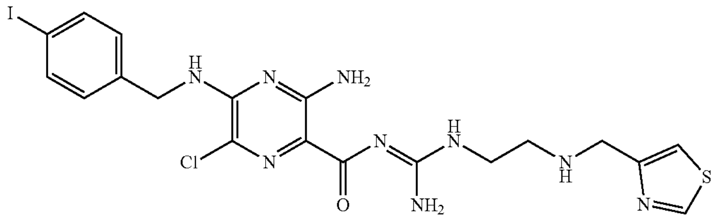 [SMILES: N/C(=N\C(=O)c1nc(Cl)c(NCc2ccc(I)cc2)nc1N)NCCNCc1cscn1] |
| 106 | 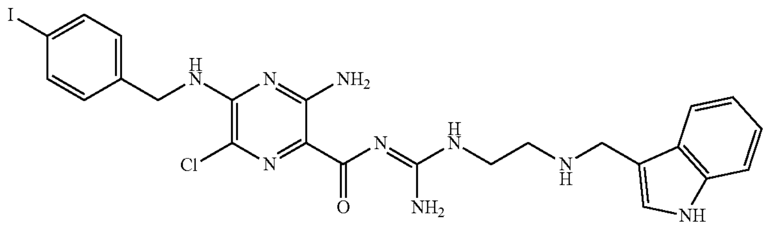 [SMILES: N/C(=N\C(=O)c1nc(Cl)c(NCc2ccc(I)cc2)nc1N)NCCNCc1c[nH]c2ccccc12] |

TABLE 1-continued

| Compound No. | Structure |
| --- | --- |
| 107 | 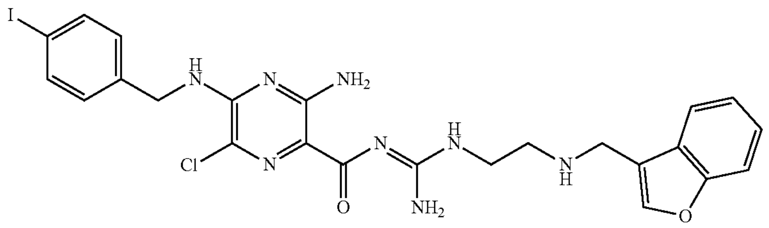 |
| 108 | 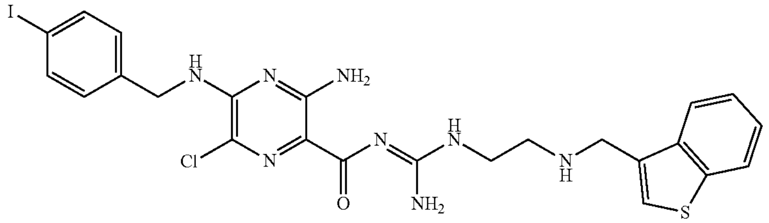 [SMILES: N/C(=N\C(=O)c1nc(Cl)c(NCc2ccc(I)cc2)nc1N)NCCNCc1csc2ccccc12] |
| 109 | 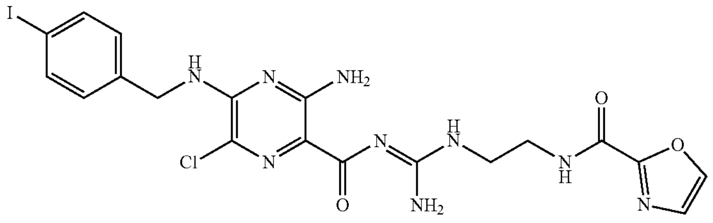 [SMILES: N/C(=N\C(=O)c1nc(Cl)c(NCc2ccc(I)cc2)nc1N)NCCNC(=O)c1ncco1] |
| 110 | 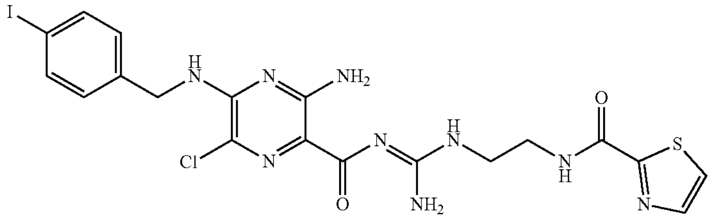 [SMILES: N/C(=N\C(=O)c1nc(Cl)c(NCc2ccc(I)cc2)nc1N)NCCNC(=O)c1nccs1] |

In some embodiments, provided herein is a compound described in Table 1 or a pharmaceutically acceptable salt thereof Representative examples of compounds detailed herein, including intermediates and final compounds according to the present disclosure are depicted herein. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein. It is understood that tautomeric forms of a compound of the formulae described herein may be present, for example, when tautomeric forms of a substituent are present, such as when a substituent embraces a keto-enol tautomer or the like. As another example, a tautomeric form of formula (III) is

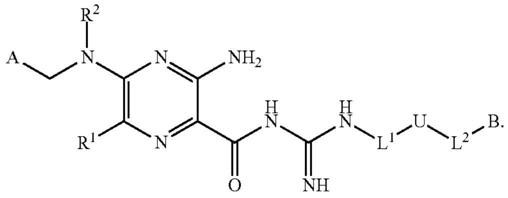

The present disclosure also includes any or all of the stereochemical forms, including any enantiomeric or diastereomeric forms of the compounds described, such as the compounds of Table 1. All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of Formula (I) or variations thereof described herein, where a fraction of one or more atoms are replaced by an isotope of the same element. Exemplary isotopes that can be incorporated into compounds of the invention in Jude isotopes of hydrogen, carbon, nitrogen, oxygen, phosphorus, sulfur, chlorine, such as $^{2}H$, $^{3}H$, $^{11}C$, $^{13}C$, $^{14}C$, $^{13}N$, $^{15}O$, $^{17}O$, $^{32}P$, $^{35}S$, $^{18}F$, $^{36}Cl$. Certain isotope labeled compounds (e.g. $^{3}H$ and $^{14}C$) is useful in compound or substrate tissue distribution studies. Incorporation of heavier isotopes such as deuterium ($^{2}H$) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound, such as would be generated in vivo following administration to a human.

Articles of manufacture comprising a compound described herein, or a salt or solvate thereof, in a suitable container are provided. The container may be a vial, jar, ampoule, preloaded syringe, i.v. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., for the treatment of cancer.

General Synthetic Methods

The compounds of the invention may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol.

In some embodiments, compounds of Formula (I) may be synthesized according to Schemes 1-3.

Scheme 1

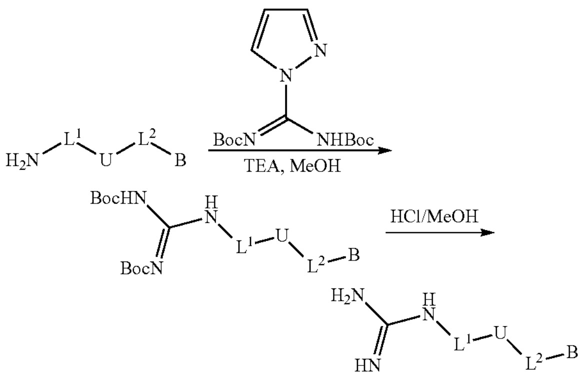

Scheme 2

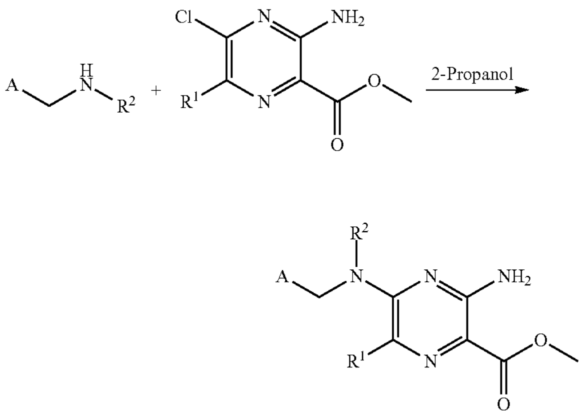

Scheme 3

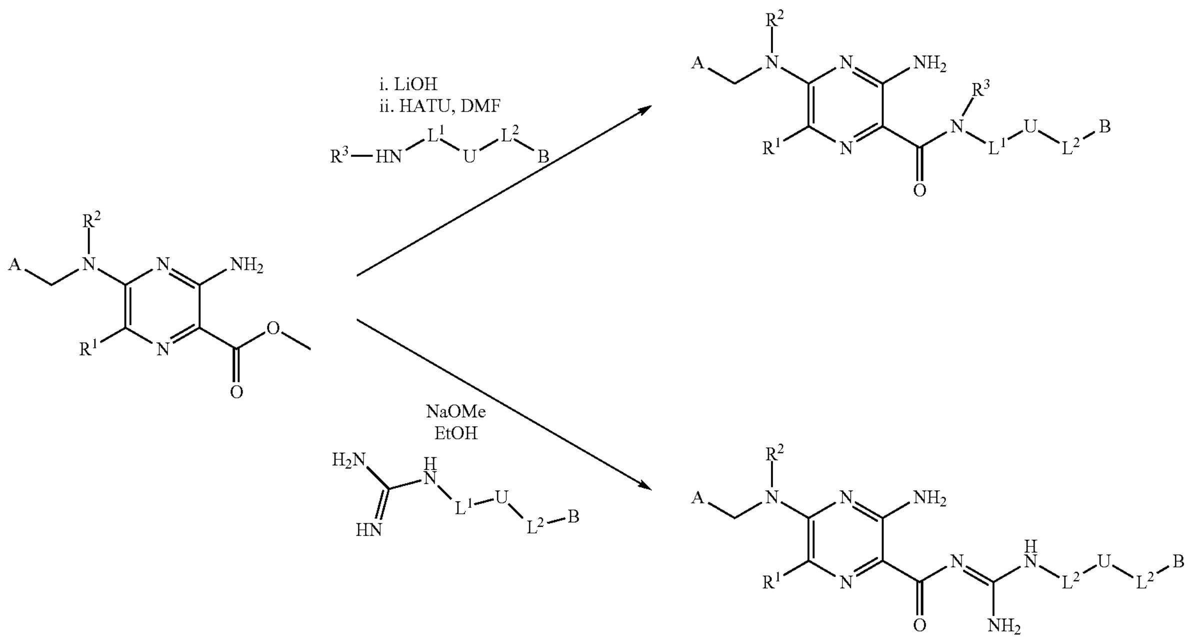

Pharmaceutical Compositions and Formulations

Pharmaceutical compositions of any of the compounds detailed herein are embraced by this disclosure. Thus, the present disclosure includes pharmaceutical compositions comprising a compound as detailed herein or a salt thereof and a pharmaceutically acceptable carrier or excipient. The present disclosure includes pharmaceutical compositions comprising a compound as detailed herein, or a tautomer or isomer thereof, or a pharmaceutically acceptable salt of any of the foregoing, and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid. emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences,* Mack Publishing Company, Philadelphia, Pa., $20^{th}$ ed. (2000), which is incorporated herein by reference.

Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or anti oxidants.

Any of the compounds described herein can be formulated in a tablet in any dosage form described, for example, a compound as described herein or a salt thereof can be formulated as a 10 mg tablet.

Compositions comprising a compound provided herein are also described. In one variation, the composition comprises a compound or salt thereof and a pharmaceutically acceptable carrier or excipient. In another variation, a composition of substantially pure compound is provided.

Methods of Use

Provided herein are methods of treating cancer. In some embodiments, the method comprises administering a compound disclosed herein, such as a compound of Formula (I), or any embodiment, variation, or aspect thereof, including a tautomer thereof, or a salt, such as a pharmaceutical salt, of any of the foregoing. In some embodiments, the method comprises administering a pharmaceutical composition disclosed herein, such as a pharmaceutical composition comprising a compound discloses herein.

In some embodiments, the cancer is leukemia, brain cancer, breast cancer, cervical cancer, renal cancer, liver cancer, lung cancer, pancreatic cancer, colorectal cancer, head and neck cancer, prostate cancer, vulvar cancer, skin cancer, or sarcoma. In some embodiments, the cancer is pancreatic cancer or colorectal cancer. In some embodiments, the cancer is colon cancer. In some embodiments, the cancer is prostate cancer. In some embodiments, the cancer is a carcinoma.

In some embodiments, provided herein is a method of treating colorectal cancer, comprising administering a compound disclosed herein. In some embodiments, the colorectal cancer is colon cancer. In some embodiments, the colorectal cancer is rectal cancer. In some embodiments, the colorectal cancer is a carcinoma.

The present compounds or salts thereof are believed to be effective for treating a cancer, such as colorectal cancer, that result in high expression of carcinoembryonic antigen (CEA) even though patients with high preoperative concentrations of CEA have a worse outcome than those with low concentrations of the marker (Duffy, Clinical Chem, 2001, 47(4): 624-630). In some embodiments, the subject has a blood CEA level of about or at least about 5 μg/L, such as about or at least about 6 μg/L, 7 μg/L, 8 μg/L, 9 μg/L, 10 μg/L, 20 μg/L, 30 μg/L, 40 μg/L, 50 μg/L, 100 μg/L, 200 μg/L, or 300 μg/L. In some embodiments, the subject has a blood carcinoembryonic antigen (CEA) level of about or at least about 10 μg/L.

In some embodiments, provided herein is a method of treating pancreatic cancer, comprising administering a compound disclosed herein. In some embodiments, the pancreatic cancer is an exocrine pancreatic cancer. In some embodiments, the pancreatic cancer is a carcinoma. In some embodiments, the pancreatic cancer expresses a p53 gene comprising a mutation. In some embodiments, the p53 gene mutation is at nucleic acid 742 or 818. In some embodiments, the gene mutation is 742C>T or 818G>A, In some embodiments, the pancreatic cancer expresses a mutated p53 protein. In some embodiments, the p53 protein mutation is at amino acid 248 or 273. In some embodiments, the p53 protein mutation is R248W or R273H.

In some embodiments, provided herein is a method of treating cancer, comprising administering a compound disclosed herein, wherein the cancer is associated with a hypoxic tumor. In some embodiments, the cancer is leukemia, brain cancer, breast cancer, cervical cancer, renal cancer, liver cancer, lung cancer, pancreatic cancer, colorectal cancer, head and neck cancer, prostate cancer, vulvar cancer, skin cancer, or sarcoma. In some embodiments, the cancer is pancreatic cancer or colorectal cancer. In some embodiments, the cancer is colon cancer. In some embodiments, the cancer is prostate cancer. In some embodiments, the cancer is a carcinoma. In some embodiments, the hypoxic tumor is a solid tumor.

In some embodiments, a plurality of cells in the hypoxic tumor express one or more hypoxia-inducible factor (HIF) proteins and/or one or more messenger ribonucleic acids (mRNAs) encoding a HIF protein. In some embodiments, the one or more HIF proteins and/or one or more mRNAs encoding a HIF protein are expressed at a higher level than a normal tissue. In some embodiments, the HIF protein is HIF-1 or HIF-2. In some embodiments, the HIF protein is HIF-1α.

In some embodiments the hypoxic tumor has one or more hypoxic conditions. In some embodiments, the hypoxic condition occurs for more than about 2 minutes, such as more than about 5 minutes, 10 minutes, 20 minutes, 40 minutes, 1 hour, 2 hours, 4 hours, 8 hours, 12 hours, 24 hours, 36 hours, 48 hours, or 72 hours. In some embodiments, the hypoxic condition occurs for 2 minutes to 72 hours. In some embodiments, the hypoxic condition occurs for 2 minutes to 1 hour. In some embodiments, the hypoxic condition fluctuates. In some embodiments, more than about 10% of the cells of the hypoxic tumor are hypoxic, such as more than about 20%, 25%, 30%, 40%, 50%, 60%, 75%, or 85%.

The level of hypoxia within a tumor varies by cancer type and stage and from patient to patient. Reported exemplary values of median partial pressure of oxygen ($pO_2$) and median % oxygen in human tumors and related normal tissues, and well as the fold $pO_2$ decrease in tumor from related normal tissues is shown in Table 2 (adapted from McKeown, Br J Radiol, 2014, 87:20130676). The fold reduction of tumor versus normal tissue shown in Table 2. is based on data presented in Table 2 except for prostate cancer wherein the normal tissue is contemporaneous measurements in the psoas muscle or measurements from normal prostate in bladder cancer patients.

TABLE 2

Reported median tumor $pO_2$ and % oxygen in human tumors and related normal tissues

| Tumor type | Median tumor $pO_2$ (mmHg) | Median tumor % oxygen | Median normal tissue $pO_2$ (mmHg) | Median normal tissue % oxygen | Fold $pO_2$ decrease |
|---|---|---|---|---|---|
| Brain | 12.0 | 1.7 | 26.0 | 3.4 | 2.0 |
| Head and neck | 10.0 | 1.3 | | 5.9 | 4.5 |
| cancer | 12.2 | 1.6 | 40.0 | 5.3 | 3.3 |
| | 14.7 | 1.9 | 43.8 | 5.8 | 3.0 |
| | 14.6 | 1.9 | 51.2 | 6.7 | 3.5 |
| Lung cancer | 14.3 | 1.9 | | 5.6 | 3.0 |
| | 16.6 | 2.2 | 42.8 | 5.6 | 2.6 |

TABLE 2-continued

Reported median tumor $pO_2$ and % oxygen in human tumors and related normal tissues

| Tumor type | Median tumor $pO_2$ (mmHg) | Median tumor % oxygen | Median normal tissue $pO_2$ (mmHg) | Median normal tissue % oxygen | Fold $pO_2$ decrease |
|---|---|---|---|---|---|
| Breast cancer | 10.0 | 1.3 | 52.0 | 6.8 | 5.2 |
| Cervical cancer | 9.0 | 1.2 | 42.0 | 5.5 | 4.7 |
| Liver | 6.0 | 0.8 | 30.0 | 3.9 | 5.0 |
| Pancreatic cancer | 2.7 | 0.4 | 51.6 | 6.8 | 19.1 |
| | 2.0 | 0.3 | | | 22.7 |
| Prostate cancer | 2.4 | 0.3 | 30.0 | 3.9 | 12.5 |
| | 4.5 | 0.6 | | | 6.7 |
| | 9.4 | 1.2 | 26.2 | 3.4 | 2.8 |
| Vulval cancer | 11.0 | 1.4 | | | |
| | 13.0 | 1.7 | | | |
| | 11.0 | 1.4 | | | |
| | 10.0 | 1.3 | | | |
| Melanoma | 11.6 | 1.5 | 40.5 | 5.3 | 3.5 |
| Renal cell carcinoma | 10.0 | 1.3 | 37.6 | 4.9 | 3.8 |
| Rectal carcinoma | 32.0 | 4.2 | 52.0 | 6.8 | 1.6 |
| | 19.0 | 2.5 | 52.0 | 6.8 | 2 7 |
| Sarcoma | 14.0 | 1.8 | 51.0 | 6.7 | 3.6 |
| Averages or total | 10.3 | 1.4 | 45.8 | 6.0 | 4.6 |
| Range of medians | 2.0-32.0 | 0.3-4.2 | 26.0-51.6 | 3.4-6.8 | |

In some embodiments, the hypoxic condition is a median oxygen level below 2%, such as below 1.5%, 1%, 0.8%, 0.6%, or 0.5%. In some embodiments, the hypoxic tumor has a median oxygen level below 1%, In some embodiments, the hypoxic tumor has a median oxygen level below 0.5%.

In some embodiments, the hypoxic condition is a median $pO_2$ of about or less than about 15 mmHg, such as about or less than about 10 mmHg, 8 mmHg, 5 mmHg, or 3 mmHg. In some embodiments, the hypoxic tumor has a median $pO_2$ of less than about 8 mmHg. In some embodiments, the hypoxic tumor has a median $pO_2$ of less than about 3 mmHg.

In some embodiments, the hypoxic condition is the percentage of $pO_2$ measurements of the hypoxic tumor that equal less than 10 mm Hg ($HP_{10}$) is greater than 50%, such as greater than 55%, 60%, 65%, 70%, 75%, or 80%. In some embodiments, the $HP_{10}$ is greater than 80%. In some embodiments, the hypoxic condition is the percentage of $pO_2$ measurements of the hypoxic tumor that equal less than 5 mm Hg ($HP_5$) is greater than 50%, such as greater than 55%, 60%, 65%, 70%, 75%, or 80%. In some embodiments, the $HP_5$ is greater than 80%. In some embodiments, the hypoxic condition is the percentage of $pO_2$ measurements of the hypoxic tumor that equal less than 2.5 mm Hg ($HP_{2.5}$) is greater than 50%, such as greater than 55%, 60%, 65%, 70%, 75%, or 80%. In some embodiments, the $HP_{2.5}$ is greater than 80%.

In some embodiments, the hypoxic condition is a median $pO_2$ that is less than about 30% of the $pO_2$ of a normal tissue, such as less than about 25%, 20%, 10%, 5%, 2,5%, 1%, 0.5%, or 0.1%. In some embodiments, the normal tissue is normal tissue in the subject. In some embodiments, the normal tissue is normal tissue in a healthy subject. In some embodiment, the normal tissue is an average of normal tissue from a plurality of subjects.

In some embodiments, the normal tissue and the cancer are derived from the same tissue or organ. In some embodiments, the cancer is leukemia and the normal tissue is healthy bone marrow; brain cancer and the normal tissue is healthy brain tissue; breast cancer and the normal tissue is healthy breast tissue; cervical cancer and the normal tissue is healthy cervical tissue; renal cancer and the normal tissue is healthy kidney tissue; liver cancer and the normal tissue is healthy liver tissue; lung cancer and the normal tissue is healthy lung tissue; pancreatic cancer and the normal tissue is healthy pancreatic tissue; colorectal cancer and the normal tissue is healthy colon or rectal tissue; head and neck cancer and the normal tissue is healthy head or neck tissue; prostate cancer and the normal tissue is healthy prostate tissue; vulvar cancer and the normal tissue is healthy vulvar tissue; or skin cancer and the normal tissue is healthy skin tissue. In some embodiments, the cancer is pancreatic cancer and the normal tissue is healthy pancreatic tissue.

In some embodiments, the normal tissue is non-cancerous muscle tissue. The level of tumor to muscle $pO_2$ has been shown to be a strong predictor of prognosis (reviewed in McKeown, Br J Radiol, 2014, 87:20130676). In some embodiments, the hypoxic tumor is located in a different tissue than the cancer was derived from. In such embodiments, it may be appropriate to compare the hypoxic tumor to nearby healthy tissue. Accordingly, in some embodiments, the hypoxic tumor is located in the bone marrow of the subject and the normal tissue is healthy bone marrow; the brain of the subject and the normal tissue is healthy brain tissue; the breast of the subject and the normal tissue is healthy breast tissue; the cervix of the subject and the normal tissue is healthy cervical tissue; the kidney of the subject and the normal tissue is healthy kidney tissue; the liver of the subject and the normal tissue is healthy liver tissue; the lung of the subject and the normal tissue is healthy lung tissue; the pancreas of the subject and the normal tissue is healthy pancreatic tissue; the colon of the subject and the normal tissue is healthy colon tissue; the rectum of the subject and the normal tissue is rectal tissue; the head of the subject and the normal tissue is healthy head tissue; the neck of the subject and the normal tissue is healthy neck tissue; the prostate of the subject and the normal tissue is healthy prostate tissue; the vulva of the subject and the normal tissue is healthy vulvar tissue; or the skin of the subject and the normal tissue is healthy skin tissue. In some embodiments, the hypoxic tumor is located in the pancreas and the normal tissue is healthy pancreatic tissue.

In some embodiments, the methods described herein further comprise obtaining information regarding the hypoxic status of the hypoxic tumor. In some embodiments, the information is one or more of the following: detection of hypoxia biomarkers, such as EU gene or protein expression or measurement of the $pO_2$ or percent $O_2$ of the hypoxic tumor. In some embodiments, the methods described herein further comprise measuring the $pO_2$ or percent $O_2$ of the hypoxic tumor. Methods of measuring the $pO_2$ are known in the art. For example, in some embodiments, measuring or measurement of the $pO_2$ or percent $O_2$ comprises using positron emission tomography (PET) imaging, computerized tomography (CT) imaging, polarographic O2 sensors, blood oxygen level dependent (BOLD) magnetic resonance imaging (MRI), dynamic contrast-enhanced (DCE) MRI or electron paramagnetic resonance (EPR) oximetry. In some embodiments, the subject was administered an agent that allows detection of hypoxia. In some embodiments, the subject was administered an agent that allows detection of hypoxia and hypoxia was detected in a sample of the hypoxic tumor. In some embodiments, the measuring (or measurement) is performed in vitro. In some embodiments, the in vitro measuring (or measurement) comprises detecting an exogenous hypoxic marker in a sample of the hypoxic tumor. In some embodiments, the in vitro measuring (or measurement) comprises detecting an endogenous hypoxic marker in a sample of the hypoxic tumor. In some embodiments, the measuring (or measurement) is performed in vivo. In some embodiments, the subject is not under general anesthesia during the measuring. In some embodiments, the subject is under local anesthesia during the measuring.

In some embodiments, a compound or salt thereof described herein or a composition described herein may be used in a method of treating cancer in a subject, wherein the subject has had a prior treatment. In the embodiments, the cancer is a recurrent cancer. In some embodiments, the cancer is resistant or refractory to the prior treatment. In some embodiments, the cancer has progressed on the prior treatment. In some embodiments, the prior treatment was treatment with radiation, surgery, a taxane, a platinum-based agent, a nucleoside analog, an immune-check point inhibitor, a Cox-2 inhibitor, an anthracycline, a pyrimidine analog, a topoisomerase inhibitor, an mTOR inhibitor, a proteasome inhibitor, an angiogenesis inhibitor, a B-Raf inhibitor, a tyrosine kinase inhibitor, or combinations thereof. In some embodiments, the cancer is resistant to treatment with radiation, a taxane, a platinum-based agent, a nucleoside analog, an immune-check point inhibitor, a Cox-2 inhibitor, an anthracycline, a pyrimidine analog, a topoisomerase inhibitor, an mTOR inhibitor, a proteasome inhibitor, an angiogenesis inhibitor, a B-Raf inhibitor, a tyrosine kinase inhibitor, or combinations thereof. In some embodiments, the cancer is resistant to treatment with gemcitabine, docetaxel, paclitaxel, paclitaxel protein-bound particles, cisplatin, or radiation. In some embodiments, the cancer is resistant to treatment with cisplatin.

In some embodiments, administration of a compound disclosed herein reduces tumor growth, tumor proliferation, or the formation of metastatic tumors in the subject. In some embodiments, tumor growth is slowed or arrested. In some embodiments, tumor growth is reduced at least about 10%, such as at least about 20%, 30%, 40%, 50%, 60%, 70%, 80%, or 90%. In some embodiments, the tumor is reduced in size. In some embodiments, tumor size is reduced at least about 10%, such as at least about 20%, 30%, 40%, 50%, 60%, 70%, 80%, or 90%. In some embodiments, formation of a metastatic tumor is prevented or slowed. Tumor growth, tumor proliferation, or the formation of metastatic tumors may be compared to the tumor growth, tumor proliferation, or formation of metastatic tumors in the subject prior to administration of the compound or to tumor growth, tumor proliferation, or the formation of metastatic tumors in a similar subject or group of subjects. Methods of measuring tumor growth, tumor proliferation, or the formation of metastatic tumors are known in the art, for example by repeated imaging of the subject.

Dosing and Method of Administration

The dose of a compound administered to an individual (such as a human) may vary with the particular compound or salt thereof, the method of administration, and the particular disease, such as type and stage of cancer, being treated. In some embodiments, the amount of the compound or salt thereof is a therapeutically effective amount.

The effective amount of the compound may in one aspect be a dose of between about 0.01 and about 100 mg/kg. Effective amounts or doses of the compounds of the invention may be ascertained by methods, such as modeling, dose escalation, or clinical trials, taking into account factors, e.g., the mode or route of administration or drug delivery, the pharmacokinetics of the agent, the severity and course of the disease to be treated, the subject's health status, condition, and weight.

Any of the methods provided herein may in one aspect comprise administering to an individual a pharmaceutical composition that contains an effective amount of a compound provided herein or a salt thereof and a pharmaceutically acceptable excipient.

A compound or composition of the invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

The compounds provided herein or a salt thereof may be administered to an individual via various routes, including, e.g., intravenous, intramuscular, subcutaneous, oral and transdermal. A compound provided herein can be administered frequently at low doses, known as 'metronomic therapy,' or as part of a maintenance therapy using compound alone or in combination with one or more additional drugs. Metronomic therapy or maintenance therapy can comprise administration of a compound provided herein in cycles. Metronomic therapy or maintenance therapy can comprise intra-tumoral administration of a compound provided herein.

In one aspect, the invention provides a method of treating cancer in an individual by parenterally administering to the individual (e.g., a human) an effective amount of a compound or salt thereof. In some embodiments, the route of administration is intravenous, intra-arterial, intramuscular, or subcutaneous. In some embodiments, the route of administration is oral. In still other embodiments, the route of administration is transdermal.

In some embodiments, the subject is a mammal. In some embodiments, the subject is a human, primate, dog, cat, rabbit, or rodent. In some embodiments, the subject is a human. In some embodiments, the subject has a cancer disclosed herein.

Also provided herein are uses of a compound described herein, or pharmaceutical compositions comprising a compound described herein, in the manufacture of a medicament for the treatment of a disease described herein. Further provided herein are uses of a compound described herein, or a pharmaceutical composition comprising a compound described herein, in a method of treatment of a disease described herein, as well as pharmaceutical compositions for use in a method of treatment described herein.

In some embodiments, the method further comprises administering a second cancer treatment. In some embodiments, the second cancer treatment is radiation, surgery, a taxane, a platinum-based agent, a nucleoside analog, an immune-check point inhibitor, a Cox-2 inhibitor, an anthracycline, a pyrimidine analog, a topoisomerase inhibitor, an mTOR inhibitor, a proteasome inhibitor, an angiogenesis inhibitor, a B-Raf inhibitor, or a tyrosine kinase inhibitor. In some embodiments, the method further comprises administering radiation. In some embodiments, the method further comprises administering radiation and surgery. Either the compound described herein, or a pharmaceutically acceptable salt thereof, or a pharmaceutical composition described herein; or the second cancer treatment may be administered first.

In some embodiments, a compound described herein, or a pharmaceutically acceptable salt thereof, or a pharmaceutical composition described herein and a second cancer treatment are sequentially administered, concurrently administered or simultaneously administered. In certain embodiments, a compound described herein, or a pharmaceutically acceptable salt thereof, or a pharmaceutical composition described herein; and a second cancer treatment are administered with a time separation of about 15 minutes or less, such as about any of 10, 5, or 1 minutes or less. In certain embodiments, a compound described herein, or a pharmaceutically acceptable salt thereof, or a pharmaceutical composition described herein; and a second cancer treatment are administered with a time separation of about 15 minutes or more, such as about any of 20, 30, 45, 60, or more minutes. In certain embodiments, a compound described herein, or a pharmaceutically acceptable salt thereof, or a pharmaceutical composition described herein; and the second cancer treatment are administered simultaneously.

Articles of Manufacture and Kits

Also provided are articles of manufacture comprising a compound of the disclosure or a salt thereof, composition, and unit dosages described herein in suitable packaging for use in the methods described herein. Suitable packaging is known in the art and includes, for example, vials, vessels, ampules, bottles, jars, flexible packaging and the like. An article of manufacture may further be sterilized and/or sealed.

The present disclosure further provides kits for carrying out the methods of the invention, which comprises one or more compounds described herein or a composition comprising a compound described herein. The kits may employ any of the compounds disclosed herein. In one variation, the kit employs a compound described herein or a salt thereof. The kits may be used for any one or more of the uses described herein, and, accordingly, may contain instructions for the treatment of cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. :For example, kits may be provided that contain sufficient dosages of a compound as disclosed herein and/or an additional pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The disclosure can be further understood by reference to the following examples, which are provided by way of illustration and are not meant to be limiting.

EXAMPLES

Synthetic Examples

Example S1. Synthesis of 1-((1-phenethylpiperidin-4-yl)methyl)guanidine hydrochloride

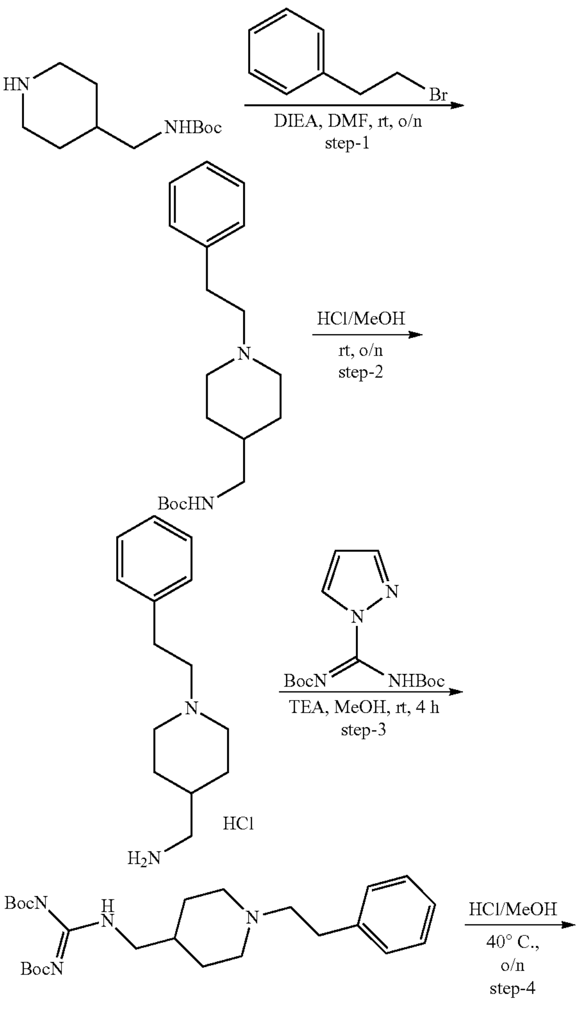

-continued

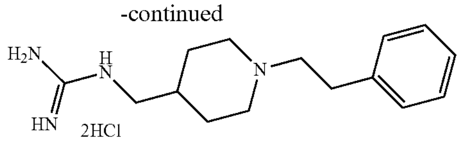

Step 1: Synthesis of tert-butyl ((1-phenethylpiperidin-4-yl)methyl)carbamate. To a solution of tert-butyl (piperidin-4-ylmethyl)carbamate (9.0 g, 42.0 mmol) in DNF (90 mL) was added (2-bromoethyl)benzene (11.7 g, 63.0 mmol) and DIEA (16.3 g, 126.0 mmol). The resulting mixture was stirred at room temperature overnight. TLC showed the reaction was complete. The reaction mixture was poured into water and extracted with DCM. The combined organic layers were washed with brine, dried over anhydrous $Na_2SO_4$ and concentrated under reduced pressure. The residue was purified by silica gel chromatography to afford the title compound. LCMS 319.3 $[M+1]^+$.

Step 2: Synthesis of (1-phenethylpiperidin-4-yl)methanamine hydrochloride. A mixture of tert-butyl ((1-phenethylpiperidin-4-yl)methyl)carbamate (8.6 g, 27.0 mmol) and HCl/MeOH (4 N, 100 mL) was stirred at room temperature overnight. TLC showed the reaction was complete. The solvent was removed under reduced pressure to give the title compound. LCMS: 219.4 $[M+1]^+$.

Step 3: Synthesis of Cert-butyl (tert-butoxycarbonylamino)((1-phenethyl-4-yl)methylamino)-methylenecarbamate. To a solution of (1-phenethylpiperidin-4-yl)methanamine hydrochloride (6 g, crude) in MeOH (100 mL) was added tert-butyl (((tert-butoxycarbonyl)amino)(1H-pyrazoll-yl)methylene)-carbamate (8.0 g, 26.0 mmol) and TEA (9.5 g, 94.0 mmol). The resulting mixture was stirred at room temperature for 4 h. TLC showed the reaction was complete. The solvent was removed under reduced pressure. The residue was purified by silica gel chromatography to give a semi-pure product which was washed with petroleum ether to afford the title compound. LCMS 461.3 $[M+1]^+$.

Step 4: Synthesis of 1-((1-phenethylpiperidin-4-yl)methyl)guanidine dihydrochloride. A mixture of tert-butyl (tert-butoxycarbonylamino)((1-phenethyl-4-yl)methylamino)-methylenecarbamate (3.6 g, 7.8 mmol) and HCl/MeOH (4 N, 40 mL) was stirred overnight at 40° C. TLC showed the reaction was complete. The solvent was removed under reduced pressure to give the title compound. LCMS 216.3 $[M+1]^+$; $^1H$ NMR (400 MHz, $D_2O$) δ 7.45-7.30 (m, 5H), 3.73-3.63 (m, 2H), 3.41-3.35 (m, 2H), 3.18-2.95 (m, 6H), 2.11-1.88 (m, 3H), 1.56-1.39 (m, 2H).

Example S2. Synthesis of 2-(4-benzylpiperazin-1-yl)ethanamine dihydroehloride

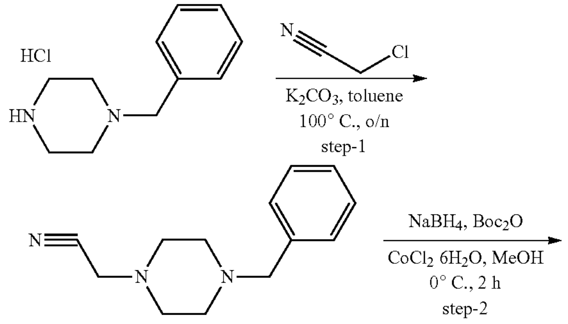

-continued

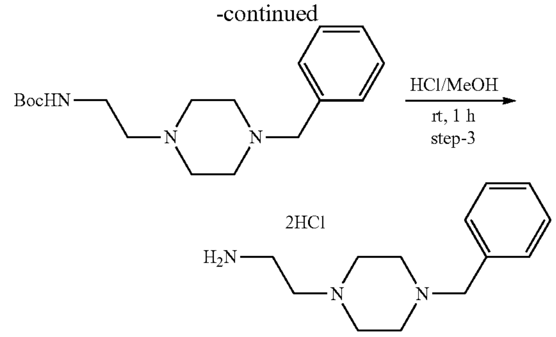

Step 1: Synthesis of 2-(4-benzylpiperazin-1-yl)acetonitrile. To a solution of 1-benzylpiperazine hydrochloride (23.0 g, 0.11 mol) in toluene (250 mL) was added 2-chloroacetonitrile (15.6 g, 0,13 mol) and $K_2CO_3$ (33.0 g, 024 mol). The resulting mixture was stirred at overnight at 100° C. TLC showed the reaction was complete. The reaction mixture was poured into water and extracted with EtOAc. The combined organic layers were washed with brine, dried over anhydrous $Na_2SO_4$ and concentrated under reduced pressure. The residue was purified by silica gel chromatography to afford the title compound. LCMS 216.4 $[M+1]^+$.

Step 2: Synthesis of tert-butyl (2-(4-benzylpiperazin-1-yl)ethyl)carbamate. A solution of 2-(4-benzylpiperazin-1-yl) acetonitrile (13.0 g, 60.4 mmol) in MeOH (130 mL) was cooled to 0° C. Then $CoCl_2 \cdot 6H_2O$ (5.8 g, 24.1 mmol) and $Boc_2O$ (33.0 g, 0.1.5 mol) were added followed by portion-wise addition of $NaBH_4$ (8.0 g, 0.21 mol). The resulting mixture was stirred for 2 h at 0° C. TLC analysis indicated the reaction was complete. The reaction was quenched with water and ammonium hydroxide and then extracted with DCM. The combined organic phases were washed with brine, dried over $Na_2SO_4$ and evaporated. The residue was purified by silica gel chromatography to afford the title compound. LCMS 320.2 $[M+1]^+$.

Step 3: Synthesis of 2-(4-benzylpiperazin-1-yl) pethanamine dihydrochloride. A mixture of tert-butyl (2-(4-benzylpiperazin-1-yl)ethyl)carbamate (12.0 g, 37.6 mmol) and HCl/MeOH (4 N, 100 mL) was stirred at room temperature for 1 h. TLC showed the reaction was complete. The solvent was removed under reduced pressure. The residue was washed with petroleum ether to afford the title compound. LCMS 220.3 $[M+1]^+$; $^1H$ NMR (400 MHz, DMSO-$d_6$) δ 12.26 (br s, 1H), 8.38 (s, 3H), 7.70-7.64 (m, 2H), 7.52-7.38 (m, 3H), 4.41 (s, 2H), 3.81-3.09 (m, 12H).

Example S3. Synthesis of 1-(3-(4-chlorophenoxy)propyl)guanidine hydrochloride

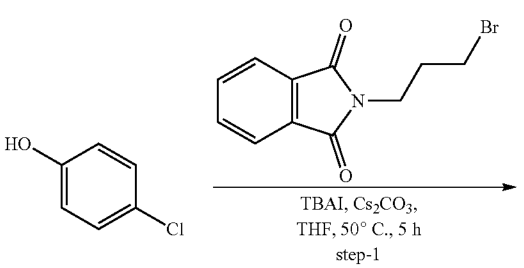

-continued

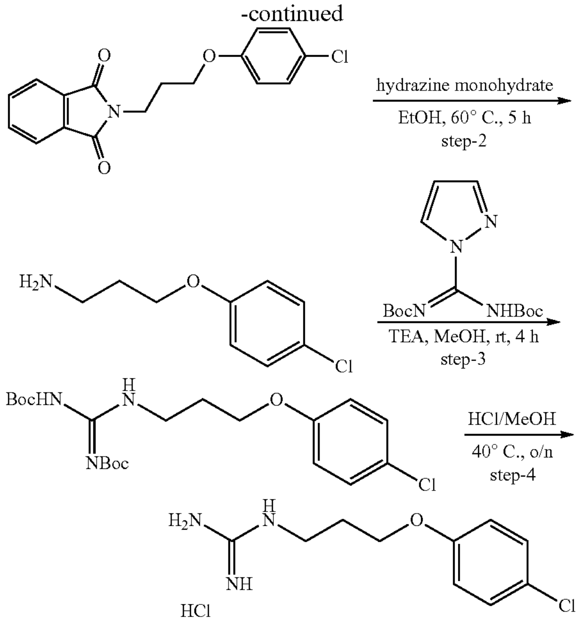

Step 1: Synthesis of 2-(3-(4-ehlorophenoxy)propyl)isoindoline-1,3-dione. To a stirred solution of 4-chlorophenol (9 g, 70.0 mmol, 1.0 eq) in THF (200 mL) was added 2-(3-bromopropyl) isoindoline-1 ,3-dione (20.64 g, 77.0 mmol, 1.1 eq) , TBAI (5.17 g, 14.0 mmol, 0.2 eq) and cesium carbonate (41.05 g, 126.0 mmol, 1.8 eq). Then the reaction mixture was heated at 50° C. for 5 h, The reaction mixture was quenched with water and extracted with ethyl acetate (100 mL×4). The combined organic layers were washed with brine, dried over anhydrous sodium sulphate, filtered and concentrated to get the title compound which was carried to next step without any further purification.

Step 2: Synthesis of 3-(4-chlorophenoxy)propan-1-amine. To a stirred solution of 2-(3-(4-ehlorophenoxy)propyl)isoindoline-1,3-dione (25 g , 79.2 mmol, 1.0 eq) in ethanol (300 mL) was added hydrazine monohydrate (150 mL). The mixture was heated at 60° C. for 5 h. After completion, the reaction mixture was cooled to room temperature and diluted with diethyl ether and stirred for 10 min. The resulting precipitate was filtered and washed with ether. The filtrate was concentrated under reduced pressure to get the crude product which was diluted with acetonitrile and stirred for 10 min. The resulting precipitate was filtered and washed with additional acetonitrile. The filtrate was concentrated under reduced pressure to afford the title compound.

Step 3:Synthesis of tert-butyl (tert-butoxycarbonylamino) (3-(4-chlorophenoxy)propylamino)-methylenecarbamate. A solution of 3-(4-chlorophenoxy)propan-1-amine (8.16 g, 43.93 mmol), tert-butyl (1H-pyrazol-1-yl)methanediylidenedicarbamate (25 g , 79.2 mmol) and TEA (13,34 g, 131,79 mmol) in MeOH (100 mL) was stirred at room temperature for 1 h. After completion, the resulting precipitate was filtered and washed with MeOH to afford the title compound.

Step 4: Synthesis of 1-(3-(4-chlorophenoxy)propyl)guanidine hydrochloride. A solution of tea-butyl (tert-butoxycarbonylamino)(3-(4-chlorophenoxy)propylamino) methylenecarbamate (12.5 g, 29.2 mmol) in HCl/MeOH (4 M, 150 mL) was stirred overnight at 40° C. The mixture was then concentrated to afford the title compound. LCMS 228.3 $[M+1]^+$; $^1H$ NMR (400 MHz, DMSO-$d_6$) δ 7.98 (t, J=5.6 Hz, 1H), 7,35-7.31 (m, 2H), 6.98 (q, J=5.6 Hz, 2H), 4.03 (t, J=6.0 Hz, 2H), 3.28 (q, J=6.4 Hz, 2H), 1.92 (p, J=6.4 Hz, 2H).

Example S4. Synthesis of methyl 3-amino-6-chloro-5-(4-iodobenzylamino)pyrazine-2-carboxylate

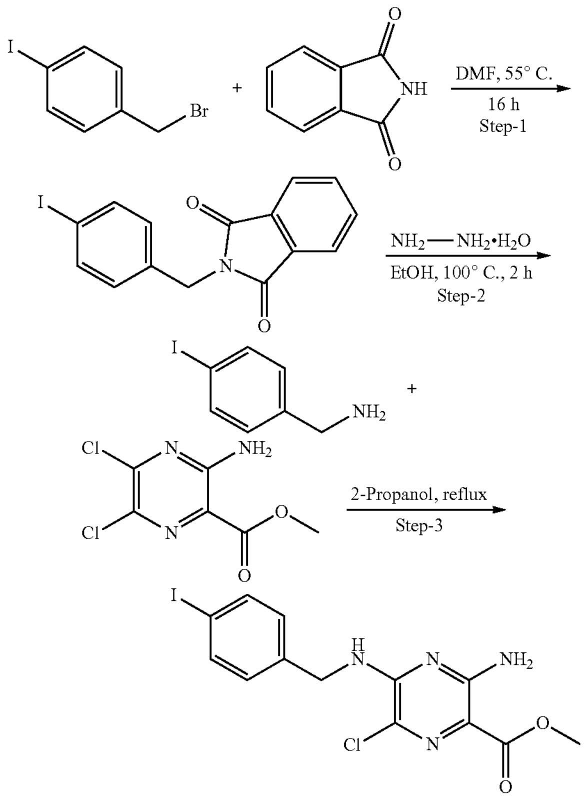

Step 1: Synthesis of 2-(4-iodobenzyl)isoindoline-1,3-dione. To a stirred solution of 4-iodobenzylbromide (20 g, 67.8 mmol) in DMF (60 mL) was added potassium phthalimide (13.8 g, 74.5 mmol, 1.1 eq) and the mixture was stirred at 55° C. for 16 h. The reaction was complete after 16 h and to the mixture was added water (200 mL). The aqueous layer was then extracted with EtOAc (100 mL×3). The combined organic layers were washed with water (50 mL), brine (50 mL), dried over anhydrous $Na_2SO_4$, filtered and concentrated under reduced pressure to obtain a crude which was triturated with n-pentane/diethyl ether (3:1) to afford the title compound. LCMS 364 $[M+H]^+$.

Step 2: Synthesis of (4-iodophenyl)methanatnine. To a stirred solution of 2-(4-iodobenzyl)isoindoline-1,3-dione (14.5 g, 39.9 mmol) in ethanol (200 mL) was added hydrazine hydrate (15 mL) and the resulting mixture was heated at 100° C. for 2 h. The reaction was monitored by TLC. After completion, the mixture was concentrated under reduced pressure. The crude residue obtained was diluted with water (150 mL) and extracted with EtOAc (200 mL×3). The combined organic layers were washed with brine (150 mL), dried over anhydrous $Na_2SO_4$, filtered and concentrated under reduced pressure to afford the title compound. LCMS 234 $[M+H]^+$.

Step 3: Synthesis of methyl 3-amino-6-chloro-5-(4-iodobenzylamino)pyrazine-2-carboxylate. To a solution of methyl 3-amino-5,6-dichloropyrazine-2-carboxylate (2.8 g, 12.6 mmol) in 2-propanol (50 mL) was added (4-iodophenyl)methanamine (8.6 g, 37.0 mmol, 3.0 eq) and the mixture was refluxed at 90° C. for 2 h. The reaction was monitored by TLC. After completion, the mixture was concentrated under reduced pressure to obtain a crude residue which was purified by CombiFlash chromatography to afford the title compound. LCMS 419 $[M+H]^+$.

Example S5. Synthesis of 3-amino-N-(2-(4-benzylpiperazin-1-yl)ethyl)-6-chloro-5-(4-iodobenzylamino) pyrazine-2-carboxamide (Compound No. 1)

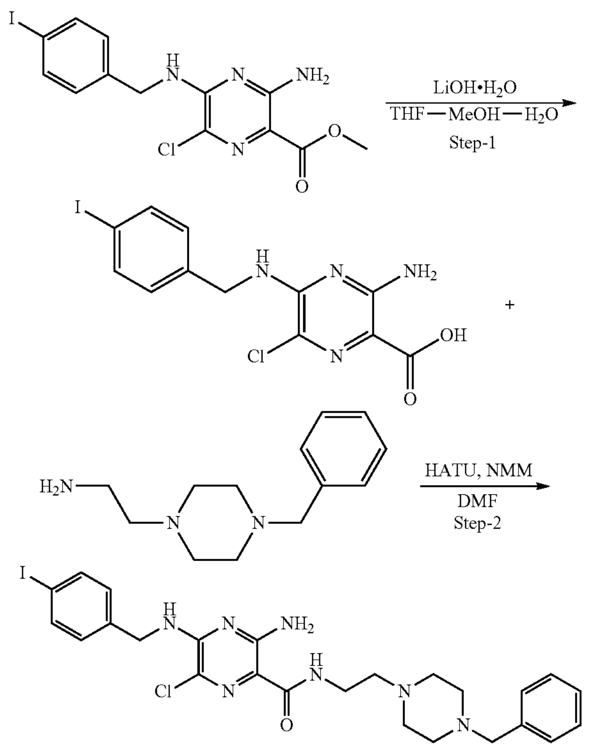

Step 1: Synthesis of 3-amino-6-chloro-5-(4-iodobenzylamino)pyrazine-2-carboxylic acid. To a stirred solution of methyl 3-amino-6-chloro-5-(4-iodobenzylamino)pyrazine-2-carboxylate (300 mg, 0.71 mmol) in a mixture of THF, MeOH and $H_2O$ (6:3:1, 10 mL) was added $LiOH{\cdot}H_2O$ (58.5 mg, 0.71 mmol, 2.0 eq) and the mixture was stirred at room temperature for 4 h. The reaction was monitored by TLC. After completion, the mixture was quenched with saturated, aqueious $NH_4Cl$ solution (40 mL) and extracted with DCM (30 mL×4). The combined organic layers were washed with brine (30 mL), dried over anhydrous $Na_2SO_4$, filtered and concentrated under reduced pressure to afford the title compound. LCMS 405 $[M+H]^+$.

Step 2: Synthesis of 3-amino-N-(2-(4-benzylpiperazin-1-yl)ethyl)-6-chloro-5-(4-iodobenzylamino) pyrazine-2-carboxamide. To a stirred solution of 3-amino-6-chloro-5-(4-iodobenzylamino)pyrazine-2-carboxylic acid (250 mg, 0.61 mmol, 1.0 eq.) in DMI (7 mL) was successively added HATU (347 mg, 0.91 mmol, 1.5 eq) and 1-methylmorpholine (0.33 mL, 3.05 mmol, 5 eq) at 0° C. The mixture was stirred at same temperature for 10 min before adding 2-(4-benzylpiperazin-1-yl)ethanamine (160 mg, 0.73 mmol, 1.2 eq). The resultant mixture was stirred at room temperature for 3 h. The reaction was monitored by TLC and LC-MS. After completion, the mixture was diluted with water (2.0 mL) and extracted with EtOAc (30 mL×3). The combined organic layers were washed with water (25 mL), brine (25 mL), dried over anhydrous $Na_2SO_4$, filtered and concentrated under reduced pressure to obtain a crude which was purified by CombiFlash chromatography to afford the title compound. LCMS 606 $[M+H]^+$; $^1H$ NMR (400 MHz, MeOD) δ 7.68-7.61 (m, J=8.3 Hz, 2H), 7.35 (d, J=4.4 Hz, 5H), 7.16-7.10 (m, J=8.3 Hz, 2H), 3.67 (br s, 2H), 3.49 (s, 2H), 2.73 (br s, 10H), 1.29 (s, 2H), Example S6. Synthesis of 3-amino-N-(amino(((1-phenethylpiperidin-1-yl)methyl)amino)methylene)-6-chloro-5-((4-iodobenzyl)amino)pyrazine-2-carboxamide (Compound No. 51)

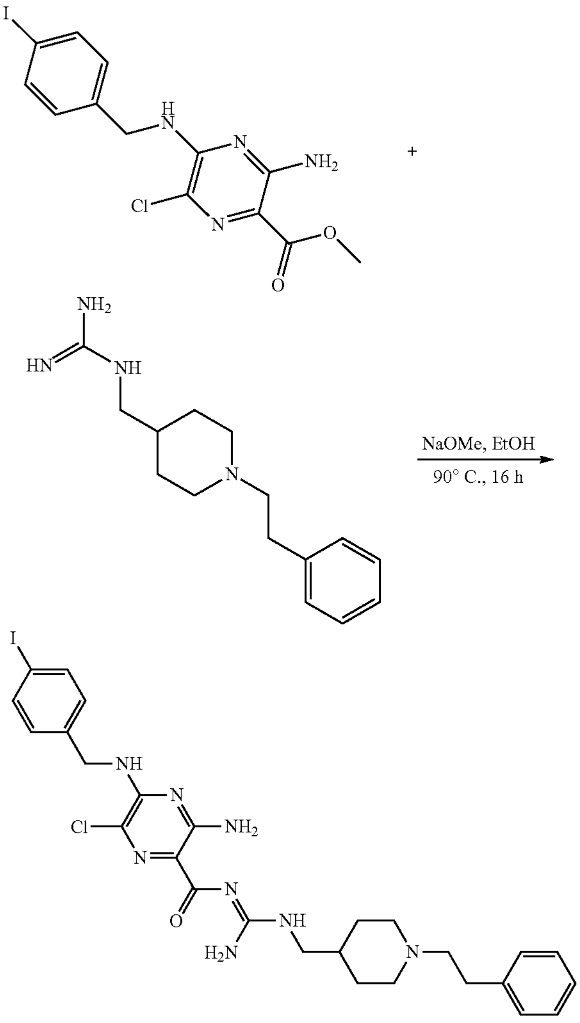

To 1((1-phenethylpiperidin-4-yl)methyl)guanidine (460 mg, 1.77 mmol, 3.0 eq) in anhydrous isopropyl alcohol (10 mL) was added sodium methoxide (159 mg, 2,95 mmol, 5.0 eq) and the mixture was stirred at room temperature for 1 h under an inert atmosphere. During that time, a precipitate formed which was removed by filtration. The resulting filtrate was concentrated under reduced pressure to obtain the guanidine base. The guanidine base was further dissolved in anhydrous isopropyl alcohol (8 mL) with methyl 3-amino-6-chloro-5-(4-iodobenzylamino)pyrazine-2-carboxylate (250 mg, 0.59 mmol, 1.0 eq) and the mixture was refluxed for 16 h at 90 ° C. The mixture was cooled to room temperature and concentrated under reduced pressure to afford a crude residue which was purified by reversed-phase HPLC to provide the title compound. LCMS 647 $[M+K]^+$; $^1H$ NMR (400 MHz, MeOD) δ 7.70-7.60 (m, J=8.3 Hz, 2H), 7.38-7.2.1 (m, 5H), 7.19-7.09 (m, J=8.3 Hz, 2H), 3.61 (br s, 2H), 3,35-3.13 (m, 3H), 3.03 (br s, 214), 2.04 (br, s, 3H), 1,58 (br s, 3H), 1.29 (br s, 2H), 0.86-0.60 (m, 2H).

Example 7. Synthesis of 3-amino-4-(amino(3-(4-chlorophenoxy)propylamino)methylene)-6-chloro-5-(4-iodobenzylamino)pyrazine-2-carboxamide (Compound No. 52)

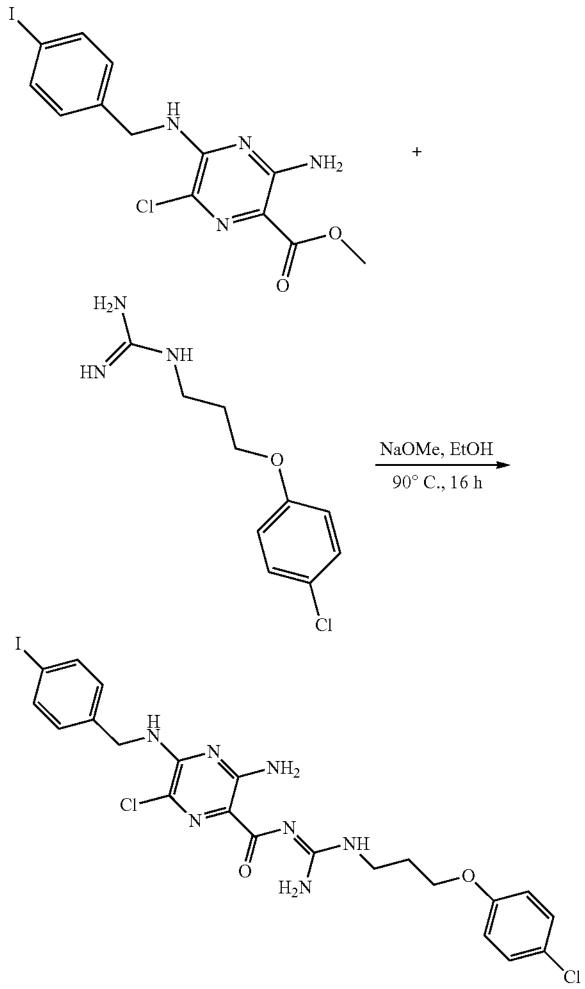

To 1-(3-(4-chlorophenoxy)propyl)guanidine (653 mg, 2.87 mmol, 4.0 eq) in anhydrous isopropyl alcohol (10 mL) was added sodium methoxide (191 mg, 3.55 mmol, 5.0 eq) and the mixture was stirred at room temperature for 1 h under an inert atmosphere. During that time, a precipitate formed which was removed by filtration. The resulting filtrate was concentrated under reduced pressure to obtain the guanidine base. The guanidine base was further dissolved in anhydrous isopropyl alcohol (8 mL) with methyl 3-amino-6-chloro-5-(4-iodobenzylamino)pyrazine-2-carboxylate (300 mg, 0.71 mmol, 1.0 eq) and the mixture was refluxed for 16 h at 90° C. The mixture was cooled to room temperature and concentrated under reduced pressure to afford a crude residue which was purified by reversed-phase HPLC to provide the title compound. LCMS 614 $[M+H]^+$; $^1$HNMR (400 MHz, MeOH) δ 7,65 (d, J=7.7 Hz, 2H), 7.24 (d, J=8.5 Hz, 2H), 7.15 (d, J=8,0 Hz, 2H), 6.93 (d, J=8.6 Hz, 2H), 4.62 (s, 2H), 4.14-4.04 (m, 2H), 3.54 (t, J=6.5 Hz, 2H), 2.14 (dp, J=13.6, 7.0, 6.5 Hz, 2H).

BIOLOGICAL EXAMPLES

Example B1. Determination of Potency of Compounds in Cell Proliferation Assay in Selected Cancer Cell Lines HCT 116 colorectal carcinoma cells (ECACC/Sigma-Aldrich #91091005) were seeded in medium (McCoy's 5a+10% FBS) at a cell count of 1500 cells per 100 μL per well in a 96 well edge plate (ThermoFisher #167425). Cells were cultured at 37° C. for 24 hr in 5% $CO_2$ environment (culture conditions) in a Nuaire incubator (humidified). Serially diluted test compounds (100 μL) within the desired testing concentration range (e.g., 0.014-30 μM) were added to the culture plate and the cells were further incubated in culture conditions for 72 hr. The experiment was terminated at the designated incubation time by replacing the medium with 100 μL, of 1 mM resazurin (Sigma-Aldrich #R7017) prepared in culture medium, and the plates were further incubated in culture conditions for 4-6 hr. Fluorescence was recorded using a multimodal plate reader (Biotek Synergy Neo) at an excitation wavelength of 535 nm and emission wavelength of 590 nm to obtain relative fluorescence units.

Data were analyzed as follows: the background fluorescence (blank containing only medium) value was subtracted from each reading and normalized with the vehicle control (MIS( )treated cells) to obtain percent survival/proliferation. Percent survival was subtracted from 100 to get the percent inhibition of proliferation which was used to calculate $IC_{50}$ values.

Testing in MIA PaCa-2 human pancreatic carcinoma cells (ATCC® CRL-1420™) was done identically, except that the medium used was DMFM+10% FBS+2.5% horse serum, the cells were seeded at a cell count of 3000 cells per 100 μL per well and the test compound incubation time was 72 or 96 hr. The potency of compounds in other cell lines may be determined in an analogous manner.

The results are shown in Table 3.

TABLE 3

| Compound No. | HCT 116 $IC_{50}$ (μM), 72 hr | MIA PaCa-2 $IC_{50}$ (μM), 96 hr |
|---|---|---|
| 1 | 16.3 | 30.9 |
| 51 | 0.69 | 1.90 |
| 52 | 1.33 | 2.92 |

Example B2. Determination of Microsome Stability for Test Compounds

In a 96 deep well plate, 2.5 μL of 20 μM of each test compound in potassium phosphate buffer (pH 7,4) with 2% 1:9 DMSO:acetonitrile were added to 5 μL of 5 mg/mL microsomes (human liver microsomes (hLM), rat liver microsomes (rLM), or mouse liver microsomes (mLM)) and 37.5 μL of 100 mM prewarmed phosphate buffer (pH 7.4). Time point 0 ($T_0$) samples were immediately quenched with 200 μL of chilled acetonitrile containing 50 ng/mL of internal standard. 5 4, of 10 mM NADPH was added to all other samples to start the reaction. The plate was incubated in a reciprocating water bath at 37 ° C. on 50 rpm for the duration of the assay. The remaining samples were quenched with 200 μL of chilled acetonitrile containing 50 ng/mL of internal standard at various timepoints. The samples were analyzed by LC-MS/MS (Sciex API 4500 QTrap). The % remaining, terminal elimination rate constant (K), half-life ($t_{1/2}$), and intrinsic clearance ($CL_{int}$) were calculated.

| Compound No. | hLM $CL_{int}$ (μg/min/mg) | rLM $CL_{int}$ (μg/min/mg) | mLM $CL_{int}$ (μg/min/mg) |
|---|---|---|---|
| 1 | 258 | 201 | 176 |
| 51 | 52 | 29 | 67 |
| 52 | 20 | 49 | 81 |

Although the foregoing disclosure has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the disclosure.

What is claimed is:

1. A compound having the following structure

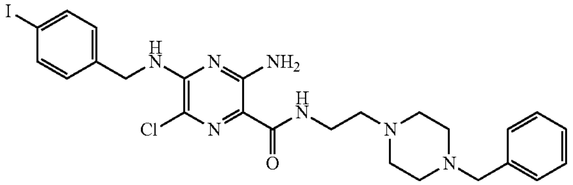 [SMILES: Nc1nc(NCc2ccc(I)cc2)c(Cl)nc1C(=O)NCCN1CCN(Cc2ccccc2)CC1]

or a pharmaceutically acceptable salt thereof.

2. A compound having the following structure

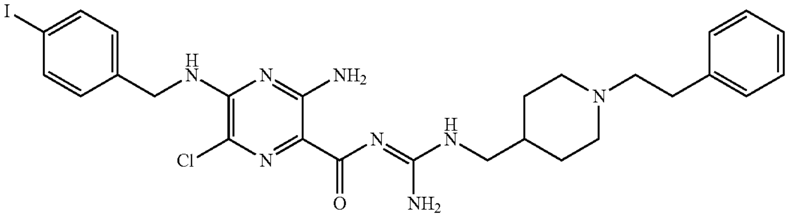

or a pharmaceutically acceptable salt thereof.

3. A compound having the following structure

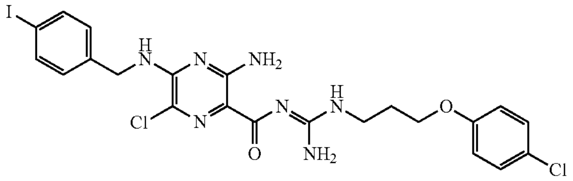 [SMILES: N/C(=N\C(=O)c1nc(Cl)c(NCc2ccc(I)cc2)nc1N)NCCCOc1ccc(Cl)cc1]

or a pharmaceutically acceptable salt thereof.

* * * * *